(12) United States Patent
Kanatzidis et al.

(10) Patent No.: US 9,181,475 B2
(45) Date of Patent: Nov. 10, 2015

(54) PHOTOLUMINESCENT COMPOUNDS

(71) Applicant: Northwestern University, Evanston, IL (US)

(72) Inventors: Mercouri G. Kanatzidis, Wilmette, IL (US); In Chung, Evanston, IL (US); Konstantinos Stoumpos, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 13/771,309

(22) Filed: Feb. 20, 2013

(65) Prior Publication Data

US 2013/0320836 A1    Dec. 5, 2013

Related U.S. Application Data

(60) Provisional application No. 61/601,219, filed on Feb. 21, 2012, provisional application No. 61/601,262, filed on Feb. 21, 2012.

(51) Int. Cl.
| | |
|---|---|
| *C09K 11/66* | (2006.01) |
| *C09K 11/06* | (2006.01) |
| *F21K 2/00* | (2006.01) |
| *H01L 31/032* | (2006.01) |
| *H01G 9/20* | (2006.01) |

(52) U.S. Cl.
CPC .............. *C09K 11/665* (2013.01); *C09K 11/06* (2013.01); *F21K 2/00* (2013.01); *H01G 9/20* (2013.01); *H01L 31/032* (2013.01); *C09K 2211/10* (2013.01); *Y02E 10/542* (2013.01)

(58) Field of Classification Search
USPC .................................................. 252/301.4 H
See application file for complete search history.

(56) References Cited

U.S. PATENT DOCUMENTS

| | | | | |
|---|---|---|---|---|
| 3,580,748 | A | * | 5/1971 | Delong ........................... 148/26 |
| 5,882,548 | A | | 3/1999 | Liang et al. |
| 6,880,746 | B2 | * | 4/2005 | Seseke-Koyro et al. ...... 228/223 |

(Continued)

FOREIGN PATENT DOCUMENTS

| | | | |
|---|---|---|---|
| GB | 957191 | * | 5/1964 |
| JP | 5-279009 | * | 10/1993 |

(Continued)

OTHER PUBLICATIONS

Papavassiliou et al., Excitonic Bands in the Photoconductivity Spectra of Some Organic-Inorganic Hybrid Compounds Based on Metal Halide Units, International Journal of Modern Physics B, vol. 15, Nos. 28, 29 & 30, 2001, pp. 3727-3731.

(Continued)

*Primary Examiner* — Carol M Koslow
(74) *Attorney, Agent, or Firm* — Bell & Manning, LLC

(57) ABSTRACT

Materials comprising an A/M/X compound are provided. An A/M/X compound is a compound comprising one or more A moieties, one or more M atoms and one or more X atoms, where the A moieties are selected from organic cations and elements from Group 1 of the periodic table, the M atoms are selected from elements from Group 14 of the periodic table, and the X atoms are selected from elements from Group 17 of the periodic table. The materials include two-phase materials in which the A/M/X compound provides a first phase and a metal oxide or metal halide compound provides a second phase.

23 Claims, 28 Drawing Sheets

(56) References Cited

U.S. PATENT DOCUMENTS

| | | | |
|---|---|---|---|
| 7,641,815 B2 * | 1/2010 | Varadarajan et al. ... | 252/301.4 H |
| 2002/0036298 A1 | 3/2002 | Nelles et al. | |
| 2002/0153510 A1 | 10/2002 | Sun et al. | |
| 2007/0085051 A1 | 4/2007 | Sohn et al. | |
| 2008/0014463 A1 | 1/2008 | Varadarajan et al. | |
| 2008/0038494 A1 | 2/2008 | Midgley et al. | |
| 2008/0202583 A1 | 8/2008 | Lee | |
| 2010/0055350 A1 | 3/2010 | Pfenninger et al. | |
| 2011/0180757 A1 | 7/2011 | Vockic et al. | |
| 2012/0305918 A1 | 12/2012 | Shum | |
| 2012/0306053 A1 | 12/2012 | Shum et al. | |
| 2013/0233377 A1 | 9/2013 | Kanatzidis et al. | |

FOREIGN PATENT DOCUMENTS

| | | |
|---|---|---|
| JP | 2003142168 | 5/2003 |
| KR | 10-20110066382 | 6/2011 |

OTHER PUBLICATIONS

Shum et al., Synthesis and characterization of CsSnI3 thin films, Applied Physics Letters, vol. 96, No. 221903, Jun. 2, 2010, pp. 1-3.
International Search Report and Written Opinion issued in PCT/US2013/026827, Jun. 14, 2013.
International Search Report and Written Opinion issued in PCT/US2013/027087, Jun. 21, 2013.
Yamada et al., Structure and Bonding of Two Modifications of CsSnI3 by Means of Powder X-Ray Diffraction, 127I NQR, and DTA, Chemistry Letters, 1989, pp. 1325-1328.
Yamada et al., Structural Phase Transitions of the Polymorphs of CsSnI3 by Means of Rietveld Analysis of the X-Ray Diffraction, Chemistry Letters, 1991, pp. 801-804.
Trots et al., High-temperature structural evolution of caesium and rubidium triiodoplumbates, Journal of Physics and Chemistry of Solids, vol. 69, 2008, pp. 2520-2526.
Takahashi et al., Charge-transport in tin-iodide perovskite CH3NH3SnI3: origin of high conductivity, Dalton Transactions, vol. 40, Apr. 14, 2011, pp. 5563-5568.
Yamada et al., Tunable Perovskite Semiconductor CH3NH3SnX3 (X: Cl, Br, or I) Characterized by X-ray and DTA, Bull. Chem. Soc. Jpn., vol. 84, No. 9, Aug. 27, 2011, pp. 926-932.
Papavassiliou et al., Structural, optical and related properties of some natural three- and lower-dimensional semiconductor systems, Synthetic Metals, vol. 71, 1995, pp. 1713-1714.
D. Mitzi, Synthesis, Crystal Structure, and Optical and Thermal Properties of (C4H9NH3)2MI4 (M) Ge, Sn, Pb), Chem. Mater., vol. 8, 1996, pp. 791-800.
G.C. Papavassiliou, Three- and Low-Dimensional Inorganic Semiconductors, Prog. Solid St. Chem., vol. 25, 1997, pp. 125-270.
Billing et al., Inorganic-organic hybrid materials incorporating primary cyclic ammonium cations: The lead bromide and chloride series, CrystEngComm, vol. 11, May 18, 2009, pp. 1549-1562.
Mercier et al., Structural diversity and retro-crystal engineering analysis of iodometalate hybrids, CrystEngComm, vol. 11, 2009, pp. 720-734.
Wu et al., Structural overview and structure-property relationships of iodoplumbate and iodobismuthate, Coordination Chemistry Reviews, vol. 253, Aug. 12, 2009, pp. 2787-2804.
Mitzi et al., Conducting tin halides with a layered organic-based perovskite structure, Nature, vol. 369, Jun. 9, 1994, pp. 467-469.
Mitzi et al., Transport, Optical, and Magnetic Properties of the Conducting Halide Perovskite CH3NH3SnI3, Journal of Solid State Chemistry, vol. 114, 1995, pp. 159-163.
Mitzi et al., Synthesis, Resistivity, and Thermal Properties of the Cubic Perovskite NH2CH5NH2SnI3 and Related Systems, Journal of Solid State Chemistry, vol. 134, 1997, pp. 376-381.
Calabrese et al., Preparation and Characterization of Layered Lead Halide Compounds, J. Am. Chem. Soc., vol. 113, 1991, pp. 2328-2330.
Chung et al., CsSnI3: Semiconductor or Metal? High Electrical Conductivity and Strong Near-Infrared Photoluminescence from a Single Material. High Hole Mobility and Phase-Transitions, J. Am. Chem. Soc., vol. 134, May 11, 2012, pp. 8579-8587.
Tanaka et al., Comparative study on the excitons in lead-halide-based perovskite-type crystals CH3NH3PbBr3 CH3NH3PbI3, Solid State Communications, vol. 127, 2003, pp. 619-623.
Im et al., 6.5% efficient perovskite quantum-dot-sensitized solar cell, Nanoscale, vol. 3, Sep. 7, 2011, pp. 4088-4093.
Chung et al., All-solid-state dye-sensitized solar cells with high efficiency, Nature, vol. 485, May 24, 2012, pp. 486-490.
Etgar et al., Mesoscopic CH3NH3PbI3/TiO2 Heterojunction Solar Cells, J. Am. Chem. Soc., vol. 134, Oct. 8, 2012, pp. 17396-17399.
Lee et al., Efficient Hybrid Solar Cells Based on Meso-Superstructured Organometal Halide Perovskites, Science, vol. 338, Nov. 2, 2012, pp. 643-647.
Scaife et al., Crystal Preparation and Properties of Cesium Tin(II) Trihalides, Journal of Solid State Chemistry, vol. 9, 1974, pp. 308-314.
Yu et al., Temperature dependence of the band gap of perovskite semiconductor compound CsSnI3, Journal of Applied Physics, vol. 110, No. 063526, Sep. 27, 2011, pp. 1-5.
Chen et al., Photoluminescence study of polycrystalline CsSnI3 thin films:Determination of exciton binding energy, Journal of Luminescence, vol. 132, Sep. 10, 2011, pp. 345-349.
Poglitsch et al., Dynamic disorder in methylammoniumtrihalogenoplumbates (II) observed by millimeterwave spectroscopy, J. Chem. Phys., vol. 87, 1987, pp. 6373-6378.
Onoda-Yamamuro et al., p-T Phase Relations of CH3NH3PbX3 (X=Cl, Br, I) Crystals, J. Phys. Chem. Solids, vol. 53, No. 2, 1992, pp. 277-281.
Howie et al., The Crystal Structure of Tin(II) Iodide, Acta Crystallographica, Sect. B, vol. 28, 1972, pp. 2965-2971.
G. Sheldrick, A short history of SHELX, Acta Crystallographica, Sect. A, vol. 64, 2008, pp. 112-122.
Howard et al., Group-Theoretical Analysis of Octahedral Tilting in Perovskites, Acta Crystallographica, Sect. B, vol. 54, 1998, pp. 782-789.
Howard et al., Octahedral tilting in cation-ordered perovskites—a group-theoretical analysis, Acta Crystallographica, Sect. B, vol. 60, 2004, pp. 674-684.
Howard et al., Structures and phase transitions in perovskites—a group-theoretical approach, Acta Crystallographica, Sect. A, vol. 61, 2005, pp. 93-111.
Swainson et al., Orientational ordering, tilting and lone-pair activity in the perovskite methylammonium tin bromide, CH3NH3SnBr3, Acta Crystallographica, Sect. B, vol. 66, 2010, pp. 422-429.
Borriello et al., Ab initio investigation of hybrid organic-inorganic perovskites based on tin halides, Physical Review B, vol. 77, No. 235214, Jun. 23, 2008, pp. 1-9.
Kojima et al., Organometal Halide Perovskites as Visible-Light Sensitizers for Photovoltaic Cells, J. Am. Chem. Soc., vol. 131, 2009, pp. 6050-6051.
M. Gratzel, Recent Advances in Sensitized Mesoscopic Solar Cells, Accounts of Chemical Research, vol. 42, No. 11, Nov. 2009, pp. 1788-1798.
Yanagida et al., Iodine/Iodide-Free Dye-Sensitized Solar Cells, Accounts of Chemical Research, vol. 42, No. 11, Nov. 2009, pp. 1827-1838.
Wang et al., An organic redox electrolyte to rival triiodide/iodide in dye-sensitized solar cells, Nature Chemistry, vol. 2, Apr. 4, 2010, pp. 385-389.
Mitzi et al., Conducting Layered Organic-Inorganic Halides Containing (110)-Oriented Perovskite Sheets, Science, vol. 267, Mar. 10, 1995, pp. 1473-1476.
Xu et al., Molecular Motions and Phase Transitions in Solid $CH_3NH_3PbX_3$ (X=Cl, Br, I) as Studied by NMR and NQR, Z. Naturforsch, vol. 46a, 1991, pp. 240-246.
Kojima et al., Novel Photoelectrochemical Cell with Mesoscopic Electrodes Sensitized by Lead-halide Compounds (11), 214th ECS Meeting, Abstract #27, The Electrochemical Society, Oct. 13, 2008.
Li et al., Photoconductive Properties of Organic-Inorganic Hybrid Perovskite $(C_6H_{13}NH_3)_2(CH_3NH_3)_{m-1}Pb_mI_{3m+1}$ :TiO2 Nanocomposites Device Structure, Materials Letters, vol. 64, 2010, pp. 2735-2737.

* cited by examiner

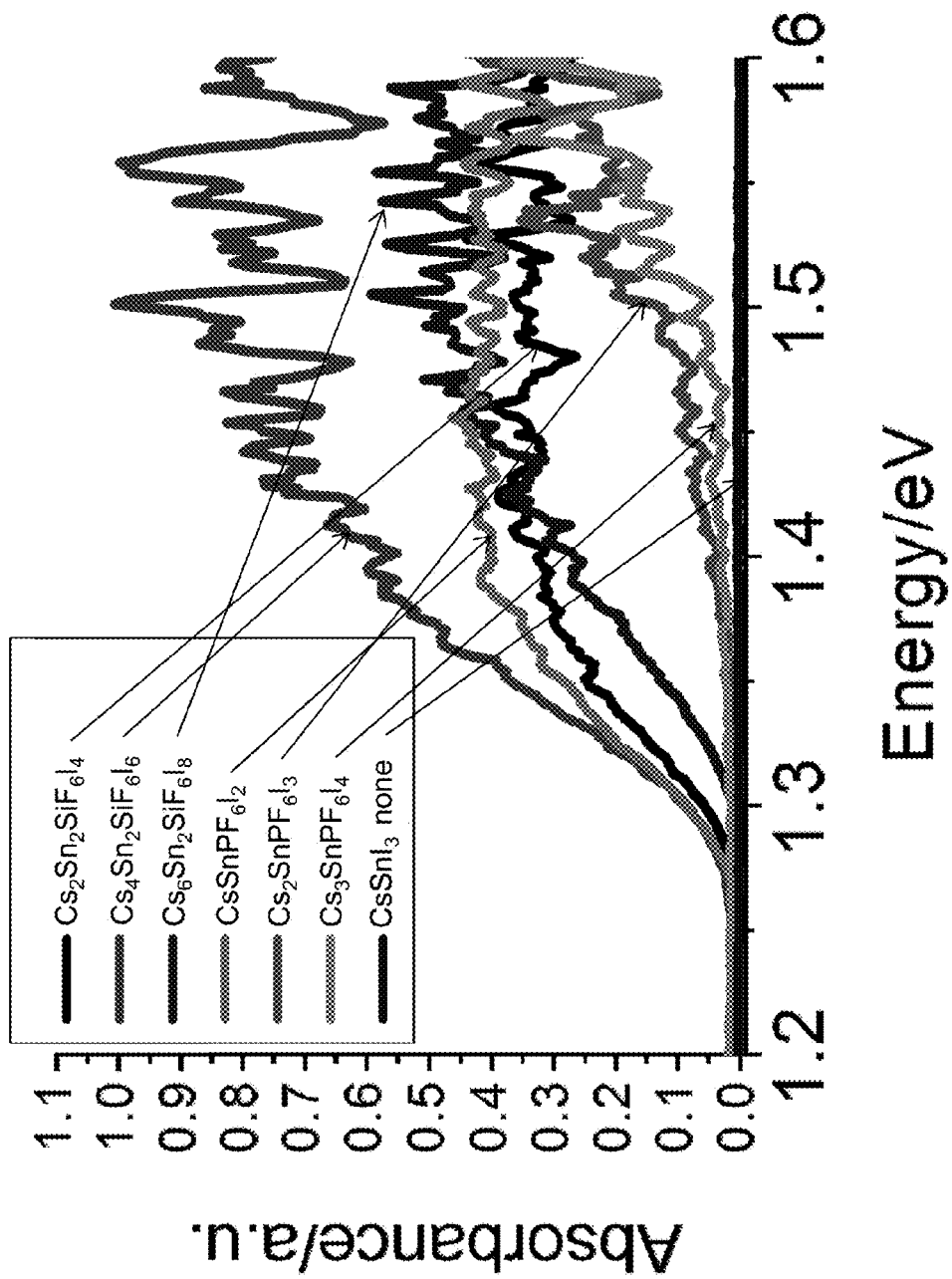

PHOTOLUMINESCENT COMPOUNDS

CROSS-REFERENCE TO RELATED APPLICATIONS

This application claims priority from U.S. provisional patent application Ser. No. 61/601,262, filed on Feb. 21, 2012, and from U.S. provisional patent application Ser. No. 61/601,219, filed on Feb. 21, 2012, both of which are incorporated herein by reference.

BACKGROUND

Some metal halide compounds such as $CsSnI_3$ have been reported to exhibit strong photoluminescence (PL) at RT.

Thin films of $CsSnI_3$, $CsSnI_2Cl$ and $CsSnICl_2$ have been prepared by the thermal and e-beam evaporation methods. However, such high vacuum techniques are expensive, inadequate for controlling compositions and homogeneity and can suffer from reproducibility.

SUMMARY

Material comprising an A/M/X compound are provided. Also provided are solution-based methods of making film comprising the A/M/X compounds and photolumenescent light sources incorporating the materials. An A/M/X compound is a compound comprising one or more A moieties, one or more M atoms and one or more X atoms, where the A moieties are selected from organic cations and elements from Group 1 of the periodic table, the M atoms are selected from elements from Group 14 of the periodic table, and the X atoms are selected from elements from Group 17 of the periodic table. In the A/M/X compounds, M may represent two or more different M atoms (i.e., different M elements) and/or X may represent two or more different X atoms (e.g., different halogen elements).

The compounds are electrically conductive and photoluminescent, characterized by photoluminescence wavelengths in the range of about 400 nm to about 2000 nm at room temperature (23° C.). This includes compounds having photoluminescent wavelengths in the range from about 700 nm to about 2000 nm and compounds having photoluminescence wavelengths in the range of about 800 nm to about 1200 nm at room temperature (23° C.).

One embodiment of the material comprises a compound having a formula selected from $AMX_3$, $A_2MX_4$, $AM_2X_5$ or $A_2MX_6$, where the A is selected from elements from Group 1 of the periodic table, the M is selected from elements from Group 14 of the periodic table, and X is selected from elements from Group 17 of the periodic table, and either metal oxides of the formula $M'O_{y'}$, where y'=1, 1.5 or 2, or metal halides of the formulas $A_2M'X_6$ or $A_3M'X_6$, where M' is selected from elements of Groups 2-4 or elements of Groups 12-15 of the periodic table. The metal oxide or metal halide compounds can form a second phase in the material, such that the material comprises a first phase of the A/M/X compounds and second phase of the metal oxide or metal halide compounds. In some members of this embodiment, the compound has the formula $AMX_3$, such that the material has the formula $(AMX_3)_{1-x}(M'O_{y'})_x$. This includes compounds wherein $AMX_3$ is $CsSnI_3$. In other members of this embodiment, the compound has the formula $A_2MX_4$, such that the material has the formula $(A_2MX_4)_{1-x}(M'O_{y'})_x$. This includes compounds wherein $(A_2MX_4)$ is $Cs_2SnI_4$. The metal oxides include oxides of metals selected from Group 3, Group 4, Group 12, Group 13, Group 14, and Group 15 of the periodic table. For example, $TiO_2$ is a suitable metal oxide. Where 0.01<x<0.99 in the formulas.

In some members of this embodiment, the $AMX_3$ compound comprises two X elements, such that the compound has the formula $AMX_{(3-x)}X'_x$, where X and X' are different halogen atoms and 0.01<x<0.99. In some such members, the material is a two-phase material comprising a first phase of $AMX_{(3-x)}X'_x$ and a second phase comprising a metal halide or a metal oxide.

Specific members of this embodiment include materials selected from the group consisting of $(CsSnI_3)_{1-x}(M'O)_x$, where M'=Si, Ge, Sn, or Pb); $(CsSnI_3)_{1-x}(M'O_{1.5})_x$, where M'=B, Al, Ga, In, Sc, or Y; $(CsSnI_3)_{1-x}(M'O_2)_x$, where M'=Si, Ge, Sn, or Pb; $(Cs_2SnI_4)_{1-x}(M'O)_x$, where M'=Si, Ge, Sn, or Pb; $(Cs_2SnI_4)_{1-x}(M'O_{1.5})_x$, where M'=B, Al, Ga, In, Sc, or Y; $(Cs_2SnI_4)_{1-x}(M'O_2)_x$, M'=Si, Ge, Sn, or Pb; $Cs(SnI_3)_{1-x}(M'O)_x$, M'=Si, Ge, Sn, or Pb; $Cs(SnI_3)_{1-x}(M'O_{1.5})_x$, M'=B, Al, Ga, In, Sc, or Y; $Cs(SnI_3)_{1-x}(M'O_2)_x$, M'=Si, Ge, Sn, or Pb; $Cs_2(SnI_4)_{1-x}(M'O)_x$, M'=Si, Ge, Sn, or Pb; $Cs_2(SnI_4)_{1-x}(M'O_{1.5})_x$, M'=B, Al, Ga, In, Sc, or Y; and $Cs_2(SnI_4)_{1-x}(M'O_2)_x$, M'=Si, Ge, Sn, or Pb, where 0.01<x<0.99.

In some members of this embodiment, in which the material comprises a metal halide, the metal halide is a metal fluoride. In some members, the metal halide comprises two or more M' elements. In the embodiments in which the material comprises a metal halide, the compound may comprise, for example, $CsSnI_3$ or $Cs_2SnI_4$.

Specific members of this embodiment include materials selected from the group consisting of $(CsSnI_3)_{1-x}(Cs_{1.5}M'_{0.5}F_3)_x$, M'=Al, Ga, In, Sc, or Y; $(CsSnI_3)_{1-x}(CsM'_{0.5}F_3)_x$, M'=Si, Ge, Sn, Ti, Zr, or Hf; $(Cs_2SnI_4)_{1-x}(Cs_{1.5}M'_{0.5}F_3)_x$, M'=Al, Ga, In, Sc, or Y; $(Cs_2SnI_4)_{1-x}(CsM'_{0.5}F_3)_x$, M'=Si, Ge, Sn, Ti, Zr, or Hf; $Cs(SnI_3)_{1-x}(Cs_{1.5}M'_{0.5}F_3)_x$, M'=Al, Ga, In, Sc, or Y; $Cs(SnI_3)_{1-x}(CsM'_{0.5}F_3)_x$, M'=Si, Ge, Sn, Ti, Zr, or Hf; where 0.01<x<0.99.

Another embodiment of the materials comprises compounds having a formula selected from $AMX_3$, $A_2MX_4$, $AM_2X_5$ or $A_2MX_6$, where the A is a monovalent organic ammonium cation, M represents one or more elements selected from elements from Group 14 of the periodic table, and X represents one or more halogen elements selected from elements from Group 17 of the periodic table, wherein the compound comprises more than one M element, more than one X element, or more than one of both. For example, in compounds comprising two M elements, those elements can be selected from Sn, Pb, Ge and Si. This includes members of this embodiment in which at least one of the M elements comprises Ge. Further included are compounds comprising $Sn_{(1-x)}Pb_x$, where 0.01<x<0.99. One such compound is $CH_3NH_3Sn_{1-x}Pb_xI_3$.

Specific examples of compounds which include more than one halogen element are those selected from the group consisting of $CH_3NH_3SnF_2I$, $CH_3NH_3SnCl_2I$, $CH_3NH_3SnBr_2I$, $CH_3NH_3SnI_2F$, $CH_3NH_3SnI_2Cl$, $CH_3NH_3SnI_2Br$, $HC(NH_2)_2SnF_2I$, $HC(NH_2)_2SnCl_2I$, $HC(NH_2)_2SnBr_2I$, $HC(NH_2)_2SnI_2Cl$, $HC(NH_2)_2SnI_2F$ and $HC(NH_2)_2SnI_2Br$.

Examples of monovalent organic ammonium cations include methyl ammonium ions, formamidinium ion, methylformamidinium ions and guanidinium ions.

Other embodiments of the materials comprise compounds having a formula selected from $AMX_3$, $A_2MX_4$, $AM_2X_5$ or $A_2MX_6$, where A is a methylformamidinium ion or a guanidinium ion, M is selected from elements from Group 14 of the periodic table, and X is a halogen atom. While still other embodiments of the materials comprise compounds having a formula selected from $AMX_3$, $A_2MX_4$, $AM_2X_5$ or $A_2MX_6$, where A is an organic ammonium ion, M is Ge and X is a halogen atom.

Photoluminescent light sources that incorporate the materials comprise an incident radiation source configured to generate incident radiation at an incident wavelength; and one or more of the materials recited herein, configured such that it is irradiated by incident radiation from the incident radiation source when the source is on. In the photoluminescent sources, the incident radiation and the material are characterized in that the material is able to absorb the incident radiation, whereby the material is induced to emit photoluminescence in the wavelength range of 400 to 2000 nm. The photoluminescent sources include infrared and near-infrared sources, in which the material photoluminesces in the wavelength range of 700 to 2000 nm. Optional components of the photoluminescent sources include more filters configured to which block emitted photoluminescence radiation having an undesired wavelength, while selectively transmitting emitted photoluminescence at other wavelengths. The source may also optionally include a photoluminescence detector configured such that the photoluminescence from the material impinges on the detector when the source is in operation.

Other devices into which the materials can be incorporated include light emitting diodes, sensors, and photovoltaic cells.

An embodiment of a solution-based film deposition process for A/M/X compounds comprises the steps of: forming a homogeneous solution of an A/M/X compound in a polar organic solvent; deposing the solution onto a substrate; and drying the deposited solution, whereby a film comprising the A/M/X compound is formed. Suitable polar organic solvents include acetonitrile, DMF, ethanol and mixtures thereof. Depositing the solution onto a substrate can be accomplished, for example, by drop-coating, spin-coating or spraying the solution onto the substrate. Drying the deposited solution can be carried out by heating the deposited solution. For example, the solution can be heated to a temperature of at least 50° C. Suitable substrates include silicon, glass, ceramic, metal foil and plastic substrates. The examples below describe the formation of a film comprising $CsSnI_3$ via a solution deposition process.

BRIEF DESCRIPTION OF THE DRAWINGS

FIG. 6. Optical absorption of $Cs_2Sn_2SiF_6I_4$, $Cs_4Sn_2SiF_6I_6$, $Cs_6Sn_2SiF_6I_8$, $CsSnPF_6I_2$, $Cs_2SnPF_6I_3$, $Cs_3SnPF_6I_4$, and $CsSnI_3$.

FIG. 22 (C) displays the spectra of specimens of 1-4 prepared with the solution method.

DETAILED DESCRIPTION

Figure 1:
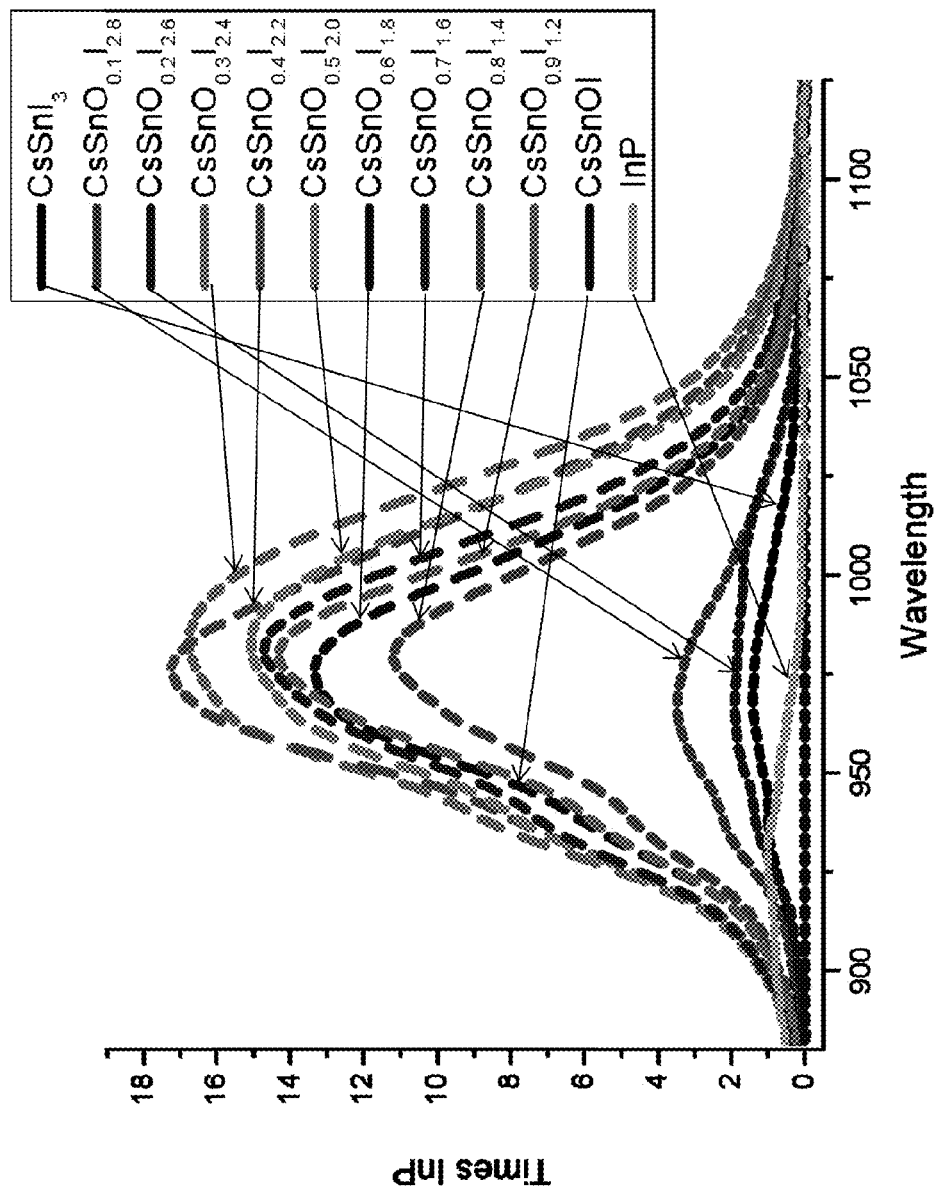
FIG. 1 is a graph of the PL emission vs. wavelength for $CsSnI_3$, $CsSnO_{0.1}I_{2.8}$, $CsSnO_{0.2}I_{2.6}$, $CsSnO_{0.3}I_{2.4}$, $CsSnO_{0.4}I_{2.2}$, $CsSnO_{0.5}I_{2.0}$, $CsSnO_{0.6}I_{1.8}$, $CsSnO_{0.7}I_{1.6}$, $CsSnO_{0.8}I_{1.4}$, $CsSnO_{0.9}I_{1.2}$, CsSnOI, and InP.
Figure 2:
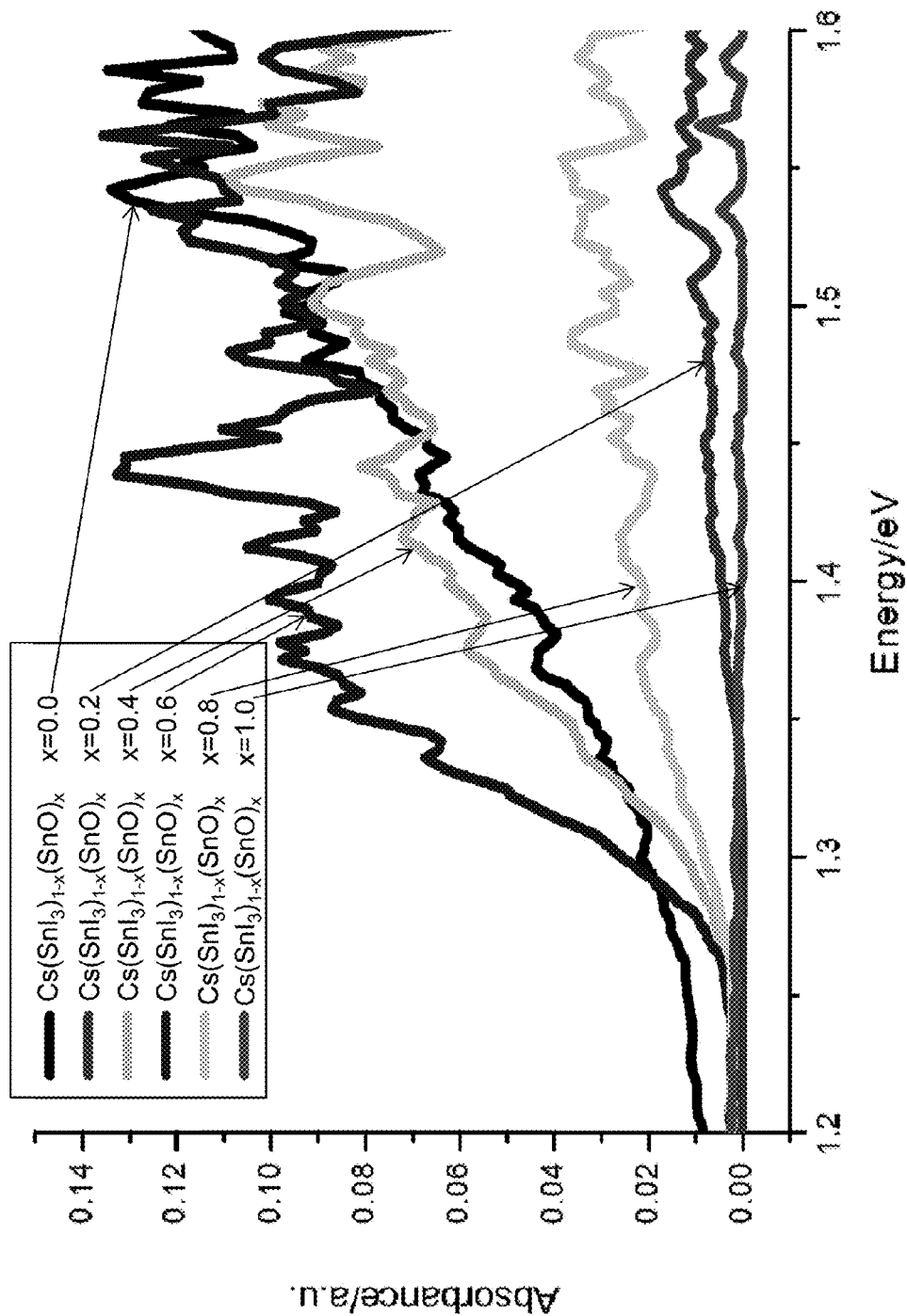
FIG. 2 shows the optical absorption spectra for different compositions of $Cs(SnI_3)_{1-x}(MO)_x$.
Figure 3:
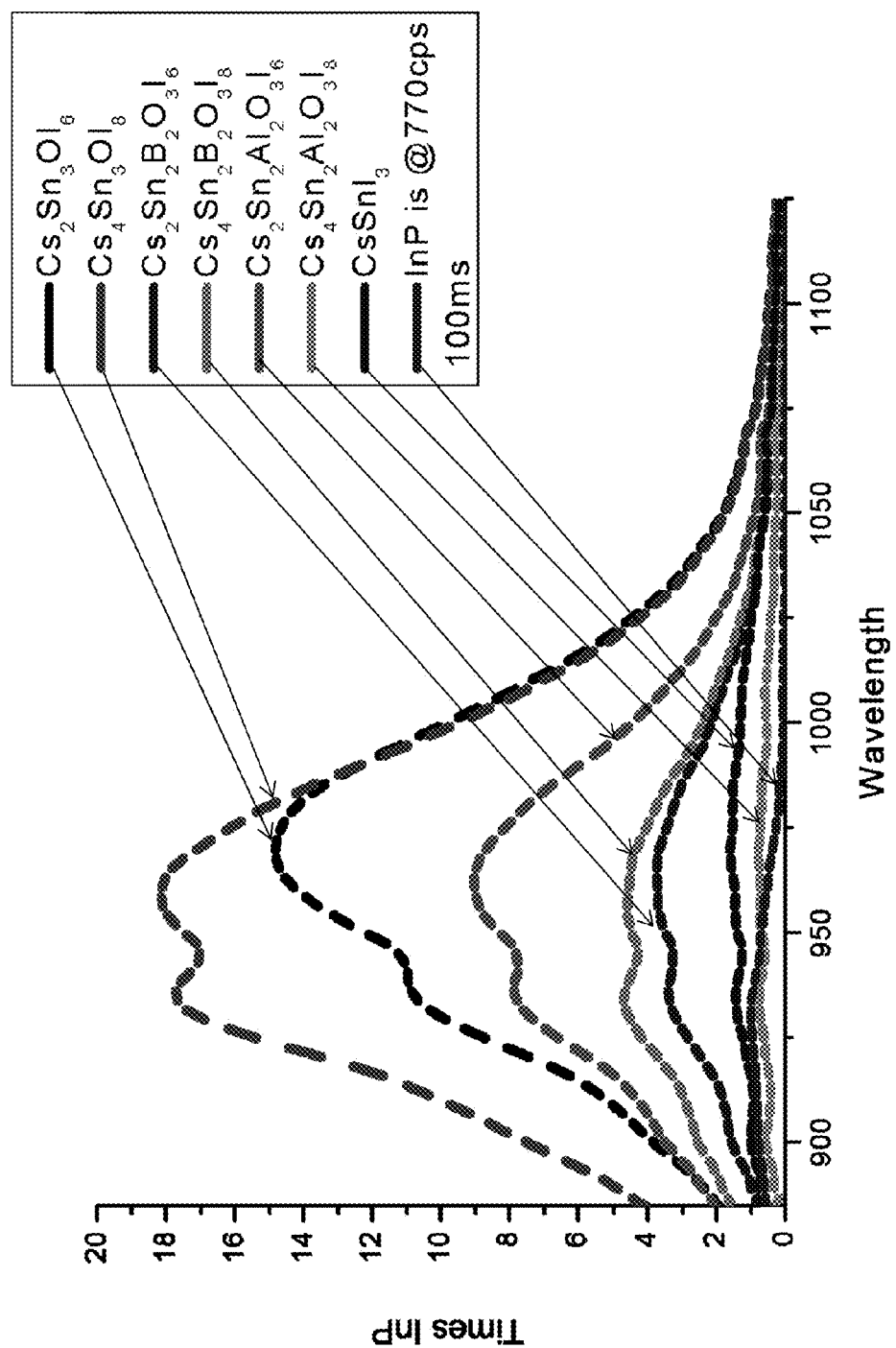
FIG. 3. PL emission vs. wavelength of $Cs_2Sn_3OI_6$, $Cs_4Sn_3OI_8$, $Cs_2Sn_2B_2O_3I_6$, $Cs_4Sn_2B_2O_3I_8$, $Cs_2Sn_2Al_2O_3I_6$, $Cs_4Sn_2Al_2O_3I_8$, $CsSnI_3$, and InP.
Figure 4:
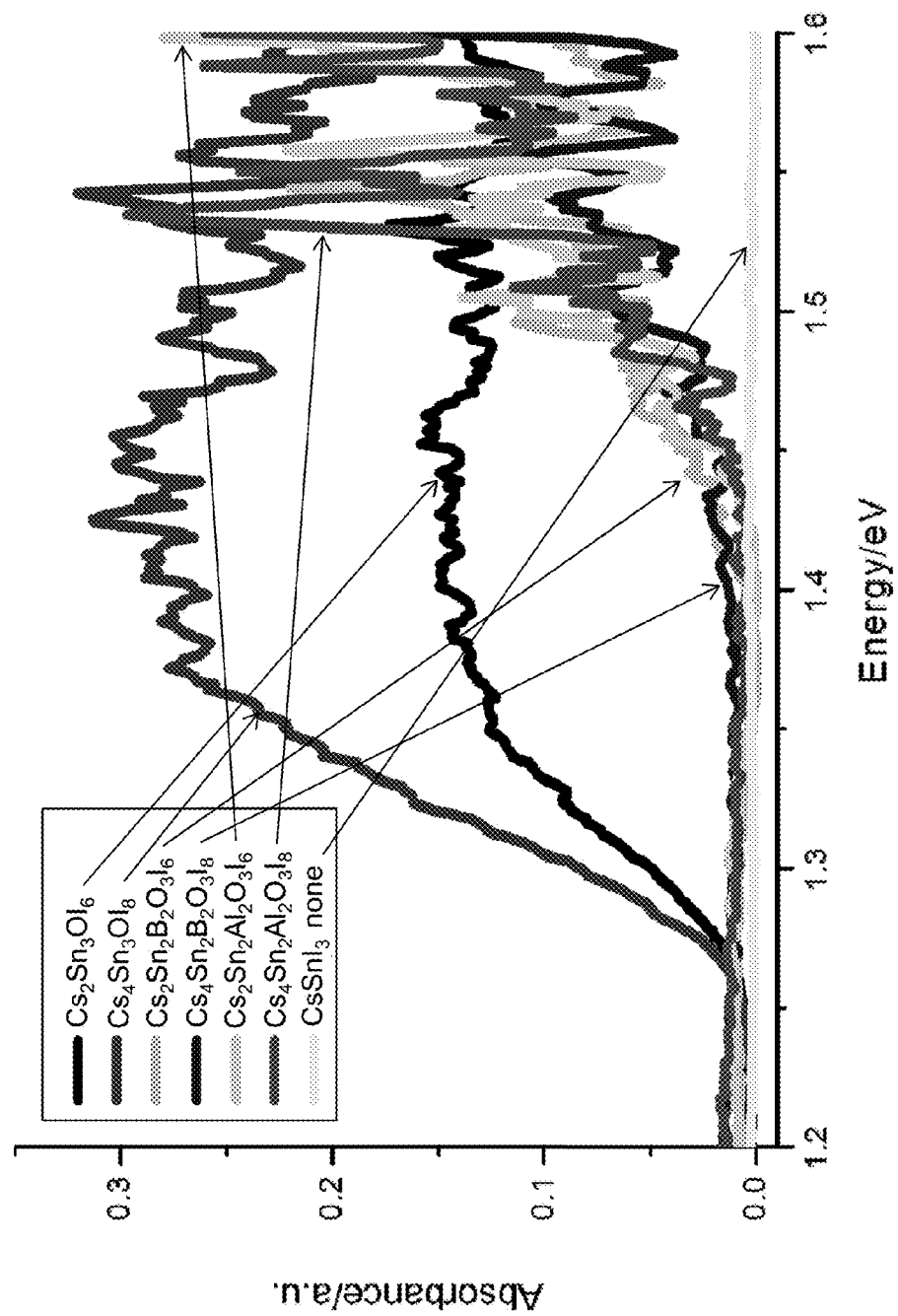
FIG. 4. Optical absorption spectra of $Cs_2Sn_3OI_6$, $Cs_4Sn_3OI_8$, $Cs_2Sn_2B_2O_3I_6$, $Cs_4Sn_2B_2O_3I_8$, $Cs_2Sn_2Al_2O_3I_6$, $Cs_4Sn_2Al_2O_3I_8$, and $CsSnI_3$.
Figure 5A:
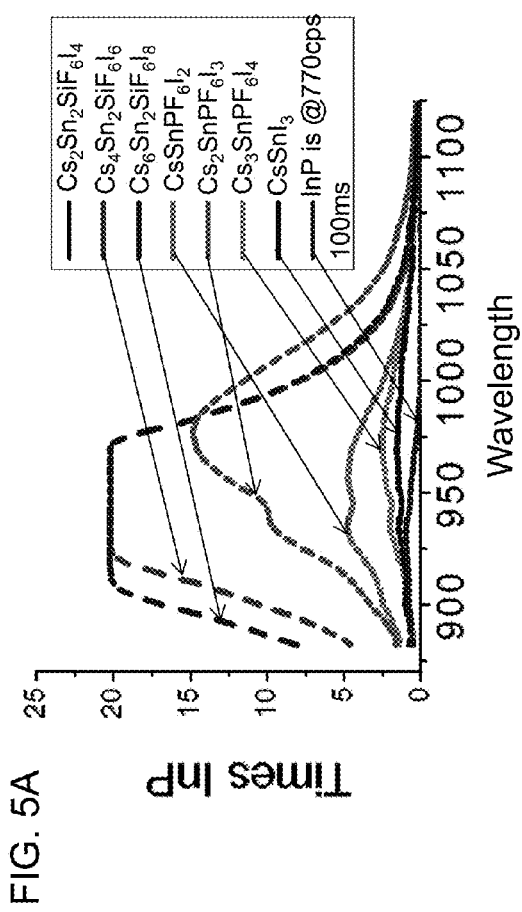
FIG. 5. PL emission vs. wavelength of: (A) $Cs_2Sn_2SiF_6I_4$, $Cs_4Sn_2SiF_6I_6$, $Cs_6Sn_2SiF_6I_8$, $CsSnPF_6I_2$, $Cs_2SnPF_6I_3$, $Cs_3SnPF_6I_4$, $CsSnI_3$, and InP. (B) The $Cs_4Sn_2SiF_6I_6$ phase that saturated the detector, measured at lower integration time. (C) The $Cs_6Sn_2SiF_6I_8$ phase that saturated the detector, measured at lower integration time.
Figure 5C:
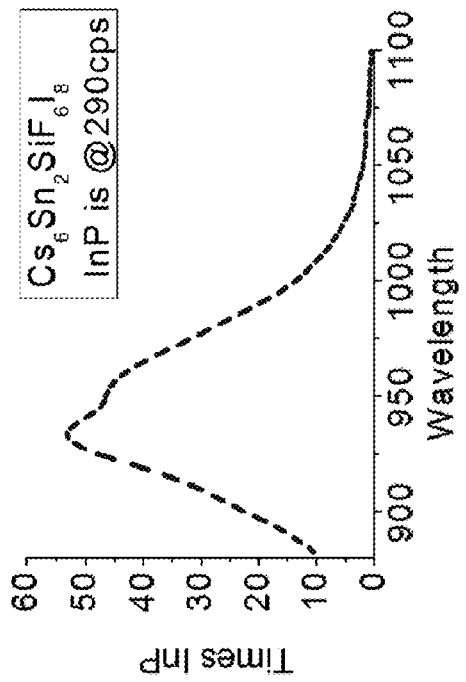
Figure 5B:
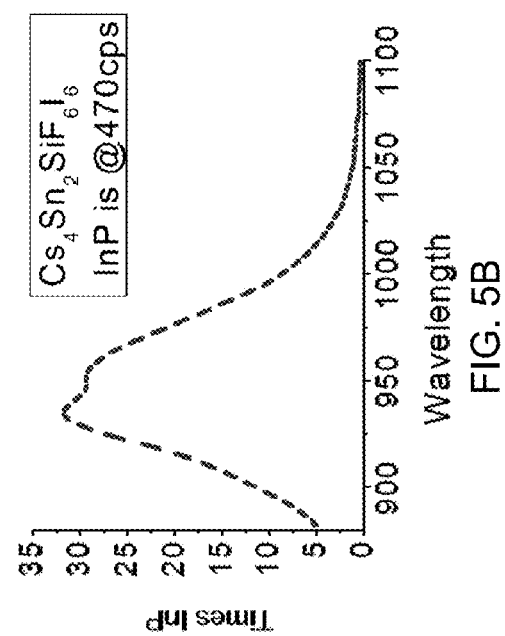
Figure 7A:
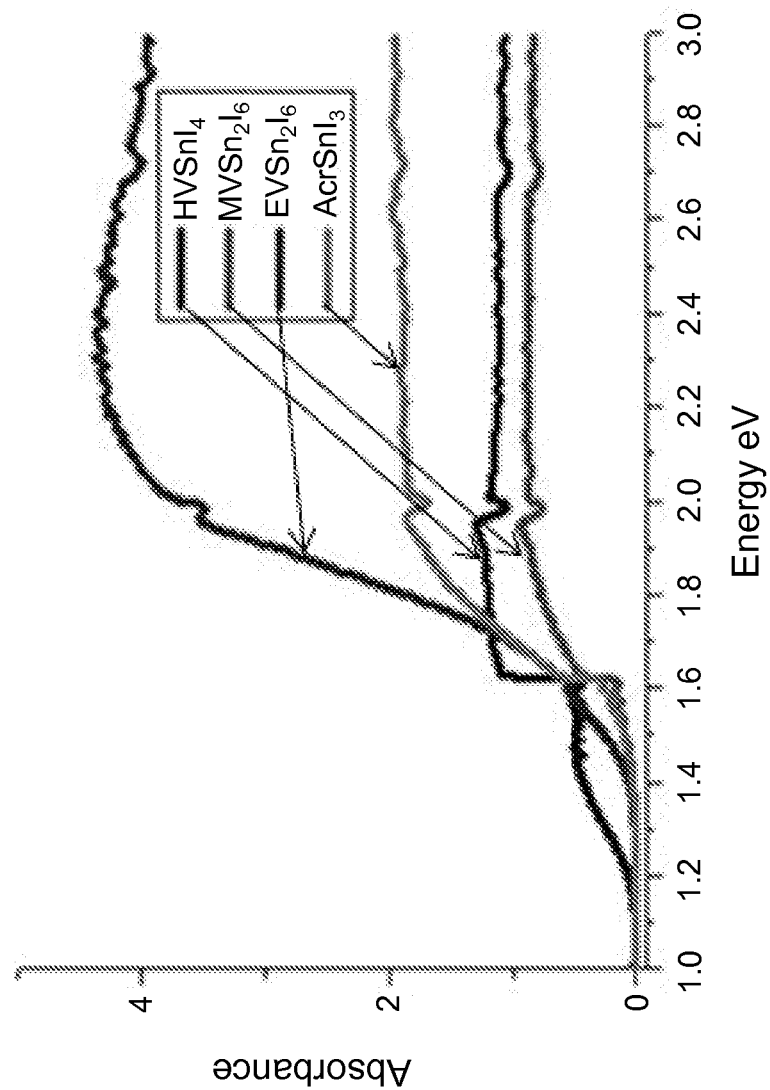
FIG. 7. Optical absorption (A) and PL emission (B) vs. energy of Type IIB materials on 785 nm (1.58 eV) excitation as measured using a Raman scattering setup.
Figure 7B:
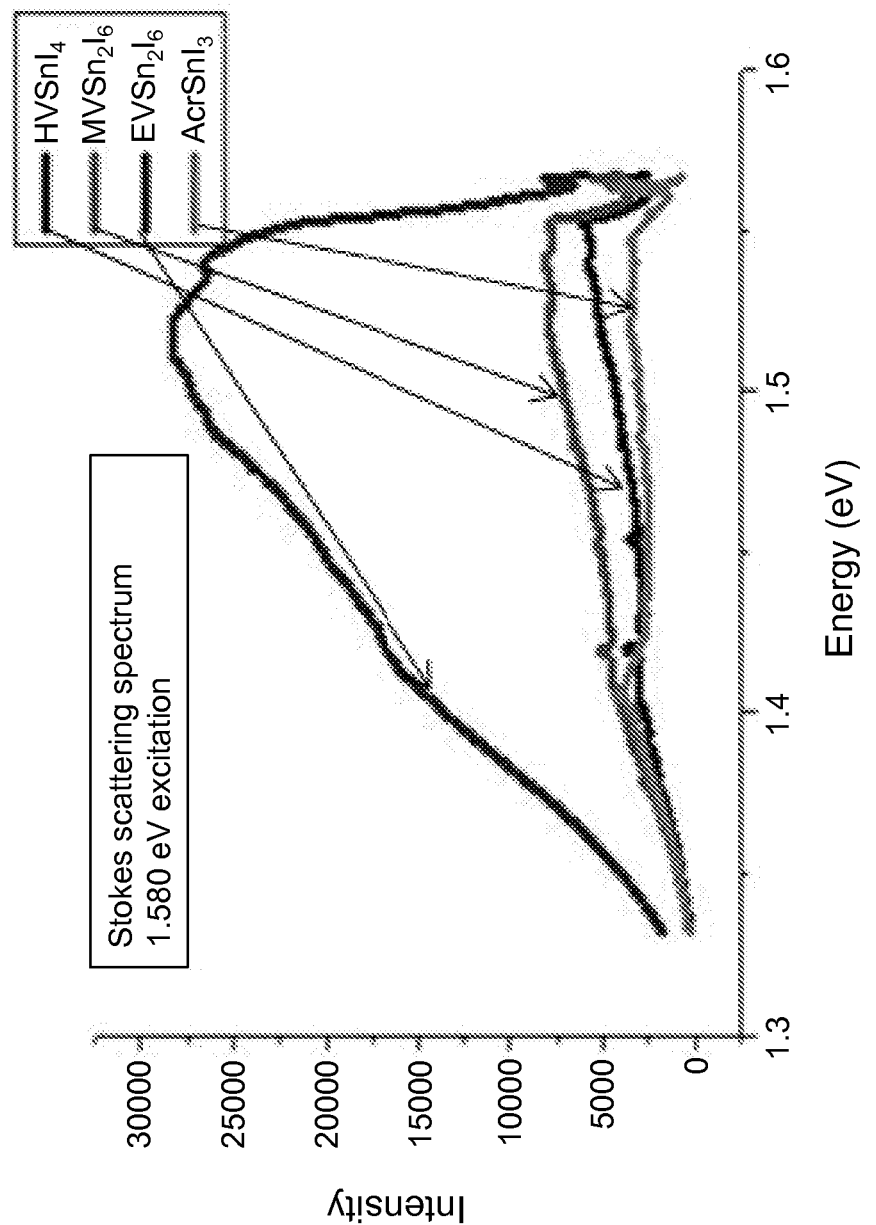
Figure 8:
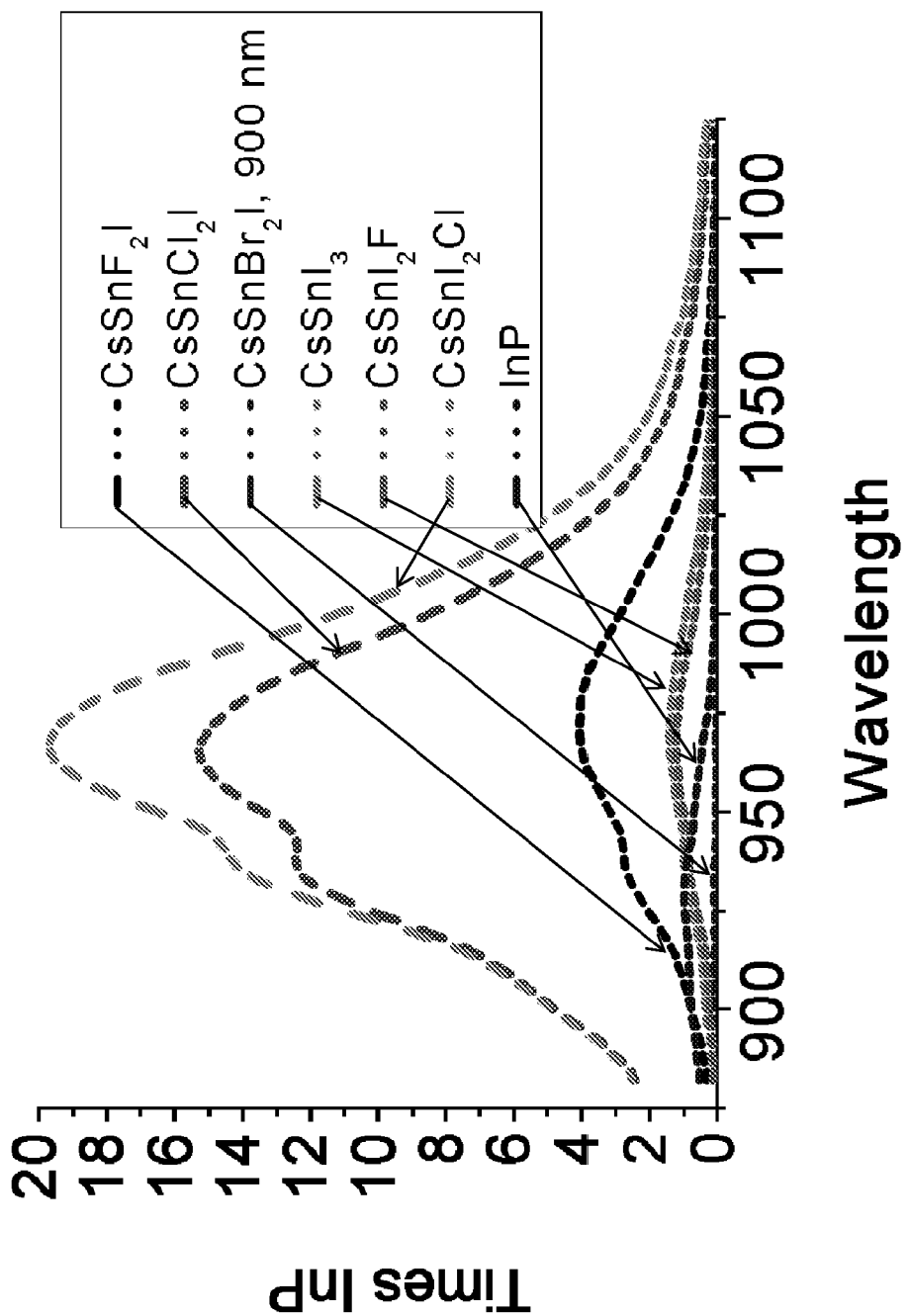
FIG. 8. PL emission vs. wavelength for $CsSn(I_{3-x}X_x)$ compositions.
Figure 9:
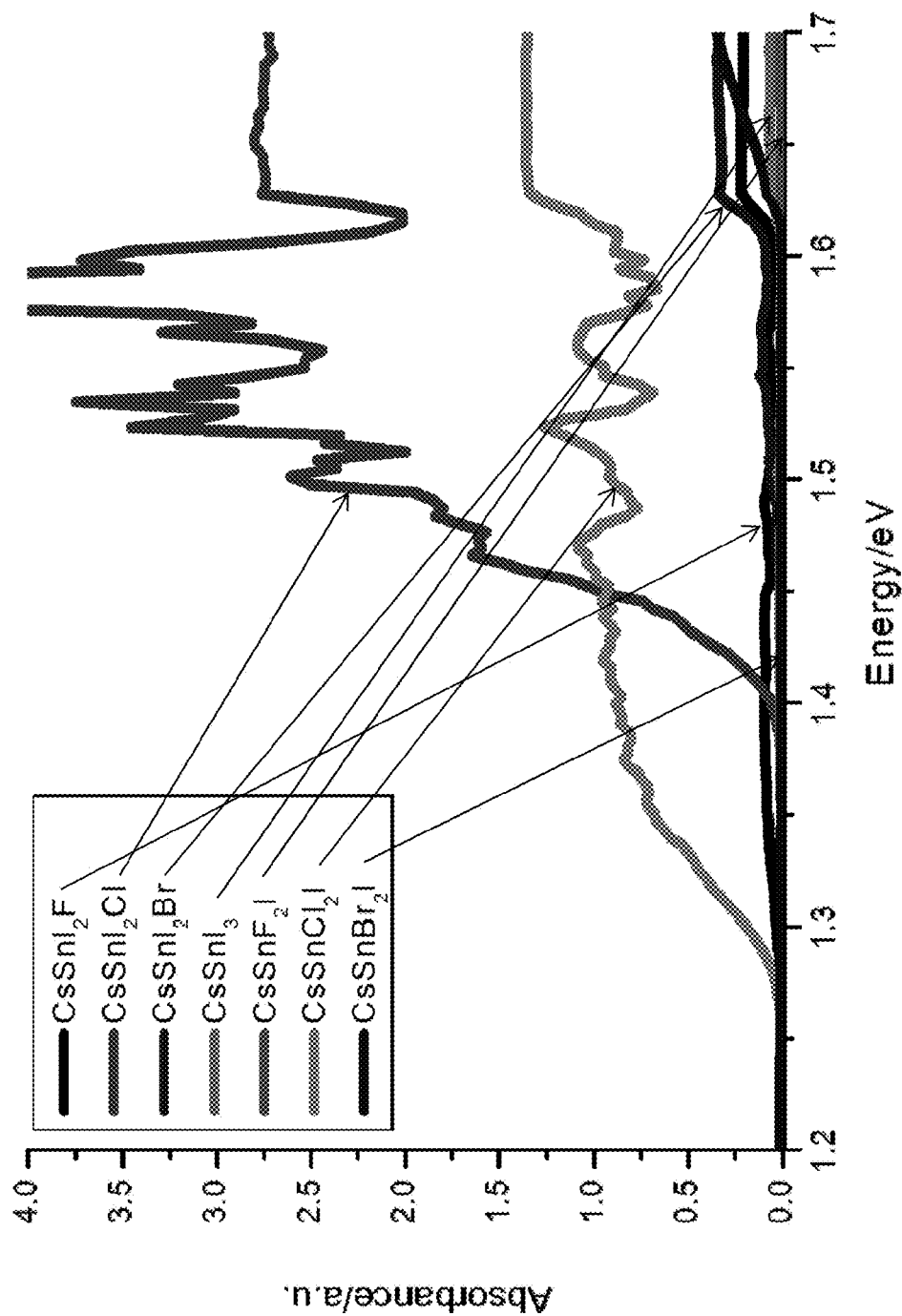
FIG. 9. Optical absorption spectra for $CsSn(I_{3-x}X_x)$ compositions.
Figure 10:
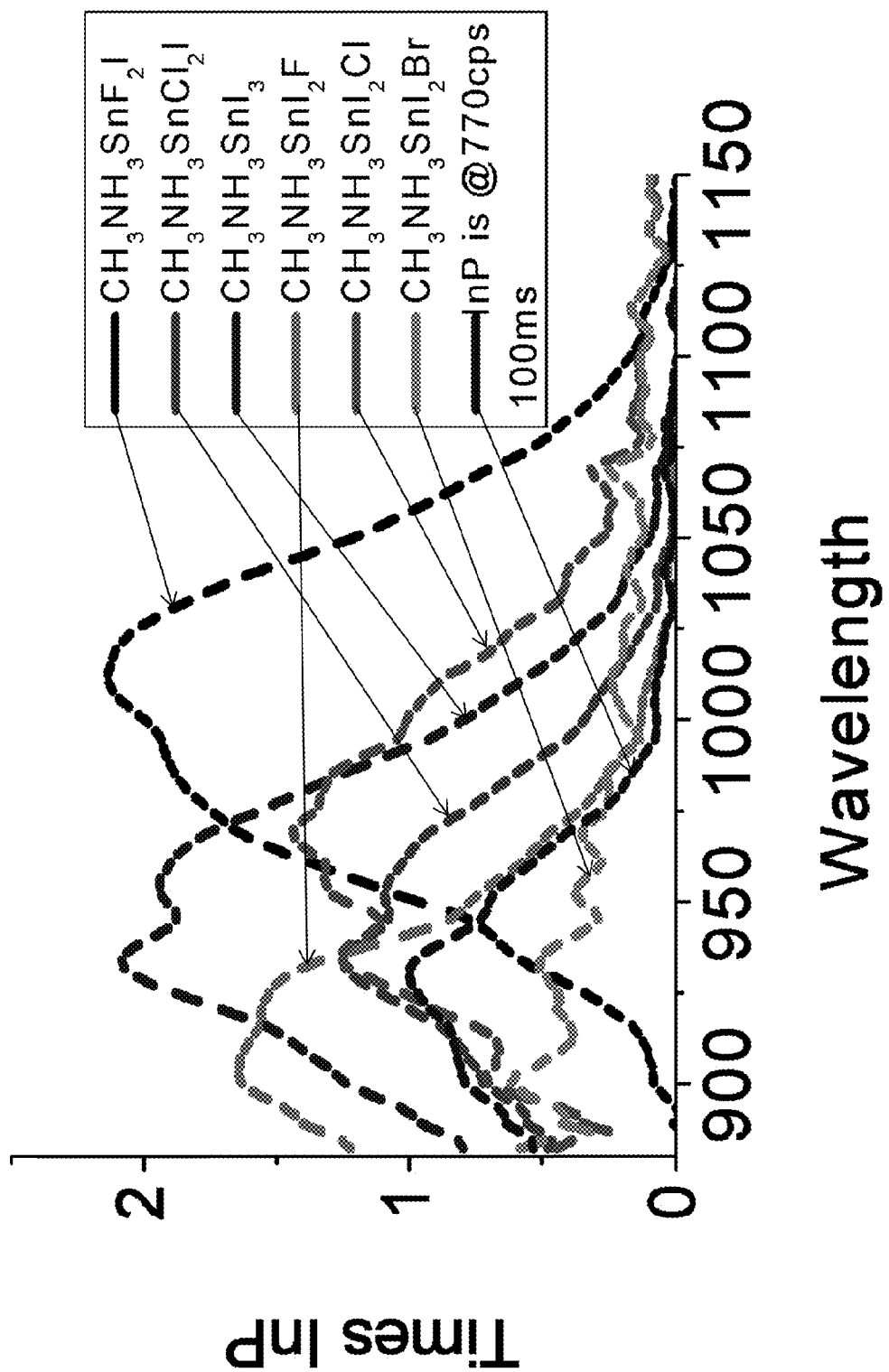
FIG. 10. PL emission vs. wavelength for $CH_3NH_3Sn(I_{3-x}X_x)$ compositions.
Figure 11:
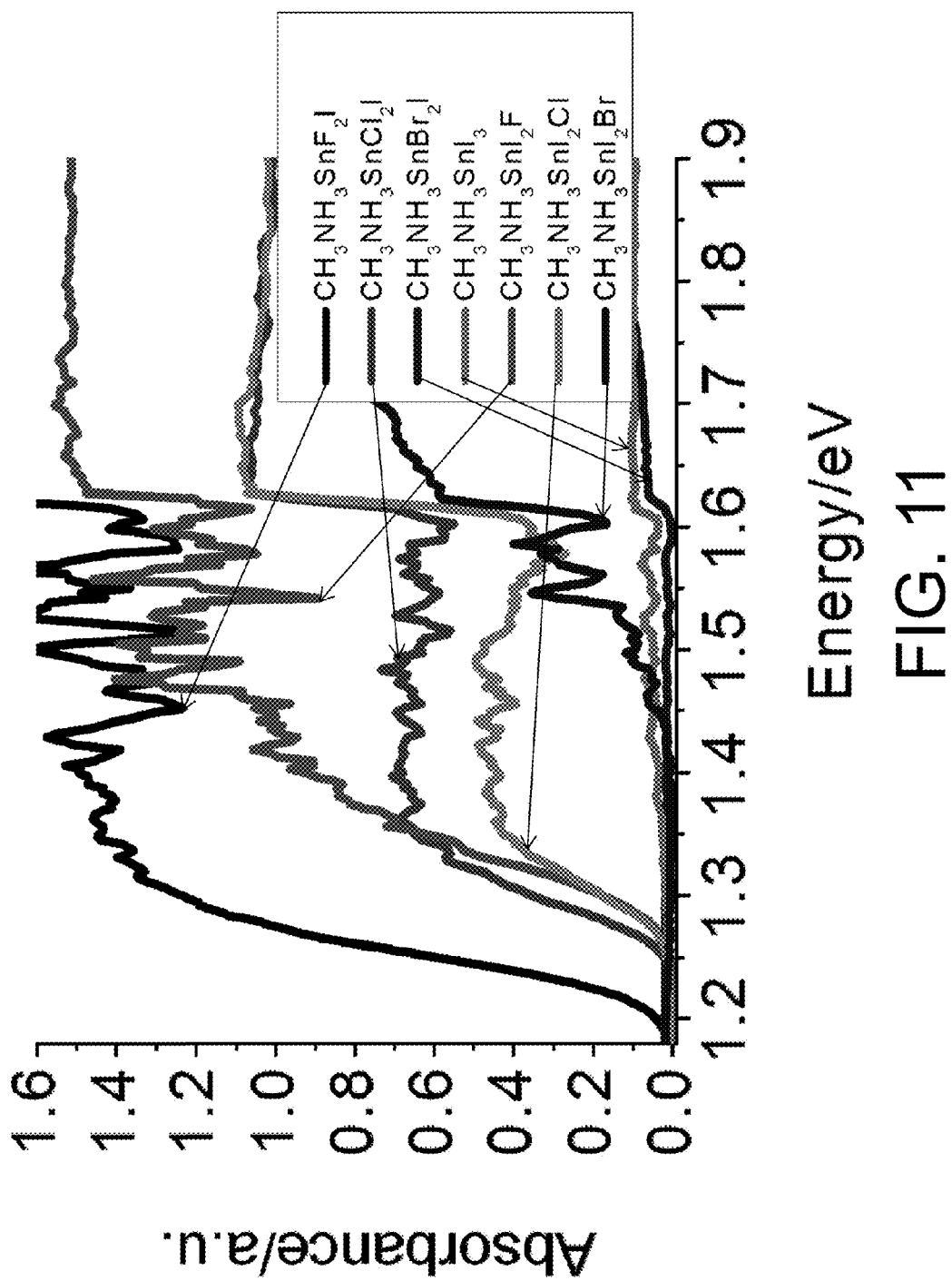
FIG. 11. Optical absorption for $CH_3NH_3Sn(I_{3-x}X_x)$ compositions.
Figure 12B:
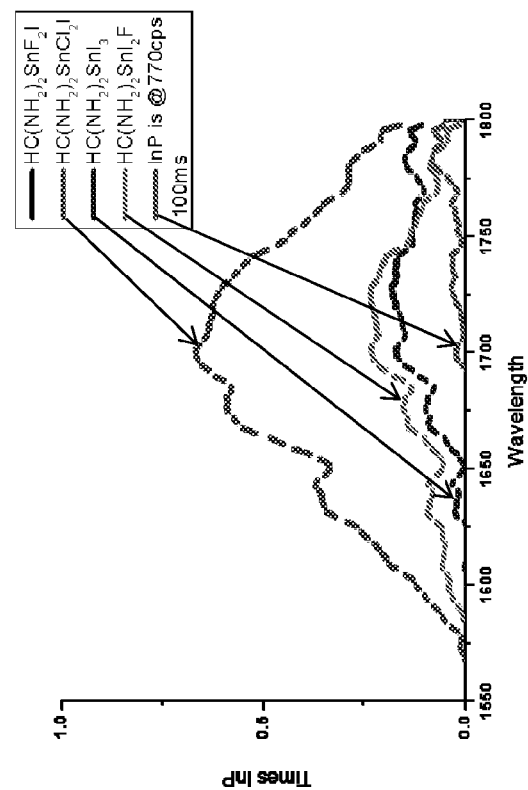
FIG. 12. PL emission vs. wavelength for $HC(NH_2)_2Sn(I_{3-x}X_x)$ compositions showing a first (A) and a second (B) emission wavelength range.
Figure 12A:
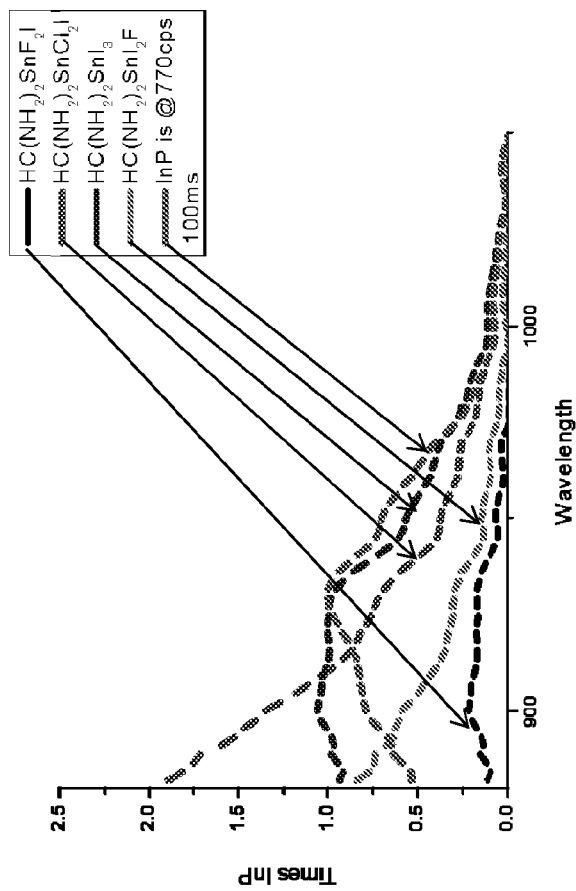
Figure 13:
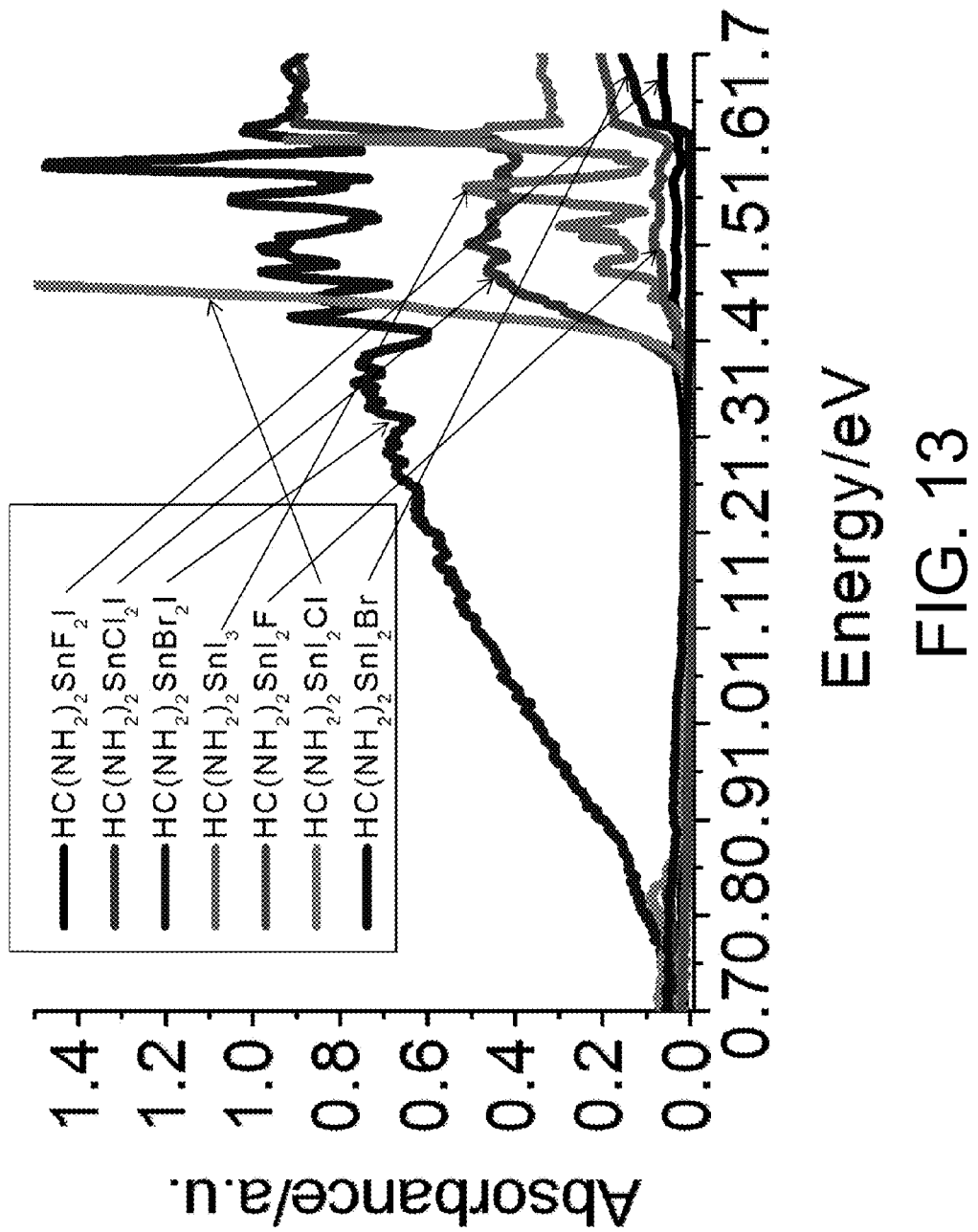
FIG. 13. Optical absorption spectra for $HC(NH_2)_2Sn(I_{3-x}X_x)$ compositions.
Figures 14A, 14B:
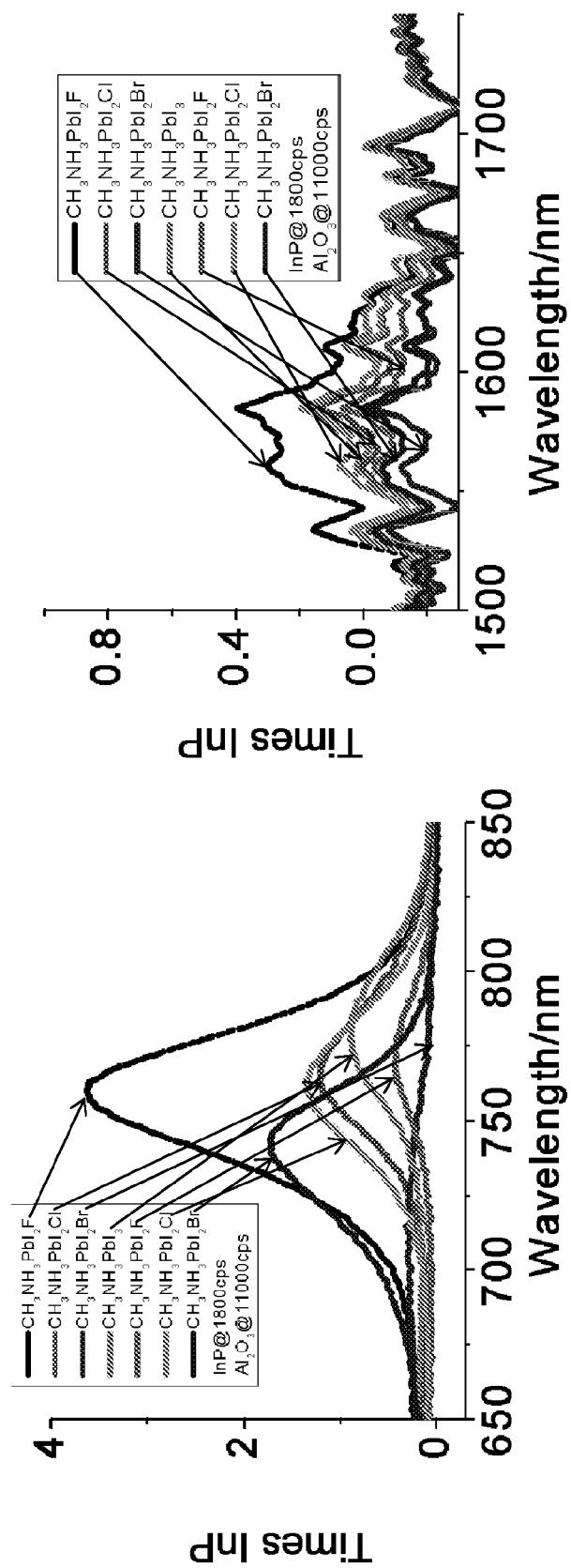
FIG. 14. PL emission vs. wavelength for $CH_3NH_3Pb(I_{3-x}X_x)$ phases, showing a first (A) and a second (B) emission wavelength range.
Figure 15:
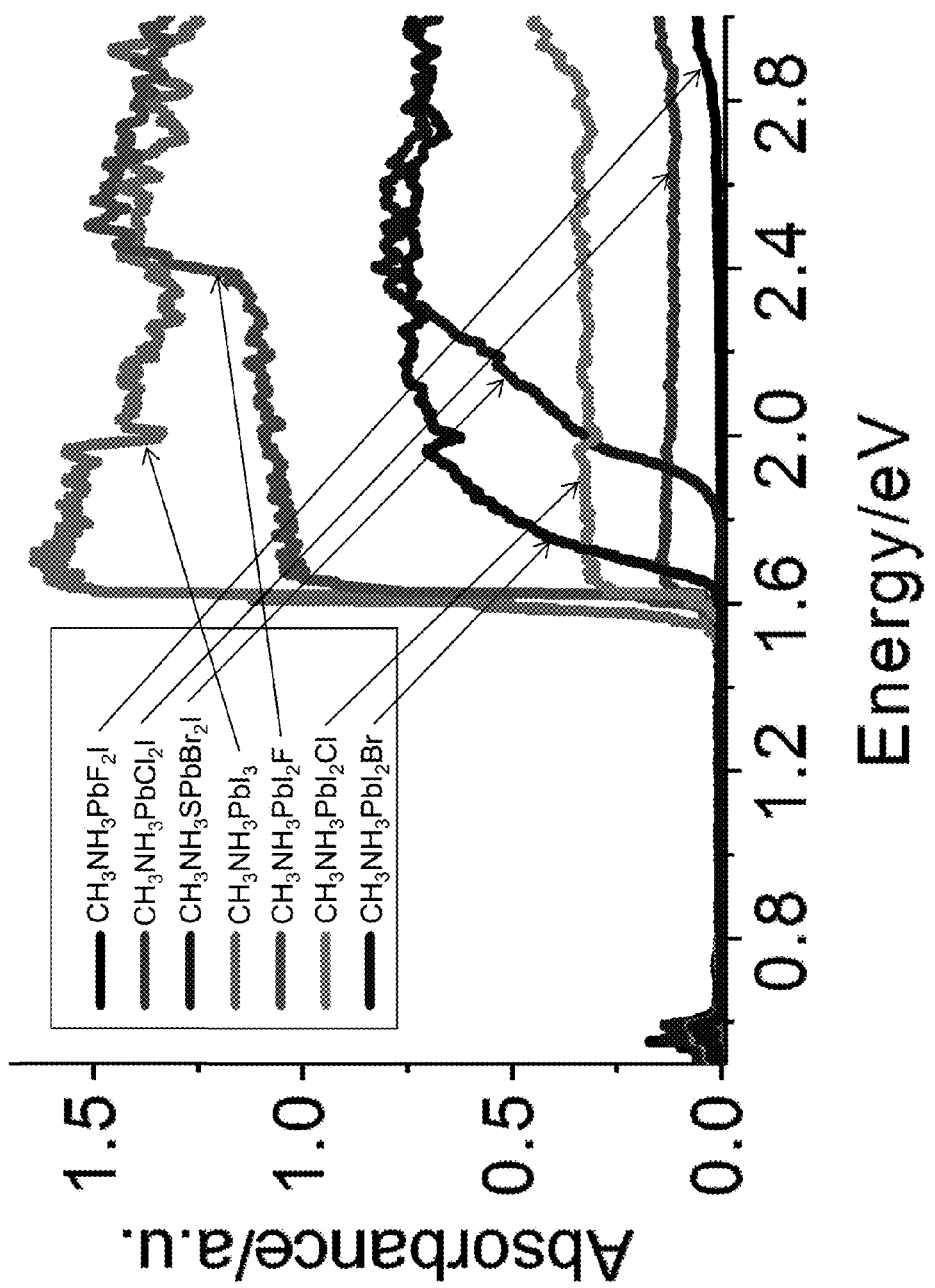
FIG. 15. Optical absorption spectra for $CH_3NH_3Pb(I_{3-x}X_x)$ compositions.
Figure 16:
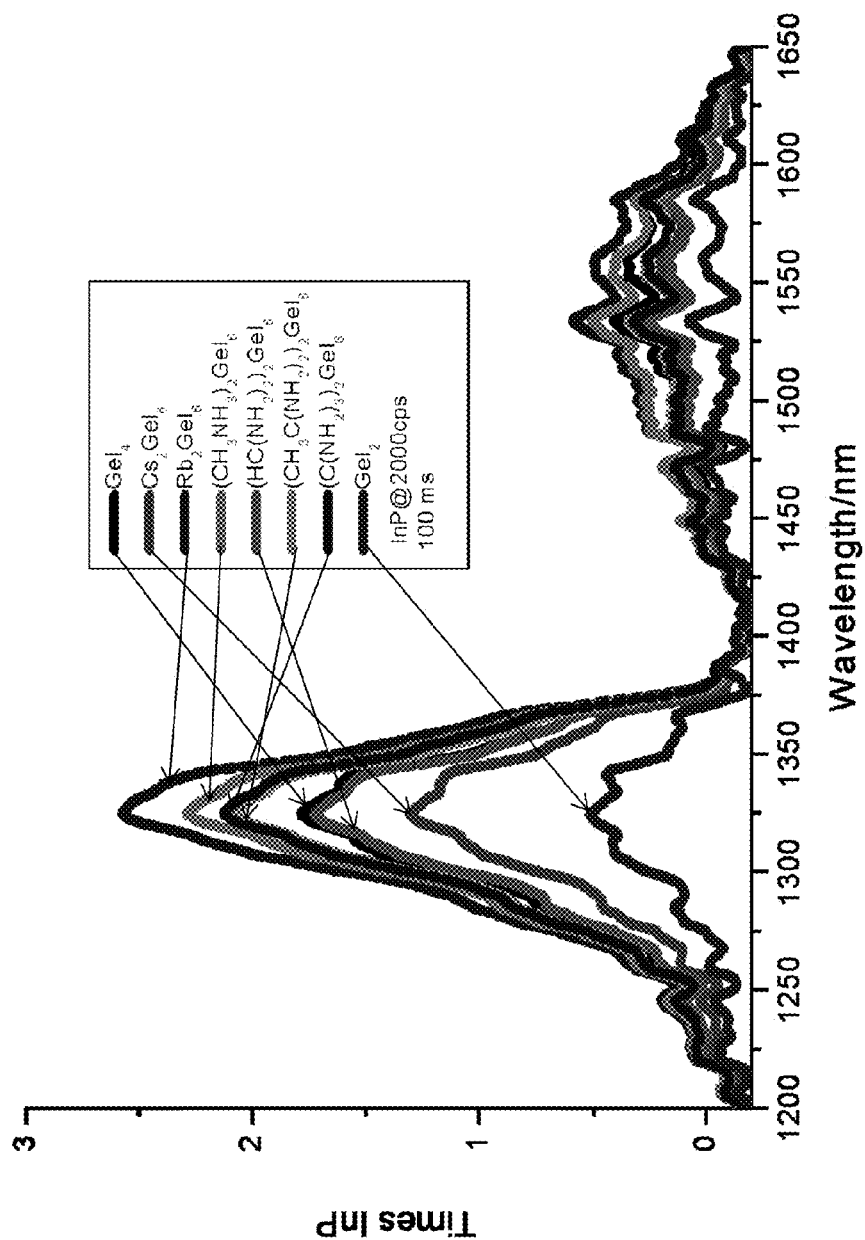
FIG. 16. PL emission vs. wavelength for germanium iodide phases.
Figure 17:
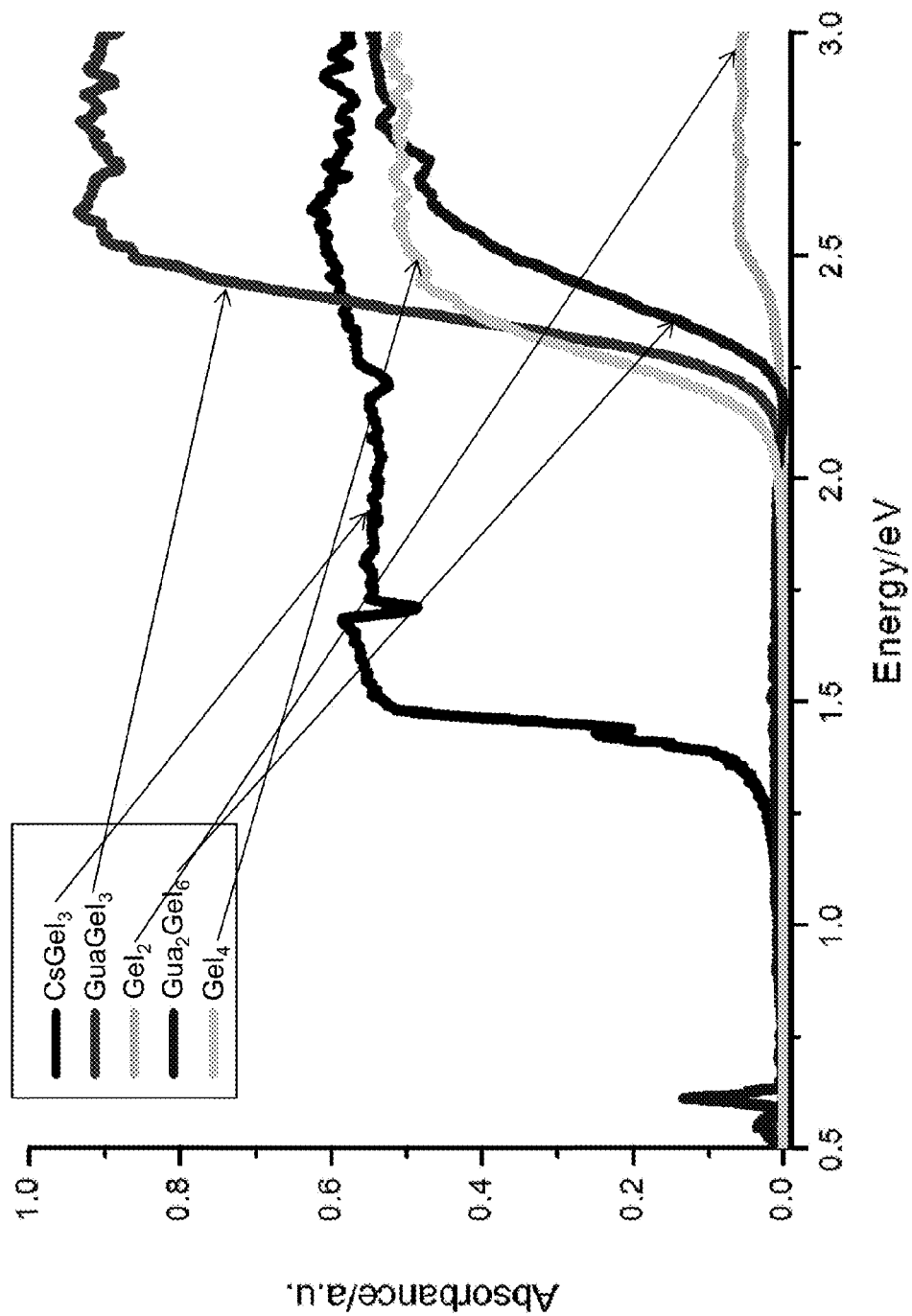
FIG. 17. Optical absorption spectra for germanium iodide phases.
Figure 18:
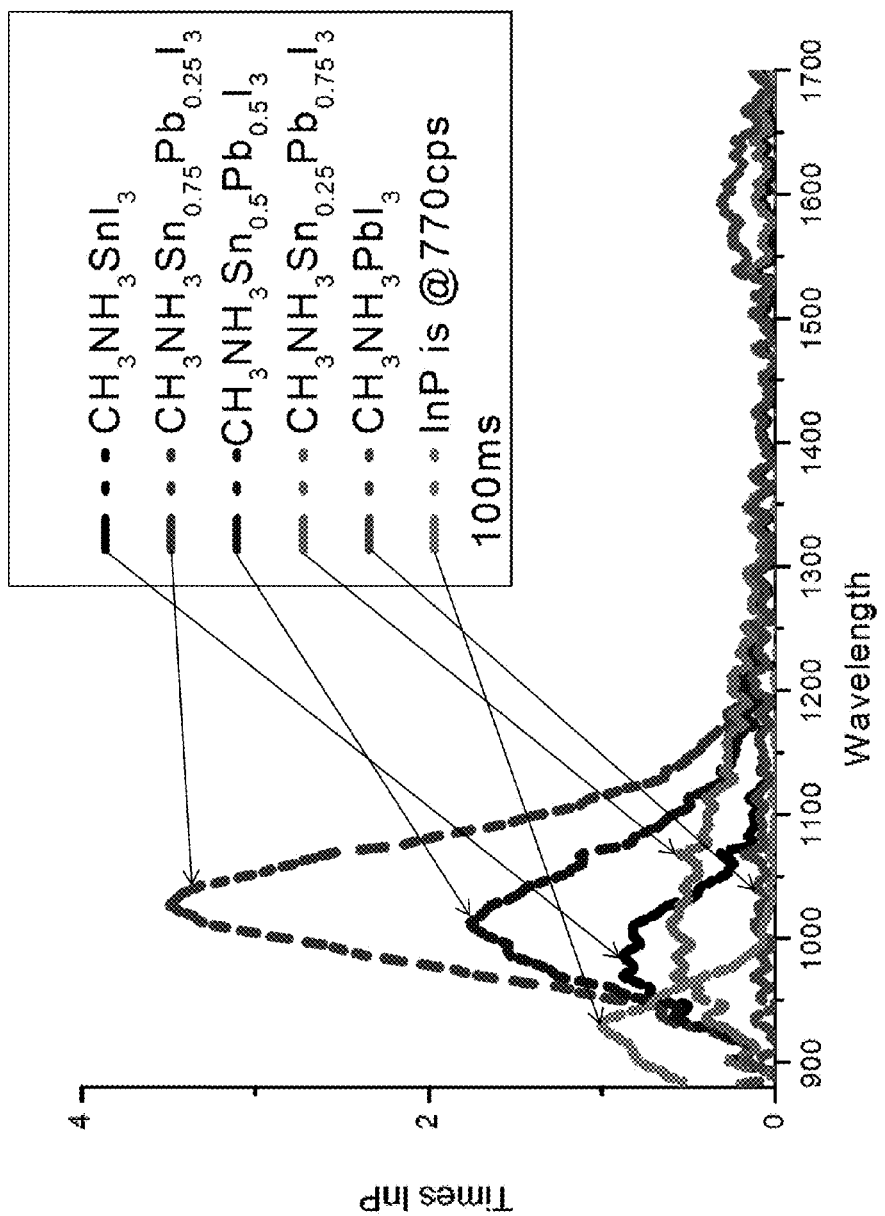
FIG. 18. PL emission vs. wavelength for $CH_3NH_3Sn_{1-x}Pb_xI_3$ for different values of x.
Figure 19:
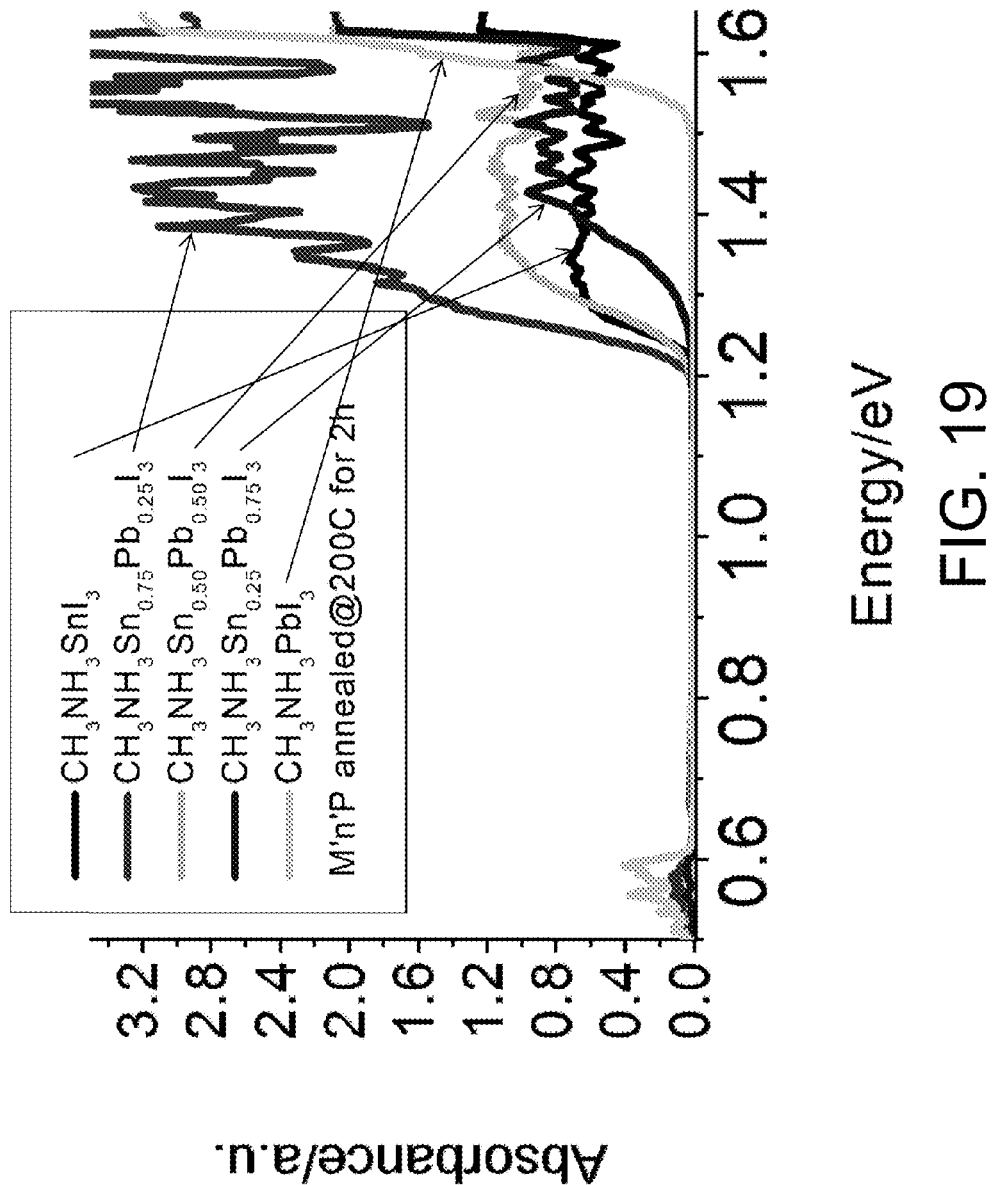
FIG. 19. Optical absorption for $CH_3NH_3Sn_{1-x}Pb_xI_3$ for different values of x.
Figure 20:
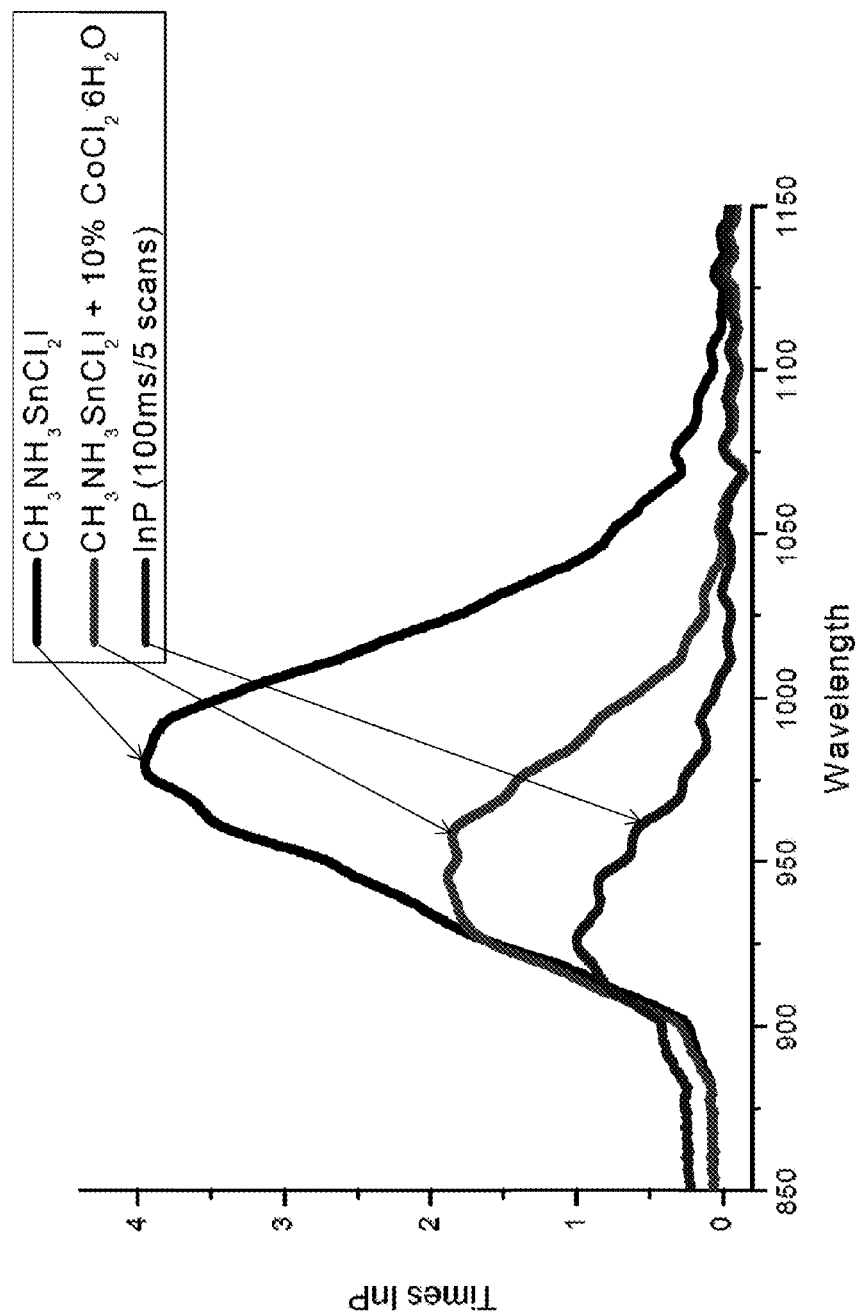
FIG. 20. PL emission vs. wavelength for $CH_3NH_3SnCl_2I$ and $CH_3NH_3Sn_{0.9}Co_{0.1}Cl_2I$.

Provided are compounds having the formula A/M/X, wherein A is at least one element from Group 1 of the periodic table or is an organic cation; M is at least one element from Group 14 of the periodic table; and X is at least one element from Group 17 of the periodic table. Examples of organic cations, A, in A/M/X compounds include methylammonium ($CH_3NH_3^+$), formamidinium ($HC(NH_2)_2^+$), methylformamidinium ($H_3CC(NH_2)_2^+$), guanidinium ($C(NH_2)_3^+$), N,N- alkyl bipyridines and acridine. In some embodiments, the compounds have a formula selected from $AMX_3$, $A_2MX_4$, $AM_2X_5$, $A_2MX_6$ and $AMX_5$.

The compounds can exhibit photoluminescence in the visible and near infrared region at room temperature (RT) (~23° C.).

In some embodiments the A, M, and X atoms are mixed with other congeners, for example, $CsSnI_2Cl$ and $Cs_2SnI_2Cl_2$. In some embodiments, the materials comprise other main group elements, transition metal elements, lanthanide elements, actinide elements, or their compounds, such as $Al_2O_3$, SnO, $SnF_2$ and $CsSn_{0.5}F_3$. In some embodiments, provide enhanced emission intensity or emission wavelengths shifted to a desired spectral range.

Also provided are solution-based thin film deposition processes for making films of the A/M/X compounds. In the processes, thin films can be deposited by spin-coating or spraying solutions on various large-area substrates such as Si, glasses and flexible plastic substrates at low temperatures (e.g., 120-150° C.). Some embodiments of the solution-processed thin films can outperform single crystalline InP:S wafers in terms of their PL intensities.

Synthesis and Characterization of A/M/X Metal Halide Compounds that Emit Photoluminescence in the Visible and Near Infrared Regions.

Classes of metal halide compounds, including those that exhibit emission in the visible and infrared regions, can be categorized into five types.

The class of Type I materials comprises compounds of the formulas $AMX_3$, $A_2M_2X_4$, $AM_2X_5$ and $A_2MX_6$ and either metal oxides of the formula $M'O_{y'}$, where y=1, 1.5 or 2, or metal halides of the formulas $A_2MX_6$ and $A_3MX_6$, where A is selected from at least one of elements of Group 1 or organic cations, M' is selected from at least one of elements of Groups 2-4 or elements of Groups 12-15 and X is an element from Group 17.

The class of Type II includes compounds having organic counterions. This class has two sub-types: Type IIA and Type IIB. In Type IIA compound, 'A' comprises monovalent organic cations, such as methylammonium ($CH_3NH_3^+$), formamidinium ($HC(NH_2)_2^+$), methylformamidinium ($H_3CC(NH_2)_2^+$) and guanidinium ($C(NH_2)_3^+$). In Type IIB compounds, 'A' comprises bulky π-conjugated divalent organic cations, such as N,N-alkyl bipyridines and acridine. The latter compounds typically exhibit emission by a red light excitation at 785 nm.

The class of Type III includes compounds in which 'X' comprises more than one halide atom. Such compounds include $CsSnI_2Cl$ and $CsSnICl_2$.

The class of Type IV includes compounds comprising Ge(IV). Examples of Type IV materials are $GeI_2$, $GeI_4$, $AGeI_5$ and $A_2GeI_6$ (A=alkali metal or organic cations). $GeI_4$ exhibits photoluminescence.

The class of Type V comprises any combination of compounds of Type I, II, III, and/or IV.

The Type I materials typically are black in color. Examples of Type I materials, comprising metal oxides, include a) $(CsSnI_3)_{1-x}(M'O)_x$, M'=Si, Ge, Sn, or Pb; b) $(CsSnI_3)_{1-x}(M'O_{1.5})_x$, M'=B, Al, Ga, In, Sc, or Y; c) $(CsSnI_3)_{1-x}(M'O_2)_x$, M'=Si, Ge, Sn, or Pb; d) $(Cs_2SnI_4)_{1-x}(M'O)_x$, M'=Si, Ge, Sn, or Pb; e) $(Cs_2SnI_4)_{1-x}(M'O_{1.5})_x$, M'=B, Al, Ga, In, Sc, or Y; f) $(Cs_2SnI_4)_{1-x}(M'O_2)_x$, M'=Si, Ge, Sn, or Pb; g) $Cs(SnI_3)_{1-x}(M'O)_x$, M'=Si, Ge, Sn, or Pb; h) $Cs(SnI_3)_{1-x}(M'O_{1.5})_x$, M'=B, Al, Ga, In, Sc, or Y; i) $Cs(SnI_3)_{1-x}(M'O_2)_x$, M'=Si, Ge, Sn, or Pb; j) $Cs_2(SnI_4)_{1-x}(M'O)_x$, M'=Si, Ge, Sn, or Pb; k) $Cs_2(SnI_4)_{1-x}(M'O_{1.5})_x$, M'=B, Al, Ga, In, Sc, or Y; l) $Cs_2(SnI_4)_{1-x}(M'O_2)_x$, M'=Si, Ge, Sn, or Pb, where $0.01 < x < 0.99$.

Examples of specific molar ratios of starting materials that can be used to obtain materials of Type I are shown in Tables a)-l). The amounts of the starting materials in the tables are in mmol.

TABLE a $(CsSnI_3)_{1-x}(M'O)_x$: $0.01 < x < 0.99$, M' = Si, Ge, Sn, or Pb

| x | CsI | $SnI_2$ | PbO | Composition |
|---|---|---|---|---|
| 0 | 1.0 | 1.0 | 0 | $CsSnI_3$ |
| 0.1 | 0.90 | 0.90 | 0.10 | $Cs_{0.9}Sn_{0.9}Pb_{0.1}I_{2.7}O_{0.1}$ |
| 0.2 | 0.80 | 0.80 | 0.20 | $Cs_{0.8}Sn_{0.8}Pb_{0.2}I_{2.4}O_{0.2}$ |
| 0.3 | 0.70 | 0.70 | 0.30 | $Cs_{0.7}Sn_{0.7}Pb_{0.3}I_{2.1}O_{0.3}$ |
| 0.4 | 0.60 | 0.60 | 0.40 | $Cs_{0.6}Sn_{0.6}Pb_{0.4}I_{1.8}O_{0.4}$ |
| 0.5 | 0.50 | 0.50 | 0.50 | $Cs_{0.5}Sn_{0.5}Pb_{0.5}I_{1.5}O_{0.5}$ |

TABLE b $(CsSnI_3)_{1-x}(M'O_{1.5})_x$: $0.01 < x < 0.99$, M' = B, Al, Ga, In, Sc, or Y

| x | CsI | $SnI_2$ | $Al_2O_3$ | Composition |
|---|---|---|---|---|
| 0 | 1.0 | 1.0 | 0 | $CsSnI_3$ |
| 0.1 | 0.90 | 0.90 | 0.05 | $Cs_{0.9}Sn_{0.9}Al_{0.1}I_{2.7}O_{0.15}$ |
| 0.2 | 0.80 | 0.80 | 0.10 | $Cs_{0.8}Sn_{0.8}Al_{0.2}I_{2.4}O_{0.30}$ |
| 0.3 | 0.70 | 0.70 | 0.15 | $Cs_{0.7}Sn_{0.7}Al_{0.3}I_{2.1}O_{0.45}$ |
| 0.4 | 0.60 | 0.60 | 0.20 | $Cs_{0.6}Sn_{0.6}Al_{0.4}I_{1.8}O_{0.60}$ |
| 0.5 | 0.50 | 0.50 | 0.25 | $Cs_{0.5}Sn_{0.5}Al_{0.5}I_{1.5}O_{0.75}$ |

TABLE c $(CsSnI_3)_{1-x}(M'O_2)_x$: $0.01 < x < 0.99$, M' = Si, Ge, Sn, or Pb

| x | CsI | $SnI_2$ | $SiO_2$ | Composition |
|---|---|---|---|---|
| 0 | 1.0 | 1.0 | 0 | $CsSnI_3$ |
| 0.1 | 0.90 | 0.90 | 0.10 | $Cs_{0.9}Sn_{0.9}Si_{0.1}I_{2.7}O_{0.20}$ |
| 0.2 | 0.80 | 0.80 | 0.20 | $Cs_{0.8}Sn_{0.8}Si_{0.2}I_{2.4}O_{0.40}$ |
| 0.3 | 0.70 | 0.70 | 0.30 | $Cs_{0.7}Sn_{0.7}Si_{0.3}I_{2.1}O_{0.60}$ |
| 0.4 | 0.60 | 0.60 | 0.40 | $Cs_{0.6}Sn_{0.6}Si_{0.4}I_{1.8}O_{0.80}$ |
| 0.5 | 0.50 | 0.50 | 0.50 | $Cs_{0.5}Sn_{0.5}Si_{0.5}I_{1.5}O_{1.00}$ |

TABLE d $(Cs_2SnI_4)_{1-x}(M'O)_x$: $0.01 < x < 0.99$, M' = Si, Ge, Sn, or Pb

| x | CsI | $SnI_2$ | PbO | Composition |
|---|---|---|---|---|
| 0 | 2.0 | 1.0 | 0 | $Cs_2SnI_4$ |
| 0.1 | 1.90 | 0.90 | 0.10 | $Cs_{1.9}Sn_{0.9}Pb_{0.1}I_{3.7}O_{0.1}$ |
| 0.2 | 1.80 | 0.80 | 0.20 | $Cs_{1.8}Sn_{0.8}Pb_{0.2}I_{3.4}O_{0.2}$ |
| 0.3 | 1.70 | 0.70 | 0.30 | $Cs_{1.7}Sn_{0.7}Pb_{0.3}I_{3.1}O_{0.3}$ |
| 0.4 | 1.60 | 0.60 | 0.40 | $Cs_{1.6}Sn_{0.6}Pb_{0.4}I_{2.8}O_{0.4}$ |
| 0.5 | 1.50 | 0.50 | 0.50 | $Cs_{1.5}Sn_{0.5}Pb_{0.5}I_{2.5}O_{0.5}$ |

TABLE e $(Cs_2SnI_4)_{1-x}(M'O_{1.5})_x$: $0.01 < x < 0.99$, M' = B, Al, Ga, In, Sc, or Y

| x | CsI | $SnI_2$ | $Al_2O_3$ | Composition |
|---|---|---|---|---|
| 0 | 2.0 | 1.0 | 0 | $Cs_2SnI_4$ |
| 0.1 | 1.90 | 0.90 | 0.05 | $Cs_{1.9}Sn_{0.9}Al_{0.1}I_{3.7}O_{0.15}$ |
| 0.2 | 1.80 | 0.80 | 0.10 | $Cs_{1.8}Sn_{0.8}Al_{0.2}I_{3.4}O_{0.30}$ |
| 0.3 | 1.70 | 0.70 | 0.15 | $Cs_{1.7}Sn_{0.7}Al_{0.3}I_{3.1}O_{0.45}$ |
| 0.4 | 1.60 | 0.60 | 0.20 | $Cs_{1.6}Sn_{0.6}Al_{0.4}I_{2.8}O_{0.60}$ |
| 0.5 | 1.50 | 0.50 | 0.25 | $Cs_{1.5}Sn_{0.5}Al_{0.5}I_{2.5}O_{0.75}$ |

TABLE f $(Cs_2SnI_4)_{1-x}(M'O_2)_x$: $0.01 < x < 0.99$, M' = Si, Ge, Sn, or Pb

| x | CsI | SnI$_2$ | SiO$_2$ | Composition |
|---|-----|---------|---------|-------------|
| 0   | 2.0  | 1.0  | 0    | Cs$_2$SnI$_4$ |
| 0.1 | 1.90 | 0.90 | 0.10 | Cs$_{1.9}$Sn$_{0.9}$Si$_{0.1}$I$_{3.7}$O$_{0.20}$ |
| 0.2 | 1.80 | 0.80 | 0.20 | Cs$_{1.8}$Sn$_{0.8}$Si$_{0.2}$I$_{3.4}$O$_{0.40}$ |
| 0.3 | 1.70 | 0.70 | 0.30 | Cs$_{1.7}$Sn$_{0.7}$Si$_{0.3}$I$_{3.1}$O$_{0.60}$ |
| 0.4 | 1.60 | 0.60 | 0.40 | Cs$_{1.6}$Sn$_{0.6}$Si$_{0.4}$I$_{2.8}$O$_{0.80}$ |
| 0.5 | 1.50 | 0.50 | 0.50 | Cs$_{1.5}$Sn$_{0.5}$Si$_{0.5}$I$_{2.5}$O$_{1.00}$ |

TABLE g $Cs(SnI_3)_{1-x}(M'O)_x$: $0.01 < x < 0.99$, M' = Si, Ge, Sn, or Pb

| x | CsI | SnI$_2$ | PbO | Composition |
|---|-----|---------|-----|-------------|
| 0   | 1.0 | 1.0  | 0    | CsSnI$_3$ |
| 0.1 | 1.0 | 0.90 | 0.10 | CsSn$_{0.9}$Pb$_{0.1}$I$_{2.8}$O$_{0.1}$ |
| 0.2 | 1.0 | 0.80 | 0.20 | CsSn$_{0.8}$Pb$_{0.2}$I$_{2.6}$O$_{0.2}$ |
| 0.3 | 1.0 | 0.70 | 0.30 | CsSn$_{0.7}$Pb$_{0.3}$I$_{2.4}$O$_{0.3}$ |
| 0.4 | 1.0 | 0.60 | 0.40 | CsSn$_{0.6}$Pb$_{0.4}$I$_{2.2}$O$_{0.4}$ |
| 0.5 | 1.0 | 0.50 | 0.50 | CsSn$_{0.5}$Pb$_{0.5}$I$_{2.0}$O$_{0.5}$ |

TABLE h $Cs(SnI_3)_{1-x}(M'O_{1.5})_x$: $0.01 < x < 0.99$, M' = B, Al, Ga, In, Sc, or Y

| x | CsI | SnI$_2$ | Al$_2$O$_3$ | Composition |
|---|-----|---------|-------------|-------------|
| 0   | 1.0 | 1.0  | 0    | CsSnI$_3$ |
| 0.1 | 1.0 | 0.90 | 0.05 | CsSn$_{0.9}$Al$_{0.1}$I$_{2.8}$O$_{0.15}$ |
| 0.2 | 1.0 | 0.80 | 0.10 | CsSn$_{0.8}$Al$_{0.2}$I$_{2.6}$O$_{0.30}$ |
| 0.3 | 1.0 | 0.70 | 0.15 | CsSn$_{0.7}$Al$_{0.3}$I$_{2.4}$O$_{0.45}$ |
| 0.4 | 1.0 | 0.60 | 0.20 | CsSn$_{0.6}$Al$_{0.4}$I$_{2.2}$O$_{0.60}$ |
| 0.5 | 1.0 | 0.50 | 0.25 | CsSn$_{0.5}$Al$_{0.5}$I$_{2.0}$O$_{0.75}$ |

TABLE i $Cs(SnI_3)_{1-x}(M'O_2)_x$: $0.01 < x < 0.99$, M' = Si, Ge, Sn, or Pb

| x | CsI | SnI$_2$ | SiO$_2$ | Composition |
|---|-----|---------|---------|-------------|
| 0   | 1.0 | 1.0  | 0    | CsSnI$_3$ |
| 0.1 | 1.0 | 0.90 | 0.10 | CsSn$_{0.9}$Si$_{0.1}$I$_{2.8}$O$_{0.20}$ |
| 0.2 | 1.0 | 0.80 | 0.20 | CsSn$_{0.8}$Si$_{0.2}$I$_{2.6}$O$_{0.40}$ |
| 0.3 | 1.0 | 0.70 | 0.30 | CsSn$_{0.7}$Si$_{0.3}$I$_{2.4}$O$_{0.60}$ |
| 0.4 | 1.0 | 0.60 | 0.40 | CsSn$_{0.6}$Si$_{0.4}$I$_{2.2}$O$_{0.80}$ |
| 0.5 | 1.0 | 0.50 | 0.50 | CsSn$_{0.5}$Si$_{0.5}$I$_{2.0}$O$_{1.00}$ |

TABLE j $Cs_2(SnI_4)_{1-x}(M'O)_x$: $0.01 < x < 0.99$, M' = Si, Ge, Sn, or Pb

| x | CsI | SnI$_2$ | PbO | Composition |
|---|-----|---------|-----|-------------|
| 0   | 2.0 | 1.0  | 0    | Cs$_2$SnI$_4$ |
| 0.1 | 2.0 | 0.90 | 0.10 | Cs$_2$Sn$_{0.9}$Pb$_{0.1}$I$_{3.8}$O$_{0.1}$ |
| 0.2 | 2.0 | 0.80 | 0.20 | Cs$_2$Sn$_{0.8}$Pb$_{0.2}$I$_{3.6}$O$_{0.2}$ |
| 0.3 | 2.0 | 0.70 | 0.30 | Cs$_2$Sn$_{0.7}$Pb$_{0.3}$I$_{3.4}$O$_{0.3}$ |
| 0.4 | 2.0 | 0.60 | 0.40 | Cs$_2$Sn$_{0.6}$Pb$_{0.4}$I$_{3.2}$O$_{0.4}$ |
| 0.5 | 2.0 | 0.50 | 0.50 | Cs$_2$Sn$_{0.5}$Pb$_{0.5}$I$_{3.0}$O$_{0.5}$ |

TABLE k $Cs_2(SnI_4)_{1-x}(M'O_{1.5})_x$: $0.01 < x < 0.99$, M' = B, Al, Ga, In, Sc, or Y

| x | CsI | SnI$_2$ | Al$_2$O$_3$ | Composition |
|---|-----|---------|-------------|-------------|
| 0   | 2.0 | 1.0  | 0    | Cs$_2$SnI$_4$ |
| 0.1 | 2.0 | 0.90 | 0.05 | Cs$_2$Sn$_{0.9}$Al$_{0.1}$I$_{3.8}$O$_{0.15}$ |
| 0.2 | 2.0 | 0.80 | 0.10 | Cs$_2$Sn$_{0.8}$Al$_{0.2}$I$_{3.6}$O$_{0.30}$ |
| 0.3 | 2.0 | 0.70 | 0.15 | Cs$_2$Sn$_{0.7}$Al$_{0.3}$I$_{3.4}$O$_{0.45}$ |
| 0.4 | 2.0 | 0.60 | 0.20 | Cs$_2$Sn$_{0.6}$Al$_{0.4}$I$_{3.2}$O$_{0.60}$ |
| 0.5 | 2.0 | 0.50 | 0.25 | Cs$_2$Sn$_{0.5}$Al$_{0.5}$I$_{3.0}$O$_{0.75}$ |

TABLE l $Cs_2(SnI_4)_{1-x}(M'O_2)_x$: $0.01 < x < 0.99$, M' = Si, Ge, Sn, or Pb

| x | CsI | SnI$_2$ | SiO$_2$ | Composition |
|---|-----|---------|---------|-------------|
| 0   | 2.0 | 1.0  | 0    | Cs$_2$SnI$_4$ |
| 0.1 | 2.0 | 0.90 | 0.10 | Cs$_2$Sn$_{0.9}$Si$_{0.1}$I$_{3.8}$O$_{0.20}$ |
| 0.2 | 2.0 | 0.80 | 0.20 | Cs$_2$Sn$_{0.8}$Si$_{0.2}$I$_{3.6}$O$_{0.40}$ |
| 0.3 | 2.0 | 0.70 | 0.30 | Cs$_2$Sn$_{0.7}$Si$_{0.3}$I$_{3.4}$O$_{0.60}$ |
| 0.4 | 2.0 | 0.60 | 0.40 | Cs$_2$Sn$_{0.6}$Si$_{0.4}$I$_{3.2}$O$_{0.80}$ |
| 0.5 | 2.0 | 0.50 | 0.50 | Cs$_2$Sn$_{0.5}$Si$_{0.5}$I$_{3.0}$O$_{1.00}$ |

Examples of Type I materials comprising metal halides are m) $(CsSnI_3)_{1-x}(Cs_{1.5}M_{0.5}F_3)_x$, M'=Al, Ga, In, Sc, or Y; p) $(CsSnI_3)_{1-x}(CsM'_{0.5}F_3)_x$, M'=Si, Ge, Sn, Ti, Zr, or Hf; q) $(Cs_2SnI_4)_{1-x}(Cs_{1.5}M'_{0.5}F_3)_x$, M'=Al, Ga, In, Sc, or Y; t) $(Cs_2SnI_4)_{1-x}(CsM'_{0.5}F_3)_x$, M'=Si, Ge, Sn, Ti, Zr, or Hf; u) $Cs(SnI_3)_{1-x}(Cs_{1.5}M'_{0.5}F_3)_x$, M'=Al, Ga, In, Sc, or Y; x) $Cs(SnI_3)_{1-x}(CsM'_{0.5}F_3)_x$, M'=Si, Ge, Sn, Ti, Zr, or Hf; where $0.01<x<0.99$. Examples of specific molar ratios of starting materials that can be used to obtain these Type I materials are shown in Tables m, p, q, t, u, and x. The amounts of the starting materials in the tables are in mmol.

Tables n, r, and y list specific molar ratios of starting materials that can be used to obtain materials comprising compounds of the formula AMX$_3$ or A$_2$MX$_4$ and metal halides of the formula MF$_6$. Tables o, s, and w list specific molar ratios of starting materials that can be used to obtain materials comprising compounds of the formula AMX$_3$ or A$_2$MX$_4$ and metal halides of the formula AMF$_6$. Tables y, z, and aa list specific molar ratios for starting materials that can be used to obtain materials comprising SnI$_2$ compounds and metal halides of the formula A$_2$MX$_6$, AMX$_6$, or MX$_6$.

Mixed Heteroatom Fluoride Compositions (1.0 mmol basis)

TABLE m $(CsSnI_3)_{1-x}(Cs_{1.5}M'_{0.5}F_3)_x$: $0.01 < x < 0.99$, M' = Al, Ga, In, Sc, or Y

| x | CsI | SnI$_2$ | AlF$_3$ | CsF | Composition |
|---|-----|---------|---------|-----|-------------|
| 0   | 1.0  | 1.0  | 0    | 0    | CsSnI$_3$ |
| 0.1 | 0.90 | 0.90 | 0.05 | 0.15 | Cs$_{1.05}$Sn$_{0.9}$Al$_{0.05}$I$_{2.7}$F$_{0.3}$ |
| 0.2 | 0.80 | 0.80 | 0.10 | 0.30 | Cs$_{1.10}$Sn$_{0.8}$Al$_{0.10}$I$_{2.4}$F$_{0.6}$ |
| 0.3 | 0.70 | 0.70 | 0.15 | 0.45 | Cs$_{1.15}$Sn$_{0.7}$Al$_{0.15}$I$_{2.1}$F$_{0.9}$ |
| 0.4 | 0.60 | 0.60 | 0.20 | 0.60 | Cs$_{1.20}$Sn$_{0.6}$Al$_{0.20}$I$_{1.8}$F$_{1.2}$ |
| 0.5 | 0.50 | 0.50 | 0.25 | 0.75 | Cs$_{1.25}$Sn$_{0.5}$Al$_{0.25}$I$_{1.5}$F$_{1.5}$ |

TABLE n $(CsSnI_3)_{1-x}(Cs_0M'_{0.5}F_3)_x$: $0.01 < x < 0.99$, M' = Al

| x | CsI | SnI$_2$ | AlF$_3$ | Composition |
|---|-----|---------|---------|-------------|
| 0   | 1.0  | 1.0  | 0    | CsSnI$_3$ |
| 0.1 | 0.90 | 0.90 | 0.10 | Cs$_{0.9}$Sn$_{0.9}$Al$_{0.10}$I$_{2.7}$F$_{0.3}$ |
| 0.2 | 0.80 | 0.80 | 0.20 | Cs$_{0.8}$Sn$_{0.8}$Al$_{0.20}$I$_{2.4}$F$_{0.6}$ |
| 0.3 | 0.70 | 0.70 | 0.30 | Cs$_{0.7}$Sn$_{0.7}$Al$_{0.30}$I$_{2.1}$F$_{0.9}$ |
| 0.4 | 0.60 | 0.60 | 0.40 | Cs$_{0.6}$Sn$_{0.6}$Al$_{0.40}$I$_{1.8}$F$_{1.2}$ |
| 0.5 | 0.50 | 0.50 | 0.50 | Cs$_{0.5}$Sn$_{0.5}$Al$_{0.50}$I$_{1.5}$F$_{1.5}$ |

TABLE o $(CsSnI_3)_{1-x}(Cs_{0.5}M'_{0.5}F_3)_x$: $0.01 < x < 0.99$, M' = P, As, Sb, V, Nb, or Ta

| x | CsI | SnI$_2$ | CsPF$_6$ | Composition |
|---|-----|---------|----------|-------------|
| 0   | 1.0  | 1.0  | 0    | CsSnI$_3$ |
| 0.1 | 0.90 | 0.90 | 0.05 | Cs$_{0.95}$Sn$_{0.9}$P$_{0.05}$I$_{2.7}$F$_{0.3}$ |
| 0.2 | 0.80 | 0.80 | 0.10 | Cs$_{0.90}$Sn$_{0.8}$P$_{0.10}$I$_{2.4}$F$_{0.6}$ |
| 0.3 | 0.70 | 0.70 | 0.15 | Cs$_{0.85}$Sn$_{0.7}$P$_{0.15}$I$_{2.1}$F$_{0.9}$ |
| 0.4 | 0.60 | 0.60 | 0.20 | Cs$_{0.80}$Sn$_{0.6}$P$_{0.20}$I$_{1.8}$F$_{1.2}$ |
| 0.5 | 0.50 | 0.50 | 0.25 | Cs$_{0.75}$Sn$_{0.5}$P$_{0.25}$I$_{1.5}$F$_{1.5}$ |

TABLE p $(CsSnI_3)_{1-x}(CsM'_{0.5}F_3)_x$: $0.01 < x < 0.99$, M' = Si, Ge, Sn, Ti, Zr, or Hf

| x | CsI | SnI$_2$ | Cs$_2$SiF$_6$ | Composition |
|---|-----|---------|---------------|-------------|
| 0   | 1.0  | 1.0  | 0    | CsSnI$_3$ |
| 0.1 | 0.90 | 0.90 | 0.05 | CsSn$_{0.9}$Si$_{0.05}$I$_{2.7}$F$_{0.3}$ |
| 0.2 | 0.80 | 0.80 | 0.10 | CsSn$_{0.8}$Si$_{0.10}$I$_{2.4}$F$_{0.6}$ |
| 0.3 | 0.70 | 0.70 | 0.15 | CsSn$_{0.7}$Si$_{0.15}$I$_{2.1}$F$_{0.9}$ |
| 0.4 | 0.60 | 0.60 | 0.20 | CsSn$_{0.6}$Si$_{0.20}$I$_{1.8}$F$_{1.2}$ |
| 0.5 | 0.50 | 0.50 | 0.25 | CsSn$_{0.5}$Si$_{0.25}$I$_{1.5}$F$_{1.5}$ |

TABLE q $(Cs_2SnI_4)_{1-x}(Cs_{1.5}M'_{0.5}F_3)_x$: $0.01 < x < 0.99$, M' = Al, Ga, In, Sc, or Y

| x | CsI | SnI$_2$ | AlF$_3$ | CsF | Composition |
|---|-----|---------|---------|-----|-------------|
| 0   | 2.0  | 1.0  | 0    | 0    | Cs$_2$SnI$_4$ |
| 0.1 | 1.80 | 0.90 | 0.05 | 0.15 | Cs$_{1.95}$Sn$_{0.9}$Al$_{0.05}$I$_{3.7}$F$_{0.3}$ |
| 0.2 | 1.60 | 0.80 | 0.10 | 0.30 | Cs$_{1.90}$Sn$_{0.8}$Al$_{0.10}$I$_{3.4}$F$_{0.6}$ |
| 0.3 | 1.40 | 0.70 | 0.15 | 0.45 | Cs$_{1.85}$Sn$_{0.7}$Al$_{0.15}$I$_{3.1}$F$_{0.9}$ |
| 0.4 | 1.20 | 0.60 | 0.20 | 0.60 | Cs$_{1.80}$Sn$_{0.6}$Al$_{0.20}$I$_{2.8}$F$_{1.2}$ |
| 0.5 | 1.00 | 0.50 | 0.25 | 0.75 | Cs$_{1.75}$Sn$_{0.5}$Al$_{0.25}$I$_{2.5}$F$_{1.5}$ |

TABLE r $(Cs_2SnI_4)_{1-x}(Cs_0M'_{0.5}F_3)_x$: $0.01 < x < 0.99$, M' = Al

| x | CsI | SnI$_2$ | AlF$_3$ | Composition |
|---|-----|---------|---------|-------------|
| 0   | 2.0  | 1.0  | 0    | Cs$_2$SnI$_4$ |
| 0.1 | 1.80 | 0.90 | 0.10 | Cs$_{1.8}$Sn$_{0.9}$Al$_{0.10}$I$_{3.6}$F$_{0.3}$ |
| 0.2 | 1.60 | 0.80 | 0.20 | Cs$_{1.6}$Sn$_{0.8}$Al$_{0.20}$I$_{3.2}$F$_{0.6}$ |
| 0.3 | 1.40 | 0.70 | 0.30 | Cs$_{1.4}$Sn$_{0.7}$Al$_{0.30}$I$_{2.8}$F$_{0.9}$ |
| 0.4 | 1.20 | 0.60 | 0.40 | Cs$_{1.2}$Sn$_{0.6}$Al$_{0.40}$I$_{2.4}$F$_{1.2}$ |
| 0.5 | 1.00 | 0.50 | 0.50 | Cs$_{1.0}$Sn$_{0.5}$Al$_{0.50}$I$_{2.0}$F$_{1.5}$ |

TABLE s $(Cs_2SnI_4)_{1-x}(Cs_{0.5}M'_{0.5}F_3)_x$: $0.01 < x < 0.99$, M' = P, As, Sb, V, Nb, or Ta

| x | CsI | SnI$_2$ | CsPF$_6$ | Composition |
|---|-----|---------|----------|-------------|
| 0   | 2.0  | 1.0  | 0    | Cs$_2$SnI$_4$ |
| 0.1 | 1.80 | 0.90 | 0.05 | Cs$_{1.95}$Sn$_{0.9}$P$_{0.05}$I$_{3.7}$F$_{0.3}$ |
| 0.2 | 1.60 | 0.80 | 0.10 | Cs$_{1.90}$Sn$_{0.8}$P$_{0.10}$I$_{3.4}$F$_{0.6}$ |
| 0.3 | 1.40 | 0.70 | 0.15 | Cs$_{1.85}$Sn$_{0.7}$P$_{0.15}$I$_{3.1}$F$_{0.9}$ |
| 0.4 | 1.20 | 0.60 | 0.20 | Cs$_{1.80}$Sn$_{0.6}$P$_{0.20}$I$_{2.8}$F$_{1.2}$ |
| 0.5 | 1.00 | 0.50 | 0.25 | Cs$_{1.75}$Sn$_{0.5}$P$_{0.25}$I$_{2.5}$F$_{1.5}$ |

TABLE t $(Cs_2SnI_4)_{1-x}(CsM'_{0.5}F_3)_x$: $0.01 < x < 0.99$, M' = Si, Ge, Sn, Ti, Zr, or Hf

| x | CsI | SnI$_2$ | Cs$_2$SiF$_6$ | Composition |
|---|-----|---------|---------------|-------------|
| 0   | 2.0  | 1.0  | 0    | Cs$_2$SnI$_4$ |
| 0.1 | 1.80 | 0.90 | 0.05 | Cs$_{1.8}$Sn$_{0.9}$Si$_{0.05}$I$_{3.7}$F$_{0.3}$ |
| 0.2 | 1.60 | 0.80 | 0.10 | Cs$_{1.6}$Sn$_{0.8}$Si$_{0.10}$I$_{3.4}$F$_{0.6}$ |
| 0.3 | 1.40 | 0.70 | 0.15 | Cs$_{1.4}$Sn$_{0.7}$Si$_{0.15}$I$_{3.1}$F$_{0.9}$ |
| 0.4 | 1.20 | 0.60 | 0.20 | Cs$_{1.2}$Sn$_{0.6}$Si$_{0.20}$I$_{2.8}$F$_{1.2}$ |
| 0.5 | 1.00 | 0.50 | 0.25 | Cs$_{1.0}$Sn$_{0.5}$Si$_{0.25}$I$_{2.5}$F$_{1.5}$ |

TABLE u $Cs(SnI_3)_{1-x}(Cs_{1.5}M'_{0.5}F_3)_x$: $0.01 < x < 0.99$, M' = Al, Ga, In, Sc, or Y

| x | CsI | SnI$_2$ | AlF$_3$ | CsF | Composition |
|---|-----|---------|---------|-----|-------------|
| 0   | 1.0 | 1.0  | 0    | 0    | CsSnI$_3$ |
| 0.1 | 1.0 | 0.90 | 0.05 | 0.15 | Cs$_{1.15}$Sn$_{0.9}$Al$_{0.05}$I$_{2.8}$F$_{0.3}$ |
| 0.2 | 1.0 | 0.80 | 0.10 | 0.30 | Cs$_{1.30}$Sn$_{0.8}$Al$_{0.10}$I$_{2.6}$F$_{0.6}$ |
| 0.3 | 1.0 | 0.70 | 0.15 | 0.45 | Cs$_{1.45}$Sn$_{0.7}$Al$_{0.15}$I$_{2.4}$F$_{0.9}$ |
| 0.4 | 1.0 | 0.60 | 0.20 | 0.60 | Cs$_{1.60}$Sn$_{0.6}$Al$_{0.20}$I$_{2.2}$F$_{1.2}$ |
| 0.5 | 1.0 | 0.50 | 0.25 | 0.75 | Cs$_{1.75}$Sn$_{0.5}$Al$_{0.25}$I$_{2.0}$F$_{1.5}$ |

TABLE v $Cs(SnI_3)_{1-x}(Cs_0M'_{0.5}F_3)_x$: $0.01 < x < 0.99$, M' = Al

| x | CsI | SnI$_2$ | AlF$_3$ | Composition |
|---|-----|---------|---------|-------------|
| 0   | 1.0 | 1.0  | 0    | CsSnI$_3$ |
| 0.1 | 1.0 | 0.90 | 0.10 | CsSn$_{0.9}$Al$_{0.10}$I$_{2.8}$F$_{0.3}$ |
| 0.2 | 1.0 | 0.80 | 0.20 | CsSn$_{0.8}$Al$_{0.20}$I$_{2.6}$F$_{0.6}$ |
| 0.3 | 1.0 | 0.70 | 0.30 | CsSn$_{0.7}$Al$_{0.30}$I$_{2.4}$F$_{0.9}$ |
| 0.4 | 1.0 | 0.60 | 0.40 | CsSn$_{0.6}$Al$_{0.40}$I$_{2.2}$F$_{1.2}$ |
| 0.5 | 1.0 | 0.50 | 0.50 | CsSn$_{0.5}$Al$_{0.50}$I$_{2.0}$F$_{1.5}$ |

TABLE w $Cs(SnI_3)_{1-x}(Cs_{0.5}M'_{0.5}F_3)_x$: $0.01 < x < 0.99$, M' = P, As, Sb, V, Nb, or Ta

| x | CsI | SnI$_2$ | CsPF$_6$ | Composition |
|---|-----|---------|----------|-------------|
| 0   | 1.0 | 1.0  | 0    | CsSnI$_3$ |
| 0.1 | 1.0 | 0.90 | 0.05 | Cs$_{1.05}$Sn$_{0.9}$P$_{0.05}$I$_{2.8}$F$_{0.3}$ |
| 0.2 | 1.0 | 0.80 | 0.10 | Cs$_{1.10}$Sn$_{0.8}$P$_{0.10}$I$_{2.6}$F$_{0.6}$ |
| 0.3 | 1.0 | 0.70 | 0.15 | Cs$_{1.15}$Sn$_{0.7}$P$_{0.15}$I$_{2.4}$F$_{0.9}$ |
| 0.4 | 1.0 | 0.60 | 0.20 | Cs$_{1.20}$Sn$_{0.6}$P$_{0.20}$I$_{2.2}$F$_{1.2}$ |
| 0.5 | 1.0 | 0.50 | 0.25 | Cs$_{1.25}$Sn$_{0.5}$P$_{0.25}$I$_{2.0}$F$_{1.5}$ |

TABLE x $Cs(SnI_3)_{1-x}(CsM'_{0.5}F_3)_x$: 0.01 < x < 0.99,
M' = Si, Ge, Sn, Ti, Zr, or Hf

| x | CsI | $SnI_2$ | $Cs_2SiF_6$ | Composition |
|---|---|---|---|---|
| 0 | 1.0 | 1.0 | 0 | $CsSnI_3$ |
| 0.1 | 1.0 | 0.90 | 0.05 | $Cs_{1.10}Sn_{0.9}Si_{0.05}I_{2.8}F_{0.3}$ |
| 0.2 | 1.0 | 0.80 | 0.10 | $Cs_{1.20}Sn_{0.8}Si_{0.10}I_{2.6}F_{0.6}$ |
| 0.3 | 1.0 | 0.70 | 0.15 | $Cs_{1.30}Sn_{0.7}Si_{0.15}I_{2.4}F_{0.9}$ |
| 0.4 | 1.0 | 0.60 | 0.20 | $Cs_{1.40}Sn_{0.6}Si_{0.20}I_{2.2}F_{1.2}$ |
| 0.5 | 1.0 | 0.50 | 0.25 | $Cs_{1.50}Sn_{0.5}Si_{0.25}I_{2.0}F_{1.5}$ |

TABLE y $(SnI_2)_{1-x}(Cs_{1.5}M'_{0.5}F_3)_x$: 0.01 < x < 0.99,
M' = Al, Ga, In, Sc, or Y

| x | CsI | $SnI_2$ | $AlF_3$ | CsF | Composition |
|---|---|---|---|---|---|
| 0 | 0 | 1.0 | 0 | 0 | $SnI_2$ |
| 0.1 | 0 | 0.90 | 0.05 | 0.15 | $Cs_{0.15}Sn_{0.9}Al_{0.05}I_{1.0}F_{0.3}$ |
| 0.2 | 0 | 0.80 | 0.10 | 0.30 | $Cs_{0.30}Sn_{0.8}Al_{0.10}I_{1.6}F_{0.6}$ |
| 0.3 | 0 | 0.70 | 0.15 | 0.45 | $Cs_{0.45}Sn_{0.7}Al_{0.15}I_{1.4}F_{0.9}$ |
| 0.4 | 0 | 0.60 | 0.20 | 0.60 | $Cs_{0.60}Sn_{0.6}Al_{0.20}I_{1.2}F_{1.2}$ |
| 0.5 | 0 | 0.50 | 0.25 | 0.75 | $Cs_{0.75}Sn_{0.5}Al_{0.25}I_{1.0}F_{1.5}$ |

TABLE z $(SnI_2)_{1-x}(Cs_{0.5}M'_{0.5}F_3)_x$: 0.01 < x < 0.99, M' =
P, As, Sb, V, Nb, or Ta

| x | CsI | $SnI_2$ | $CsPF_6$ | Composition |
|---|---|---|---|---|
| 0 | 0 | 1.0 | 0 | $SnI_2$ |
| 0.1 | 0 | 0.90 | 0.05 | $Cs_{0.05}Sn_{0.9}P_{0.05}I_{1.8}F_{0.3}$ |
| 0.2 | 0 | 0.80 | 0.10 | $Cs_{0.10}Sn_{0.8}P_{0.10}I_{1.6}F_{0.6}$ |
| 0.3 | 0 | 0.70 | 0.15 | $Cs_{0.15}Sn_{0.7}P_{0.15}I_{1.4}F_{0.9}$ |
| 0.4 | 0 | 0.60 | 0.20 | $Cs_{0.20}Sn_{0.6}P_{0.20}I_{1.2}F_{1.2}$ |
| 0.5 | 0 | 0.50 | 0.25 | $Cs_{0.25}Sn_{0.5}P_{0.25}I_{1.0}F_{1.5}$ |

TABLE aa $(SnI_2)_{1-x}(CsM'_{0.5}F_3)_x$: 0.01 < x < 0.99,
M' = Si, Ge, Sn, Ti, Zr, or Hf

| x | CsI | $SnI_2$ | $Cs_2SiF_6$ | Composition |
|---|---|---|---|---|
| 0 | 0 | 1.0 | 0 | $SnI_2$ |
| 0.1 | 0 | 0.90 | 0.05 | $Cs_{0.10}Sn_{0.9}Si_{0.05}I_{1.8}F_{0.3}$ |
| 0.2 | 0 | 0.80 | 0.10 | $Cs_{0.20}Sn_{0.8}Si_{0.10}I_{1.6}F_{0.6}$ |
| 0.3 | 0 | 0.70 | 0.15 | $Cs_{0.30}Sn_{0.7}Si_{0.15}I_{1.4}F_{0.9}$ |
| 0.4 | 0 | 0.60 | 0.20 | $Cs_{0.40}Sn_{0.6}Si_{0.20}I_{1.2}F_{1.2}$ |
| 0.5 | 0 | 0.50 | 0.25 | $Cs_{0.50}Sn_{0.5}Si_{0.25}I_{1.0}F_{1.5}$ |

Examples of Type IIA materials that include monovalent organic countercations include ab) $CH_3NH_3MI_3$, M=Ge, Sn, or Pb; ac) $HC(NH_2)_2MI_3$, M=Ge, Sn, or Pb; ad) $H_3CC(NH_2)_2MI_3$, M=Ge, Sn, or Pb; ae) $C(NH_2)_3MI_3$, M=Ge, Sn, or Pb. Examples of Type IIB materials that include it—conjugated divalent organic cations, such as alkyl viologen (RV; R=H, Me, Et and the like), polymeric viologens, polyaromatic pyridines, or polyaromatic pyridine, include $HVSnI_4$, $RVSn_2I_6$ and $(Acr)SnI_3$. Charts 1 and 2 show the structures of several organic cations that can be included in Type II materials.

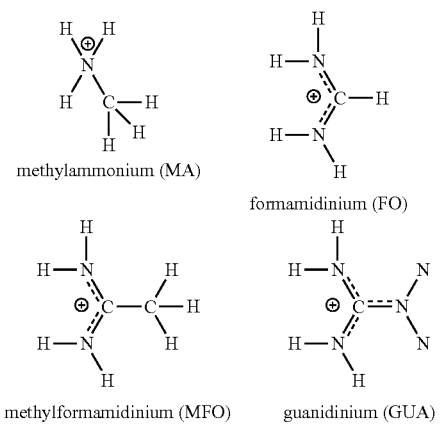

Chart 1. Examples of monovalent organic cations that can be included in Type IIA materials.

methylammonium (MA)

formamidinium (FO)

methylformamidinium (MFO)

guanidinium (GUA)

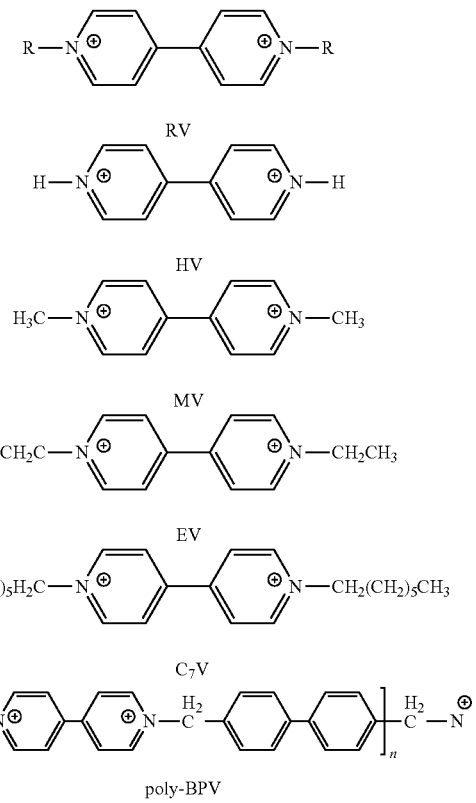

Chart 2. Examples of alkyl viologens that can be included in Type IIB materials.

RV

HV

MV

EV $C_7V$ poly-BPV

Single crystals of the Type IIA materials can be grown directly from solution by leaving the precipitate inside the mother liquor for 1-2 days.

For Type IIB materials, where the solid precipitates immediately after addition of the organic iodide, a different method is adopted: a solution of the organic iodide in aqueous HI (2 ml, 57%) is gently layered above a solution of $MI_2$ in HI (57%) and $H_3PO_2$ (50%) and heated to 120° C. (6.8 ml, 4:1 volume ratio). Slow mixing of the layers affords high quality single-crystals over a period of 5-6 hours.

The following tables contain examples of materials and synthesis conditions for the synthesis of Type II materials:

| Composition | Reagent 1 | Reagent 2 | Colour | Conditions |
|---|---|---|---|---|
| $CH_3NH_3SnI_3$ | $SnI_2$ (1.00 mmol) | $CH_3NH_3I$ (1.0 mmol) | Black | Δ, $N_2$, HI, $H_3PO_2$ |
| $HC(NH_2)_2SnI_3$ | $SnI_2$ (1.00 mmol) | $HC(NH_2)_2I$ (1.0 mmol) | Black | Δ, $N_2$, HI, $H_3PO_2$ |
| $CH_3C(NH_2)_2SnI_3$ | $SnI_2$ (1.00 mmol) | $CH_3C(NH_2)_2I$ (1.0 mmol) | Red | Δ, $N_2$, HI, $H_3PO_2$ |
| $C(NH_2)_3SnI_3$ | $SnI_2$ (1.00 mmol) | $C(NH_2)_3I$ (1.0 mmol) | Orange | Δ, $N_2$, HI, $H_3PO_2$ |
| $HVSnI_4$ | $SnI_2$ (1.00 mmol) | $HVI_2$ (0.5 mmol) | Black | Δ, $N_2$, HI, $H_3PO_2$ |
| $MVSnI_4$ | $SnI_2$ (1.00 mmol) | $MVI_2$ (0.5 mmol) | Black | Δ, $N_2$, HI, $H_3PO_2$ |
| $EVSnI_4$ | $SnI_2$ (1.00 mmol) | $EVI_2$ (0.5 mmol) | Black | Δ, $N_2$, HI, $H_3PO_2$ |
| $AcrSnI_3$ | $SnI_2$ (1.00 mmol) | Acr (1.0 mmol) | Black | Δ, $N_2$, HI, $H_3PO_2$ |
| $CH_3NH_3PbI_3$ | $PbI_2$ (1.00 mmol) | $CH_3NH_3I$ (1.0 mmol) | Black | Δ, $N_2$, HI, $H_3PO_2$ |
| $HC(NH_2)_2PbI_3$ | $PbI_2$ (1.00 mmol) | $HC(NH_2)_2I$ (1.0 mmol) | Black | Δ, $N_2$, HI, $H_3PO_2$ |
| $CH_3C(NH_2)_2PbI_3$ | $PbI_2$ (1.00 mmol) | $CH_3C(NH_2)_2I$ (1.0 mmol) | Yellow | Δ, $N_2$, HI, $H_3PO_2$ |
| $C(NH_2)_3PbI_3$ | $PbI_2$ (1.00 mmol) | $C(NH_2)_3I$ (1.0 mmol) | Yellow | Δ, $N_2$, HI, $H_3PO_2$ |
| $CH_3NH_3GeI_3$ | $GeI_4$ (1.00 mmol) | $CH_3NH_3I$ (1.0 mmol) | Red | Δ, $N_2$, HI, $H_3PO_2$ |
| $HC(NH_2)_2GeI_3$ | $GeI_4$ (1.00 mmol) | $HC(NH_2)_2I$ (1.0 mmol) | Orange | Δ, $N_2$, HI, $H_3PO_2$ |
| $CH_3C(NH_2)_2GeI_3$ | $GeI_4$ (1.00 mmol) | $CH_3C(NH_2)_2I$ (1.0 mmol) | Yellow | Δ, $N_2$, HI, $H_3PO_2$ |
| $C(NH_2)_3GeI_3$ | $GeI_4$ (1.00 mmol) | $C(NH_2)_3I$ (1.0 mmol) | Yellow | Δ, $N_2$, HI, $H_3PO_2$ |

Crystal data and structure refinement for $CH_3NH_3GeI_3$, $CH_3NH_3SnI_3$ and $CH_3NH_3PbI_3$.

| Identification code | $CH_3NH_3GeI_3$ | $CH_3NH_3SnI_3$ | $CH_3NH_3PbI_3$ |
|---|---|---|---|
| Empirical formula | C H6 I3 N Ge | C H6 I3 N Sn | C H6 I3 N Pb |
| Formula weight | 485.36 | 531.46 | 619.96 |
| Temperature | 293(2) K | 293(2) K | 293(2) K |
| Wavelength | Mo Kα 0.71073 Å | Mo Kα 0.71073 Å | Mo Kα 0.71073 Å |
| Crystal system | Trigonal | Tetragonal | Tetragonal |
| Space group | R3m | P4mm | I4cm |
| Unit cell dimensions | a = 8.5534(12) Å | a = 6.2302(9) Å | a = 8.8494(13) Å |
| | α = 90° | α = 90° | α = 90° |
| | a = 8.5534(12) Å | b = 6.2302(9)) Å | b = 8.8494(13) Å |
| | β = 90° | β = 90° | β = 90° |
| | c = 11.162(2) Å | c = 6.2316(12) Å | c = 12.642(3) Å |
| | γ = 120° | γ = 90° | γ = 90° |
| Volume | 707.2(2) Å$^3$ | 241.88(7) Å$^3$ | 990.0(3) Å$^3$ |
| Z | 3 | 1 | 4 |
| Density (calculated) | 3.419 g/cm$^3$ | 3.649 g/cm$^3$ | 4.159 g/cm$^3$ |
| Absorption coefficient | 12.983 mm$^{-1}$ | 12.128 mm$^{-1}$ | 26.312 mm$^{-1}$ |
| F(000) | 630 | 228 | 1040 |
| Crystal size | | | |
| Theta range for data collection | 3.30 to 29.05°. | 3.27 to 28.94°. | 2.81 to 29.03°. |
| Index ranges | −9 <= h <= 10, −11 <= k <= 11, −15 <= l <= 15 | −8 <= h <= 8, −8 <= k <= 8, −8 <= l <= 8 | −12 <= h <= 12, −12 <= k <= 10, −16 <= l <= 15 |
| Reflections collected | 2203 | 2164 | 4758 |
| Independent reflections | 506 [R(int) = 0.0359] | 411 [R(int) = 0.0458] | 678 [R(int) = 0.0669] |
| Completeness to theta = 24.98° | 98.5% | 98.2% | 97.1% |
| Refinement method | Full-matrix least-squares on F$^2$ | Full-matrix least-squares on F$^2$ | |
| Data/restraints/parameters | 506/1/14 | 411/1/16 | 678/2/17 |
| Goodness-of-fit on F$^2$ | 1.364 | 1.234 | 1.248 |
| Final R indices [I > 2sigma(I)] | R1 = 0.0364, wR2 = 0.0533 | R1 = 0.0325, wR2 = 0.0576 | R1 = 0.0370, wR2 = 0.0820 |
| R indices (all data) | R1 = 0.079, wR2 = 0.0535 | R1 = 0.0453, wR2 = 0.0617 | R1 = 0.410, wR2 = 0.834 |
| Absolute structure parameter | 0.03(5) | 0.2(5) | 0(10) |
| Extinction coefficient | 0.0027(3) | 0 | 0.00086(14) |
| Largest diff. peak and hole | 0.637 and −0.766 e/Å$^{-3}$ | 0.864 and −0.718 e/Å$^{-3}$ | 0.967 and −1.505 e/Å$^{-3}$ |

Crystal data and structure refinement for $HC(NH_2)_2GeI_3$, $HC(NH_2)_2SnI_3$ and $HC(NH_2)_2PbI_3$.

| Identification code | $HC(NH_2)_2GeI_3$ | $HC(NH_2)_2SnI_3$ | $HC(NH_2)_2PbI_3$ |
|---|---|---|---|
| Empirical formula | C H5 I3 N2 Ge | C H5 I3 N2 Sn | C H5 I3 N2 Pb |
| Formula weight | 498.36 | 544.46 | 632.96 |
| Temperature | 293(2) K | 293(2) K | 293(2) K |
| Wavelength | Mo Kα 0.71073 Å | Mo Kα 0.71073 Å | Mo Kα 0.71073 Å |
| Crystal system | Trigonal | Tetragonal | Trigonal |
| Space group | R3m | P4mm | P3m1 |
| Unit cell dimensions | a = 8.4669(12) Å | a = 6.3079(9) Å | a = 8.9816(13) Å |
| | α = 90° | α = 90° | α = 90° |
| | a = 8.4669(12) Å | b = 6.3079(9) Åv | b = 8.9816(13) Å |
| | β = 90° | β = 90° | β = 90° |
| | c = 11.729(2) Å | c = 6.3087(13) Å | c = 11.003(2) Å |
| | γ = 120° | γ = 90° | γ = 120° |
| Volume | 728.2(2) Å$^3$ | 252.02(7) Å$^3$ | 768.7(2) Å$^3$ |
| Z | 3 | 1 | 4 |
| Density (calculated) | 3.409 g/cm$^3$ | 3.602 g/cm$^3$ | 4.102 g/cm$^3$ |
| Absorption coefficient | 12.616 mm$^{-1}$ | 11.694 mm$^{-1}$ | 25.423 mm$^{-1}$ |
| F(000) | 648 | 234 | 798 |
| Crystal size | | | |
| Theta range for data collection | 3.28 to 29.15°. | 3.23 to 29.20°. | 1.85 to 29.19°. |
| Index ranges | −11 <= h <= 11, −10 <= k <= 11, −15 <= l <= 15 | −8 <= h <= 8, −8 <= k <= 8, −7 <= l <= 7 | −12 <= h <= 12, −12 <= k <= 11, −15 <= l <= 15 |
| Reflections collected | 2214 | 2423 | 7475 |
| Independent reflections | 508 [R(int) = 0.0508] | 391 [R(int) = 0.0210] | 1645 [R(int) = 0.0459] |
| Completeness to theta = 24.98° | 96.3% | 87.8% | 99.6% |
| Refinement method | Full-matrix least-squares on F$^2$ | Full-matrix least-squares on F$^2$ | Full-matrix least-squares on F$^2$ |
| Data/restraints/parameters | 508/1/17 | 391/1/16 | 1645/1/30 |
| Goodness-of-fit on F$^2$ | 1.131 | 1.217 | 1.112 |
| Final R indices [I > 2sigma(I)] | R1 = 0.0443, wR2 = 0.1138 | R1 = 0.0261, wR2 = 0.0602 | R1 = 0.0374, wR2 = 0.0675 |
| R indices (all data) | R1 = 0.0507, wR2 = 0.1197 | R1 = 0.0323, wR2 = 0.0627 | R1 = 0.954, wR2 = 0.879 |
| Absolute structure parameter | 0.00(13) | 0.1(5) | 0.25(15) |
| Extinction coefficient | 0.0000(11) | 0.026(5) | 0.00026(15) |
| Largest diff. peak and hole | 1.173 and −1.874 e/Å$^{-3}$ | 1.020 and −0.753 e/Å$^{-3}$ | 5.432 and −6.184 e/Å$^{-3}$ |

40

Crystal data and structure refinement for $C(NH_2)_3SnI_3$, $\alpha\text{-}CH_3C(NH_2)_2SnI_3$ and $\beta\text{-}CH_3C(NH_2)_2SnI_3$.

| Identification code | $C(NH_2)_3SnI_3$ | $\alpha\text{-}CH_3C(NH_2)_2SnI_3$ | $\beta\text{-}CH_3C(NH_2)_2SnI_3$ |
|---|---|---|---|
| Empirical formula | C H6 I3 N3 Sn | C2 H7 I3 N2 Sn | C2 H7 I3 N2 Sn |
| Formula weight | 559.48 | 558.49 | 558.49 |
| Temperature | 150(2) K | 293(2) K | 100(2) K |
| Wavelength | Mo Kα 0.71073 Å | Mo Kα 0.71073 Å | Mo Kα 0.71073 Å |
| Crystal system | Hexagonal | Hexagonal | Monoclinic |
| Space group | P63/m | P63mc | P21 |
| Unit cell dimensions | a = 9.3124(13) Å | a = 9.2509(13) Å | a = 12.746(3) Å |
| | α = 90° | α = 90° | α = 90° |
| | a = 9.3124(13) Å | b = 9.2509(13) Å | b = 9.2837(13) Å |
| | β = 90° | β = 90° | β = 112.21(3)° |
| | c = 21.230(4) Å | c = 15.361(3) Å | c = 14.709(3) Å |
| | γ = 120° | γ = 120° | γ = 90° |
| Volume | 1594.4(4) Å$^3$ | 1138.4(3) Å$^3$ | 1611.4(3) Å$^3$ |
| Z | 6 | 4 | 6 |
| Density (calculated) | 3.496 g/cm$^3$ | 3.217 g/cm$^3$ | 3.410 g/cm$^3$ |
| Absorption coefficient | 11.054 mm$^{-1}$ | 10.317 mm$^{-1}$ | 10.940 mm$^{-1}$ |
| F(000) | 1452 | 940 | 1936 |
| Crystal size | | | |
| Theta range for data collection | 1.92 to 24.95°. | 2.54 to 24.98°. | 1.50 to 27.00°. |
| Index Ranges | −11 <= h <= 11, −11 <= k <= 11, −25 <= l <= 25 | −10 <= h <= 9, −10 <= k <= 9, −18 <= l <= 18 | −15 <= h <= 16, −11 <= k <= 11, −18 <= l <= 18 |
| Reflections collected | 10355 | 3928 | 12890 |

-continued

| Identification code | C(NH$_2$)$_3$SnI$_3$ | α-CH$_3$C(NH$_2$)$_2$SnI$_3$ | β-CH$_3$C(NH$_2$)$_2$SnI$_3$ |
|---|---|---|---|
| Independent reflections | 971 [R(int) = 0.0990] | 750 [R(int) = 0.0860] | 7027 [R(int) = 0.0394] |
| Completeness to theta = 24.98° | 100.0% | 94.3% | 100% |
| Refinement method | Full-matrix least-squares on F$^2$ | Full-matrix least-squares on F$^2$ | Full-matrix least-squares on F$^2$ |
| Data/restraints/parameters | 971/0/43 | 750/5/30 | 7027/1/218 |
| Goodness-of-fit on F$^2$ | 1.183 | 1.014 | 1.095 |
| Final R indices [I > 2sigma(I)] | R1 = 0.0634, wR2 = 0.1176 | R1 = 0.0630, wR2 = 0.1081 | R1 = 0.0539, wR2 = 0.1516 |
| R indices (all data) | R1 = 0.0759, wR2 = 0.1216 | R1 = 0.1342, wR2 = 0.1271 | R1 = 0.0612, wR2 = 0.01551 |
| Absolute structure parameter | Extinction coefficient = 0.00023(17) | 0.0(7) | 0.32(13) |
| Largest diff. peak and hole | 1.032 and −1.371 e/Å$^{-3}$ | 0.735 and −0.572 e/Å$^{-3}$ | 4.072 and −1.683 e/Å$^{-3}$ |

Crystal data and structure refinement for HVSnI$_4$, MVSn$_2$I$_6$, EVSn$_2$I$_6$ and AcrSnI$_3$.

| Identification code | HVSnI$_4$ | MVSn$_2$I$_6$ | EVSn$_2$I$_6$ | AcrSnI$_3$ |
|---|---|---|---|---|
| Empirical formula | C10 H10 I4 N2 Sn | C12 I6 N2 Sn2 H14 | C14 I6 N2 Sn2 H18 | C13 H10 I3 N Sn |
| Formula weight | 784.49 | 1159.2 | 1194.94 | 679.61 |
| Temperature | 293(2) K | 293(2) K | 293(2) K | 293(2) K |
| Wavelength | 0.71073 E | 0.71073 A | 0.71073 E | 0.71073 E |
| Crystal system | Monoclinic | Trigonal | Monoclinic | Monoclinic |
| Space group | C2/c | P -3 | P2$_1$/c | P2$_1$/n |
| Unit cell dimensions | a = 17.218(3) Å<br>α = 90°<br>b = 14.195(3) Å<br>β = 116.92(3)°<br>c = 7.8515(5) Å<br>γ = 90° | a = 16.078 Å,<br>α = 90°<br>b = 16.078 Å,<br>β = 90°<br>c = 25.637 Å,<br>γ = 120° | a = 12.116(2) Å<br>α = 90°<br>b = 13.941(3) Å<br>β = 90.51(3)°<br>c = 24.677(5) Å<br>γ = 120° | a = 4.6467(9) Å<br>α = 90°<br>b = 24.710(5) Å<br>β = 90.18(3)°<br>c = 14.817(3) Å<br>γ = 120° |
| Volume | 1710.9(6) Å$^3$ | 5739.338 Å$^3$ | 4167.8(14) Å$^3$ | 1701.2(6) Å$^3$ |
| Z | 4 | 9 | 6 | 4 |
| Density (calculated) | 3.046 g/cm$^{33}$ | 3.0174 g/cm$^3$ | 2.857 Mg/m$^3$ | 2.653 Mg/m$^3$ |
| Absorption coefficient | 8.695 mm$^{-1}$ | 9.111 mm$^{-1}$ | 8.465 mm$^{-1}$ | 6.930 mm$^{-1}$ |
| F(000) | 1384 | 4492 | 3096 | 1216 |
| Crystal size | | | | |
| Theta range for data collection | 2.65 to 24.99°. | 1.66 to 29.23° | 1.65 to 25.00°. | 1.60 to 24.99°. |
| Index ranges | −20 <= h <= 20,<br>−15 <= k <= 16,<br>−9 <= l <= 8 | −18 <= h <= 20,<br>−21 <= k <= 19,<br>−35 <= l <= 35 | −14 <= h <= 14,<br>−16 <= k <= 16,<br>−29 <= l <= 29 | −5 <= h <= 5,<br>−29 <= k <= 29,<br>−17 <= l <= 17 |
| Reflections collected | 5144 | 32162 | 26382 | 12633 |
| Independent reflections | 1499 [R(int) = 0.0538] | 9185 [R$_{int}$ = 0.1623] | 7347 [R(int) = 0.1134] | 2956[R(int) = 0.0548] |
| Completeness to theta = | 99.3% | 98% | 100.0% | 98.1% |
| Refinement method | Full-matrix least-squares on F$^2$ | Full-matrix least-squares on F$^2$ | Full-matrix least-squares on F$^2$ | Full-matrix least-squares on F$^2$ |
| Data/restraints/parameters | 1499/0/78 | 9185/0/190 | 7347/0/325 | 2956/0/164 |
| Goodness-of-fit on F2 | 1.161 | 1.31 | 0.928 | 1.088 |
| Final R indices [I > 2sigma(I)] | R1 = 0.0451,<br>wR2 = 0.0496 | [I > 3σ] R$_{obs}$ = 0.0737,<br>wR$_{obs}$ = 0.1063 | R1 = 0.0626,<br>wR2 = 0.0733 | R1 = 0.0483,<br>wR2 = 0.0896 |
| R indices (all data) | R1 = 0.0725,<br>wR2 = 0.0536 | R$_{all}$ = 0.2392,<br>wR$_{all}$ = 0.1425 | R1 = 0.1489,<br>wR2 = 0.0896 | R1 = 0.0636,<br>wR2 = 0.0989 |
| Largest diff. peak and hole | 0.909 and −1.024 e.Å$^{-3}$ | 12.53 and −9.23 e.Å$^{-3}$ | 0.845 and −1.153 e.Å$^{-3}$ | 1.31 and −1.427 eÅ.$^{-3}$ |

Some examples of Type III materials include ah) $CsMIX_2$, ai) $CH_3NH_3MIX_2$, aj) $HC(NH_2)_2MIX_2$, ak) $CH_3CC(NH_2)_2MIX_2$, al) $C(NH_2)_3MIX_2$, where X is any combinations of group 17 elements. The examples of specific molar ratios of starting materials and obtained products are shown in Table ai)-ak). All numbers in table are in mmol.

TABLE ah)

$CsM(I_{3-x}X_x)$: M = Ge, Sn, or Pb

| Reagent/ Composition | CsF | CsCl | CsBr | CsI | $SnF_2$ | $SnCl_2$ | $SnBr_2$ | $SnI_2$ |
|---|---|---|---|---|---|---|---|---|
| $CsSnF_2(F_{1-x}I_x)$ | x = 0.00-0.99 | — | — | x = 0.01-1.00 | x = 1.00 | — | — | — |
| $CsSnCl_2(Cl_{1-x}I_x)$ | — | x = 0.00-0.99 | — | x = 0.01-1.00 | — | x = 1.00 | — | — |
| $CsSnBr_2(Br_{1-x}I_x)$ | — | — | x = 0.00-0.99 | x = 0.01-1.00 | — | — | x = 1.00 | — |
| $CsSnIF(F_{1-x}I_x)$ | x = 0.01-0.99 | — | — | x = 0.01-0.99 | x = 0.50 | — | — | x = 0.50 |
| $CsSnICl(Cl_{1-x}I_x)$ | — | x = 0.01-0.99 | — | x = 0.01-0.99 | — | x = 0.50 | — | x = 0.50 |
| $CsSnIBr(Br_{1-x}I_x)$ | — | — | x = 0.00-0.99 | x = 0.01-0.99 | — | — | x = 0.50 | x = 0.50 |
| $CsSnI_2(I_{1-x}F_x)$ | x = 0.01-1.00 | — | — | x = 0.00-0.99 | — | — | — | x = 1.00 |
| $CsSnI_2(I_{1-x}Cl_x)$ | — | x = 0.01-1.00 | — | x = 0.00-0.99 | — | — | — | x = 1.00 |
| $CsSnI_2(I_{1-x}Br_x)$ | — | — | x = 0.01-0.99 | x = 0.00-0.99 | — | — | — | x = 1.00 |

TABLE ai)

$CH_3NH_3M(I_{3-x}X_x)$: M = Ge, Sn, or Pb

| Reagent/ Composition | $CH_3NH_3F$ | $CH_3NH_3Cl$ | $CH_3NH_3Br$ | $CH_3NH_3I$ | $SnF_2$ | $SnCl_2$ | $SnBr_2$ | $SnI_2$ |
|---|---|---|---|---|---|---|---|---|
| $MASnF_2(F_{1-x}I_x)$ | x = 0.00-0.99 | — | — | x = 0.01-1.00 | x = 1.00 | — | — | — |
| $MASnCl_2(Cl_{1-x}I_x)$ | — | x = 0.00-0.99 | — | x = 0.01-1.00 | — | x = 1.00 | — | — |
| $MASnBr_2(Br_{1-x}I_x)$ | — | — | x = 0.00-0.99 | x = 0.01-1.00 | — | — | x = 1.00 | — |
| $MASnIF(F_{1-x}I_x)$ | x = 0.01-0.99 | — | — | x = 0.01-0.99 | x = 0.50 | — | — | x = 0.50 |
| $MASnICl(Cl_{1-x}I_x)$ | — | x = 0.01-0.99 | — | x = 0.01-0.99 | — | x = 0.50 | — | x = 0.50 |
| $MASnIBr(Br_{1-x}I_x)$ | — | — | x = 0.00-0.99 | x = 0.01-0.99 | — | — | x = 0.50 | x = 0.50 |
| $MASnI_2(I_{1-x}F_x)$ | x = 0.01-1.00 | — | — | x = 0.00-0.99 | — | — | — | x = 1.00 |
| $MASnI_2(I_{1-x}Cl_x)$ | — | x = 0.01-1.00 | — | x = 0.00-0.99 | — | — | — | x = 1.00 |
| $MASnI_2(I_{1-x}Br_x)$ | — | — | x = 0.01-0.99 | x = 0.00-0.99 | — | — | — | x = 1.00 |

TABLE aj)

$HC(NH_2)_2M(I_{3-x}X_x)$: M = Ge, Sn, or Pb

| Reagent/ Composition | $HC(NH_2)_2F$ | $HC(NH_2)_2Cl$ | $HC(NH_2)_2Br$ | $HC(NH_2)_2I$ | $SnF_2$ | $SnCl_2$ | $SnBr_2$ | $SnI_2$ |
|---|---|---|---|---|---|---|---|---|
| $FOSnF_2(F_{1-x}I_x)$ | x = 0.00-0.99 | — | — | x = 0.01-1.00 | x = 1.00 | — | — | — |
| $FOSnCl_2(Cl_{1-x}I_x)$ | — | x = 0.00-0.99 | — | x = 0.01-1.00 | — | x = 1.00 | — | — |
| $FOSnBr_2(Br_{1-x}I_x)$ | — | — | x = 0.00-0.99 | x = 0.01-1.00 | — | — | x = 1.00 | — |
| $FOSnIF(F_{1-x}I_x)$ | x = 0.01-0.99 | — | — | x = 0.01-0.99 | x = 0.50 | — | — | x = 0.50 |
| $FOSnICl(Cl_{1-x}I_x)$ | — | x = 0.01-0.99 | — | x = 0.01-0.99 | — | x = 0.50 | — | x = 0.50 |
| $FOSnIBr(Br_{1-x}I_x)$ | — | — | x = 0.00-0.99 | x = 0.01-0.99 | — | — | x = 0.50 | x = 0.50 |
| $FOSnI_2(I_{1-x}F_x)$ | x = 0.01-1.00 | — | — | x = 0.00-0.99 | — | — | — | x = 1.00 |
| $FOSnI_2(I_{1-x}Cl_x)$ | — | x = 0.01-1.00 | — | x = 0.00-0.99 | — | — | — | x = 1.00 |
| $FOSnI_2(I_{1-x}Br_x)$ | — | — | x = 0.01-0.99 | x = 0.00-0.99 | — | — | — | x = 1.00 |

TABLE ak)

$CH_3C(NH_2)_2M(I_{3-x}X_x)$: M = Ge, Sn, or Pb

| Reagent/ Composition | $CH_3C(NH_2)_2F$ | $CH_3C(NH_2)_2Cl$ | $CH_3C(NH_2)_2Br$ | $CH_3C(NH_2)_2I$ | $SnF_2$ | $SnCl_2$ | $SnBr_2$ | $SnI_2$ |
|---|---|---|---|---|---|---|---|---|
| $MFSnF_2(F_{1-x}I_x)$ | x = 0.00-0.99 | — | — | x = 0.01-1.00 | x = 1.00 | — | — | — |
| $MFSnCl_2(Cl_{1-x}I_x)$ | — | x = 0.00-0.99 | — | x = 0.01-1.00 | — | x = 1.00 | — | — |
| $MFSnBr_2(Br_{1-x}I_x)$ | — | — | x = 0.00-0.99 | x = 0.01-1.00 | — | — | x = 1.00 | — |
| $MFSnIF(F_{1-x}I_x)$ | x = 0.01-0.99 | — | — | x = 0.01-0.99 | x = 0.50 | — | — | x = 0.50 |
| $MFSnICl(Cl_{1-x}I_x)$ | — | x = 0.01-0.99 | — | x = 0.01-0.99 | — | x = 0.50 | — | x = 0.50 |
| $MFSnIBr(Br_{1-x}I_x)$ | — | — | x = 0.00-0.99 | x = 0.01-0.99 | — | — | x = 0.50 | x = 0.50 |
| $MFSnI_2(I_{1-x}F_x)$ | x = 0.01-1.00 | — | — | x = 0.00-0.99 | — | — | — | x = 1.00 |
| $MFSnI_2(I_{1-x}Cl_x)$ | — | x = 0.01-1.00 | — | x = 0.00-0.99 | — | — | — | x = 1.00 |
| $MFSnI_2(I_{1-x}Br_x)$ | — | — | x = 0.01-0.99 | x = 0.00-0.99 | — | — | — | x = 1.00 |

TABLE a1)

$C(NH_2)_3M(I_{3-x}X_x)$: M = Ge, Sn, or Pb

| Reagent/Composition | $C(NH_2)_3F$ | $C(NH_2)_3Cl$ | $C(NH_2)_3Br$ | $C(NH_2)_3I$ | $SnF_2$ | $SnCl_2$ | $SnBr_2$ | $SnI_2$ |
|---|---|---|---|---|---|---|---|---|
| $GUSnF_2(F_{1-x}I_x)$ | x = 0.00-0.99 | — | — | x = 0.01-1.00 | x = 1.00 | — | — | — |
| $GUSnCl_2(Cl_{1-x}I_x)$ | — | x = 0.00-0.99 | — | x = 0.01-1.00 | — | x = 1.00 | — | — |
| $GUSnBr_2(Br_{1-x}I_x)$ | — | — | x = 0.00-0.99 | x = 0.01-1.00 | — | — | x = 1.00 | — |
| $GUSnIF(F_{1-x}I_x)$ | x = 0.01-0.99 | — | — | x = 0.01-0.99 | x = 0.50 | — | — | x = 0.50 |
| $GUSnICl(Cl_{1-x}I_x)$ | — | x = 0.01-0.99 | — | x = 0.01-0.99 | — | x = 0.50 | — | x = 0.50 |
| $GUSnIBr(Br_{1-x}I_x)$ | — | — | x = 0.00-0.99 | x = 0.01-0.99 | — | — | x = 0.50 | x = 0.50 |
| $GUSnI_2(I_{1-x}F_x)$ | x = 0.01-1.00 | — | — | x = 0.00-0.99 | — | — | — | x = 1.00 |
| $GUSnI_2(I_{1-x}Cl_x)$ | — | x = 0.01-1.00 | — | x = 0.00-0.99 | — | — | — | x = 1.00 |
| $GUSnI_2(I_{1-x}Br_x)$ | — | — | x = 0.01-0.99 | x = 0.00-0.99 | — | — | — | x = 1.00 |

The materials were prepared by mixing appropriate amounts of $SnX_2$, CsX, $CH_3NH_3X$, $HC(NH_2)_2X$, $H_3CC(NH_2)_2X$ or $C(NH_2)_3X$ in several ratios, as listed below (X can be F, Cl, Br or I). The solids were placed in borosilicate tubes and placed in a sand bath preheated to 250° C. The obtained melts were cooled in air. Reaction time varied between 1-5 minutes, increasing as a function of the molecular weight of X. When longer reaction times were required to obtain the melt (>2 min), the solids were heated up under a gentle flow of $N_2$.

Examples of Type V materials are any possible combination of Type I-IV materials. For example, $(AMX_3)_{1-x}(M'O_z)_x$ and $(AMX_3)_{1-x}(AM'F_6)_x$. An extreme example of this type of materials is the melt of "$CsSnF_2I$" composition, which attacks its reaction container ($SiO_2$ or $Al_2O_3$) to form mixed-metal materials. The PL intensity of the materials thus observed can be optimized by varying the annealing time. Incorporating two metal shifted wavelengths of emission spectra as shown in $AM_{1-x}M'_xX_3$, $(AMX_3)_{1-x}(A'M'X'_3)_x$ and $(AM_{1-z}X_{3-z})(M'X_z)$. The transition metal halides can be used to alter the wavelengths of emission spectra.

Properties of A/M/X Metal Halide Compounds that Emit Photoluminescence in the Visible and Near Infrared Regions.

I) Photo-Response

A sample was placed in a sample holder, exposed to the laser and its PL intensity was measured. This was the starting point. Without turning off the beam, PL intensity was recorded as a function of irradiation time at specified intervals. After the last measurement during irradiation the laser was shut down and the sample was left in the dark. A final PL intensity measurement was made after about 1 hour.

The photoluminescence spectra of various embodiments of the A/M/X compounds are shown in FIGS. 1, 3, 5(A)-(C), 7(B), 8, 10, 12(A)-(B), 14(A)-(B), 16, 18, 20, and 24 (A)-(B). Corresponding absorbance spectra of various embodiments of the A/M/X compounds are shown in FIGS. 2, 4, 6, 7(A), 9, 11, 13, 15, 17, 19, and 25 (A)-(D).

It was consistently observed that the materials responded to prolonged exposure to light. Depending on the particular materials the initially observed PL intensity was either gaining or losing strength during irradiation until it reached its maximum effect at which point PL intensity stabilized. When the laser was shut off, the material slowly relaxed back to its original state prior to light excitation. Some materials were classified based on the effect of light on the PL intensity. The classification is the following:

i) Negative photoresponse (the PL intensity decreases as a function of irradiation): Materials that typically display such an effect are $ASnI_xCl_y$ and particularly so as the y/x ratio increases, in which case the effect is more pronounced.

ii) Positive photoresponse (the PL intensity decreases as a function of irradiation): Materials that typically display such an effect are $(CsSnI_3)_{1-x}(SnO)_x$ compositions (particularly for x>0.5) and $APbX_3$ materials.

iii) Irregular photoresponse (the PL intensity changes as a function of irradiation but not in a specific manner): Materials that typically display such an effect are generally $Cs(SnI_3)_{1-x}(CsSi_{0.5}F_3)_x$ compositions and, in general, most of the compounds containing F.

II) Photo-Reactivity

A sample was placed in a sample holder, exposed to the laser and its PL intensity was measured. This was the starting point. PL intensity was recorded as a function of irradiation time. After irradiation, the sample was removed and examined for color changes on the spot of irradiation.

Some of the materials described above, particularly Type III materials prepared by synthetic process 3, were prepared as a yellow modification which has a weak PL intensity or is totally PL-inactive. Irradiation caused a color change in the material which was accompanied with an enhancement of PL emission. The transformation was reversible and the material relaxed back to its originally prepared state. The effect was more pronounced for mixed I/F compositions.

Solution-Based Thin Film Preparation of A/M/X Compounds and Type I, II, III, IV and V Systems Exhibiting Photoluminescence.

Classes of compounds A/M/X (A=alkali metals, organic cations; M=Group 14; X=Group 17) and Type I, II, III, IV and V systems exhibiting photoluminescence were found to be soluble in polar organic solvents such as N,N-dimethylformamide, acetonitrile and their mixtures to give transparent solutions. The color of solutions was dependent on that of the solids: $CsSnI_3$ gave yellow solutions and $CsSnCl_3$ yielded colorless solutions. Based on this observation, the solution-based thin film preparation method of materials described in Part 1 was developed.

Some characteristics of the compounds and systems are: (1) the systems are highly soluble in polar organic solvents to give viscous, transparent solutions; (2) by employing such a dissolution properties, a solution-processed thin film preparation method of those materials by spin-coating or spraying was developed; (3) such method was generally applicable to all relevant compounds of the A/M/X systems; (4) Because this was a low-temperature process at 120-150° C., various cheap substrates of plastics can be used, which are flexible and favorable for many applications.

Many members of A/M/X system undergo phase-change driven by temperature. $CsSnI_3$ is a complex example that has two different phases at RT: yellow one-dimensional and black perovskite phases. The black phase has two more high temperature phases by a distortion of perovskite framework. Only the black phase emits desirable photoluminescence (PL) at 950 nm at RT. Accordingly, stabilization of black phase in a thin film form was desired.

Recently, synthesis and characterization of polycrystalline $CsSnI_{3-x}Cl_x$ thin films have been reported using a vacuum deposition technique. They were prepared by a two-step method. First, multiple layers of $SnI_2$ (or $SnCl_2$) and CsI were alternately deposited in vacuum (~$10^5$ torr) on glass, Si and ceramic substrates by a combination of thermal and e-beam evaporators. The resulting films were the yellow phase and did not emit PL at 950 nm. Then, thermal annealing was required to activate PL emission over 350° C. This method has several drawbacks. Firstly, it requires expensive high vacuum procedures. Secondly, the evaporation method does not provide precise chemical composition control. Thus doping to optimize desirable performance is challenging. Thirdly, the deposited films need to be annealed at high temperature at 350° C. for PL activity.

The present solution-processing procedure is advantageous in that thin films of the materials immediately form the black phase after spin-coating and exhibit strong PL emission at 950 nm at RT. Similarly, in the case of $CsSnCl_3$, the present spin coating process stabilizes the high temperature phase of the yellow perovskite structure rather than the room temperature phase of white one-dimensional structure. The solution-processed deposition procedure is highly reproducible, applicable to large-area substrates, available in designed doping for optimizing properties and incomparably cheaper than vacuum techniques. By finishing preparation at low temperature, cheap and flexible plastic substrates are usable. The typical thin films of $CsSnI_3$ emits 21-fold stronger PL at 950 nm than the commercial available InP:S single crystalline wafer.

EXAMPLES

Example 1

Preparation $CsSnI_3$ Thin Films by a Solution Process

High purity $CsSnI_3$ ingots were obtained by reacting a stoichiometric mixture of CsI and $SnI_2$ in an evacuated fused silica tube at 500-550° C. for 1 h, followed by a cooling to RT for 3 h. Powders of $CsSnI_3$ (~120-350 mg) were dissolved in polar organic solvents (1 mL), such as anhydrous N,N-dimethylformamide (DMF) and acetonitrile or their mixtures to give yellow transparent solution. The solutions were filtered through a 0.2 μm syringe filter, and diluted to various concentrations. For better films, Sn/O/Cl buffer layers were pre-deposited on substrates. Highly crystalline thin films were deposited by a spin-coating process at 1000 rpm for 40 s, followed by drying at 125° C. for 5 min on a hot plate under $N_2$ atmosphere. The resulting films were black in color and could be deposited on various substrates such as Si, glass and flexible plastics.

Figure 21:
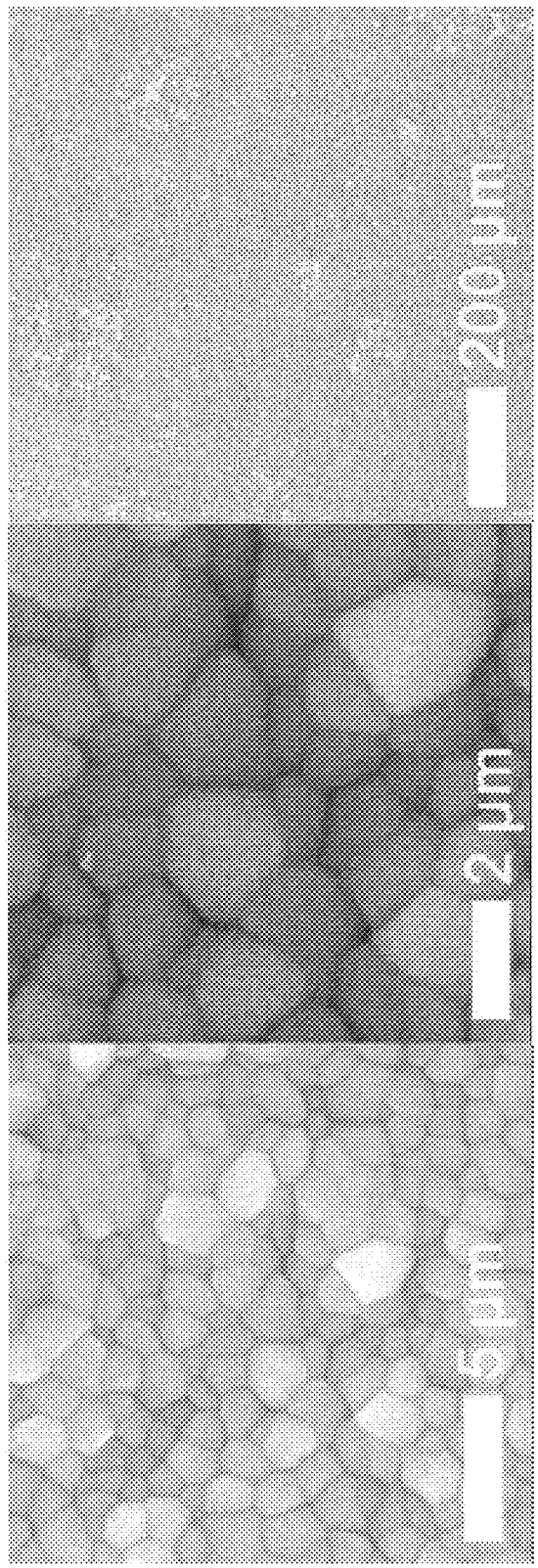
FIG. 21. Scanning electron microscopy images of $CsSnI_3$ thin films, showing continuous, polycrystalline nature of the films.

The X-ray powder diffraction pattern of the film matched well with that of a theoretical calculation of black orthorhombic phase of $CsSnI_3$. Scanning electron microscopy (SEM) images of $CsSnI_3$ thin films showed continuous surface morphology that consists of several hundred nm to several micron size grains (FIG. 21). Electron dispersive spectroscopy (EDS) on films gave a close chemical composition to the expected value. The cross-sectional image of $CsSnI_3$ films on Si substrate by transmission electron microscopy showed that the thin films are polycrystalline.

The thin films of Cs/Sn/I/Cl phases were deposited on the glass substrates coated with a reflecting layer that consists of alternating $SiO_2$ and $TiO_2$ layers. The $CsSnI_3$ films exhibited 42-fold stronger PL intensity at ~950 nm to single crystalline InP:S wafer. The $CsSnI_2Cl$ and $CsSn_2I_3Cl_2$ films exhibited 15 and 7-fold stronger PL intensity to InP:S wafer. The solution-processed film emitting strong PL also can be prepared by a spray method. The thin films of $Cs_2SnI_2Cl_2$ could be obtained by spraying the as a solution dissolved in DMF. The resulting films exhibited strong PL at 950 nm.

The same procedure can be applied to other members of the families of materials described here. Broad applications for materials exhibiting photoluminescence at RT include light emitting diodes, sensors, anti-counterfeiting, inventory, photovoltaics, solar cells and other applications.

Experimental

Materials Synthesis

1. Solid State Reaction.

Pure target materials were prepared by reacting a stoichiometric mixture of alkali metal halide (organic halide) and metal halide starting materials under vacuum in a borosilicate or fused silica tube at 450° C. for 1 h. For organic metal halide compounds, a stoichiometric mixture was reacted at 200° C. for 2 h. The same procedure was applied when metal oxides were used. Reacting mixtures were sometimes pre-reacted by grinding with mortar and pestle.

2. Solid State Reaction in an Open Container:

Stoichiometric mixtures of starting materials were loaded in a pyrex test tube (VWR, about 15 mm ID). The materials were shaken mechanically to ensure a rather homogenous mixture of the materials. The tube was placed on a sandbath heated at specified temperature, typically 450° C. under $N_2$, reacted until a homogeneous melt formed (typically 1-5 min) and quenched to air. The reaction was repeated several times to obtain homogeneous products. It is very important to keep the reaction time very short, because besides atmospheric oxygen coming in, there may also be gas evolution which is volatile $SnX_4$.

3. Solution preparation:

A two-necked flask (usually 50 or 100 mL) is charged with the corresponding Sn(II), Pb(II) or Ge(IV) halide or oxide, and a mixture of conc. HI 57% (6.8 ml, 7.58M) and conc. $H_3PO_2$ 50% (1.7 ml, 9.14M). Note: the volumes come from the fact that a Pasteur pipette contains 1.7 ml of solution, so it is 4:1 ratio in "Pasteur pipette" units. The mixture is flushed with $N_2$ gas for 1-2 minutes (through the solution) to remove most of the oxygen and a constant flow is maintained throughout the process (outside of the solution, for crystal growth purposes). For Ge, add double the volume (or sometimes more) of $H_3PO_2$ to ensure full reduction. For Pb, $H_3PO_2$ may be omitted. Typically, the scale is 1 mmol based on the Ge, Sn (or Pb) halide. For Ge, it is required to add some EtOH (10 ml) to dissolve $GeX_4$ halides. Then, under constant magnetic stirring, the mixture is heated at ~130 C by immersing the flask in a silicon oil bath, until a clear, bright yellow solution is obtained. If it is slightly orange then add more $H_3PO_2$ to make it yellow. The temperature can change (up or down) depending on specific conditions (e.g. isolation of both the kinetic and the thermodynamic product). Once the yellow solution is obtained, add the alkali metal/organic iodide. This can be added either as solid or as a solution depending on its solubility. Typically, $Al_2$ salts form insoluble products, whereas AI salts form soluble products (there are of course some exceptions!). If the addition produces a solid, I collect it by filtration (fritted glass, the solvent attacks paper!). Otherwise, a clear yellow solution should be obtained. The solvent is evaporated by heating (b.p. is about 120 C) under $N_2$ flow. At a certain point of concentration (about 4 ml, but this varies, depending on the cation) a solid separates. The solution is cooled to room temperature and the solid is filtered (fritted glass, the solvent attacks paper! !). The yields range from 50-100%. If high yield is required concentrate further. The solid is washed with an organic solvent (EtOH is almost always a good washing solvent) and dried under vacuum in air. The solid is usually stable when dry for 1-2 days. However, when in contact with the mother liquor exposed in air, the product decomposes (oxidation, hydrolysis, iodolysis, etc. . . . ) within minutes! A clear indication of oxidation is a deeply red (from $[I_3]^-$) or black ($[SnI_6]^{2-}$) color of the solution. In this case, more $H_3PO_2$ should be added. The whole process can last from 10 min to 3 h. High quality materials were prepared by dissolving equimolar amounts of $GeI_4$, $SnI_2$ or $PbI_2$ (1mmol) and $CH_3NH_3I$, $HC(NH_2)_2I$, $H_3CC(NH_2)_2I$ or $C(NH_2)_3I$ (1 mmol), respectively, in a solvent mixture comprising of concentrated aqueous solutions of HI (57%) and $H_3PO_2$ (50%) to a total of 6.8 ml (4:1 volume ratio). The solution was heated up to boiling and slowly concentrated to approximately half its volume, where a fine solid precipitates. The whole process is performed under a blanket of $N_2$. Yields vary between 50-100%.

Crystal Growth.

Typically, the precipitated solid contains X-ray quality single crystals. If not, there are two possibilities, depending on the solubility of the product. Before that, a general piece of advice is to reduce the quantities of the solids that you add. If this does not work then:

a) if a clear solution is obtained, then switch of the stirring, reduce the $N_2$ flow so that it does not disturb the solution (alternatively, add more $H_3PO_2$, remove the $N_2$ flow and cap the flask tightly) and concentrate slowly (~100 C is good practice). When a solid separates, increase heating (to about 150-170 C) and add dropwise HI until the solid redissolves. If in the process the solution oxidizes add some more $H_3PO_2$ to reduce it. Once a clear solution is obtained, turn of the heat and leave the solution for crystallization overnight.

b) if a solid precipitates immediately, then dissolve AI or $AI_2$ into a suitable solvent (avoid hydrolysable (MeCN) or basic (DMF) solvents and also don't use amines with $(CH_3)_2CO$!). Do not add this solution directly to the yellow solution. First of all, turn of the stirring and reduce the $N_2$ flow as much as possible. Then with a pipette or syringe, add a layer of a solvent on top of the aqueous layer so that mixing occurs slowly (within 5 minutes) and turn off the heat. The crystals that precipitate/grow on cooling are significantly better/larger than the ones obtained with the standard method.

Physical Measurements.

1. X-ray Powder Diffraction.

Analyses for powder samples were performed using a calibrated CPS 120 INEL X-ray powder diffractometer (Cu Kα radiation) operating at 40 kV/20 mA and equipped with a position-sensitive detector with flat sample geometry.

2. X-ray Thin Film Diffraction.

Grazing incident angle X-ray diffraction (GIAXRD) scans were measured with a Rigaku ATX-G Thin-Film Diffraction Workstation using Cu Kα radiation coupled to a multilayer mirror. The scan rate and interval were set to 2°/min and 0.10° for 2θ scan.

3. Electron Microscopy.

Semiquantitative analyses of the compounds were performed with a JEOL JSM-35C scanning electron microscope (SEM) equipped with a Tracor Northern energy dispersive spectroscopy (EDS) detector. SEM images were taken with a Hitachi S-3400N-II variable-pressure SEM. TEM investigations were carried out in JEOL 2100F microscope operating at a 200 keV accelerating voltage.

4. Solid-State UV-Vis Spectroscopy.

Optical diffuse reflectance measurements were performed at room temperature using a Shimadzu UV-3101 PC double-beam, double-monochromator spectrophotometer operating in the 200-2500 nm region. The instrument is equipped with an integrating sphere and controlled by a personal computer. $BaSO_4$ was used as a 100% reflectance standard. The sample was prepared by grinding the crystals to a powder and spreading it on a compacted surface of the powdered standard material, preloaded into a sample holder. The reflectance versus wavelength data generated, were used to estimate the band gap of the material by converting reflectance to absorption data according to Kubelka-Munk equations: $\alpha/S=(1-R)^2/(2R)$, where R is the reflectance and a and S are the absorption and scattering coefficients, respectively.

5. Raman Spectroscopy.

Raman spectra were recorded on a Holoprobe Raman spectrograph equipped with a CCD camera detector using 633 nm radiation from a HeNe laser for excitation and a resolution of 4 $cm^{-1}$. Laser power at the sample was estimated to be about 5 mW, and the focused laser beam diameter was ca. 10 μm. A total of 128 scans was sufficient to obtain good quality spectra.

6. Infrared Spectroscopy.

FT-IR spectra were recorded as solids in a CsI or KBr matrix. The samples were ground with dry CsI or KBr into a fine powder and pressed into translucent pellets. The spectra were recorded in the far-IR region (600-100 $cm^{-1}$, 2 $cm^{-1}$ resolution) and mid-IR region (500-4,000 $cm^{-1}$, 2 $cm^{-1}$ resolution) with the use of a Nicolet 6,700 FT-IR spectrometer equipped with a TGS/PE detector and silicon beam splitter.

7. Differential Thermal Analysis (DTA).

Experiments were performed on Shimadzu DTA-50 thermal analyzer. A sample (~30 mg) of ground crystalline material was sealed in a silica ampoule under vacuum. A similar ampoule of equal mass filled with $Al_2O_3$ was sealed and placed on the reference side of the detector. The sample was heated to 850° C. at 10° C. $min^{-1}$, and after 1 min it was cooled at a rate of −10° C. $min^{-1}$ to 50° C. The residues of the DTA experiments were examined by X-ray powder diffraction. Reproducibility of the results was confirmed by running multiple heating/cooling cycles. The melting and crystallization points were measured at onset of endothermic and exothermic peaks.

3.9. X-Ray Crystallography.

Intensity data were collected in the various range of temperature from 100(2)-500(2) K on a STOE IPDS II and 2T diffractometer with Mo Kα radiation operating at 50 kV and 40 mA with a 34 cm diameter imaging plate. Individual frames were collected with a 4 min exposure time and a 1.0ω rotation. The X-AREA, X-RED, and X-SHAPE software package was used for data extraction and integration and to apply empirical and analytical absorption corrections. The SHELXTL software package was used to solve and refine the structure.

Example 2

Synthesis and Characterization of Organic-Inorganic Hybrid Metal Halides

Experimental

Synthesis.

Sn granules, $I_2$(99.8%), $HC(NH_2)_2Cl$ (98%), $Pb(NO_3)_2$ (99.999%), KI (99.0%) and CsI (99.95%) solids and distilled HI 57% (99.95%), $H_3PO_2$ 50% and $CH_3NH_2$ 40% aqueous solutions and MeONa 25% methanolic solution were purchased from Sigma-Aldrich.

SnI$_2$ was prepared, as follows. A 3-necked 500 mL round bottom flask was charged with 50 g granulated Sn and 300 mL of 2M aqueous HCl was added. The mixture was flushed with N$_2$ for 1-2 min. 70 g of I$_2$ were added in two portions. The solution turned to dark brown. The flask was immersed in a silicon oil bath heated to 170° C. and attached to a condenser. At this point the N$_2$ flow should be at a minimum, in order to avoid I$_2$ fumes to escape or crystallize inside the condenser. When the atmosphere inside the flask was free of I$_2$ vapors, 50 mL of 2M HCl was added, to transfer the quantity of I$_2$ that has crystallized inside the condenser back into the flask. At this point, the N$_2$ flow was increased slightly. As the reaction proceeded the color of the solutions changed progressively to red and finally to yellow. When the color of the solution turned yellow (took 60-120 minutes), Sn was added to the mixture at 15 min time intervals in ~1 g batches. This was because it was necessary to remove any traces of I$_2$ or, less likely, O$_2$ present. The reaction was judged to be complete when the color of the solution was bright yellow and the Sn added retained its luster for 15 minutes. The yellow solution was transferred by decantation (since Sn is granulated filtering was not required) to a 500 mL 2-necked flask, which was immersed in a water bath heated at 70° C. under a flow of N$_2$. The hot yellow solution was slowly brought to ambient temperature and the first crystals of SnI$_2$ crystallized as long red needles. This cooling step encouraged the formation of larger crystals which facilitate the isolation of the material. The precipitation was complete on standing overnight. After 1 day, large red needles of SnI$_2$ were formed. The product was isolated either by filtration, followed by copious washing with 0.01M degassed HCl and drying in a vacuum oven at 50° C., or through evaporation to dryness at 70° C. The yield was 90-100 g (90-99% based on total I$_2$) of pure SnI$_2$. The dried solid had a bright red color and was stable on standing in dry air for several weeks. Combined action of oxygen and water on the material resulted in rapid oxidation to orange SnI$_4$, while distilled water caused hydrolysis to white Sn(OH)$_2$.

PbI$_2$ was prepared by mixing aqueous solutions of Pb(NO$_3$)$_2$ and KI in 1:2 molar ratio. CH$_3$NH$_3$I was prepared by neutralizing equimolar amounts of HI and aqueous CH$_3$NH$_2$. HC(NH$_2$)$_2$I was prepared by neutralizing EtOH solutions of HC(NH)(NH$_2$) (prepared by neutralizing HC(NH$_2$)$_2$Cl with MeONa in MeOH and discarding NaCl) with aqueous HI. The purity of the materials was confirmed by powder diffraction measurements.

A) Solution Synthesis.

General Procedure:

A 100 ml 2-necked round bottom flask was charged with a mixture of aqueous HI (6.8 ml, 7.58M) and aqueous H$_3$PO$_2$ (1.7 ml, 9.14M). The liquid was degassed by passing a stream of nitrogen through it for 1 min and keeping it under a nitrogen atmosphere throughout the experiment. SnI$_2$ (372 mg, 1 mmol) or PbI$_2$ (462 mg, 1 mmol) was dissolved in the mixture upon heating the flask to 120° C. using an oil bath, under constant magnetic stirring, forming a bright yellow solution.

CH$_3$NH$_3$SnI$_3$ (1):

A 100 ml 2-necked round bottom flask was charged with a mixture of aqueous HI (6.8 ml, 7.58M) and aqueous H$_3$PO$_2$ (1.7 ml, 9.14M). The liquid was degassed by passing a stream of nitrogen through it for 1 min and keeping it under a nitrogen atmosphere throughout the experiment. SnI$_2$ (372 mg, 1 mmol) was dissolved in the mixture upon heating the flask to 120° C. using an oil bath, under constant magnetic stirring, forming a bright yellow solution. To the hot yellow solution was added solid CH$_3$NH$_3$I (159 mg, 1 mmol) which dissolved immediately. The solution was evaporated to approximately half its original volume by heating at 120° C. The stirring was discontinued and the solution was left to cool back to room temperature. Upon cooling, black, elongated, rhombic dodecahedral (12 faces) crystals of the title compound were precipitated. The crystals were left to grow inside the mother liquor for a further 24 h under a nitrogen atmosphere before being filtered and washed copiously with degassed EtOH. Yield 70-90%. (Diffuse-Reflectance Infrared Fourier Transformed spectroscopy, DRIFT) KBr: 3393br, 3191br, 2961w, 2925w, 2855w, 1623s, 1471m, 1383w, 1320w, 1260m, 1124s, 1061s, 806w, 566w. On exposure to the atmosphere, the lustrous black crystals developed some irredesence on their surface in the first few minutes of exposure before gradually converting into black/greenish dull solid after approximately 24 h.

HC(NH$_2$)$_2$SnI$_3$ (2):

A 100 ml 2-necked round bottom flask was charged with a mixture of aqueous HI (6.8 ml, 7.58M) and aqueous H$_3$PO$_2$ (1.7 ml, 9.14M). The liquid was degassed by passing a stream of nitrogen through it for 1 min and keeping it under a nitrogen atmosphere throughout the experiment. SnI$_2$ (372 mg, 1 mmol) was dissolved in the mixture upon heating the flask to 120° C. using an oil bath, under constant magnetic stirring, forming a bright yellow solution. To the hot yellow solution was added solid HC(NH$_2$)$_2$I (172 mg, 1 mmol), which dissolved immediately. The solution was evaporated to approximately half its original volume by heating at 120° C. The stirring was discontinued and the solution was left to cool back to room temperature. Upon cooling, black rhombic dodecahedral crystals (12 faces) of the title compound were precipitated. The crystals were left to grow inside the mother liquor for a further 24 h under a nitrogen atmosphere before being filtered and washed copiously with degassed EtOH. Yield 70-90%. DRIFT, KBr: 3402br, 3269br, 2926w, 2925w, 1714s, 1624w, 1400m, 1111m, 1065s, 810, 598w. On exposure to the atmosphere, the lustrous black crystals developed some irredesence on their surface in the first few minutes of exposure before gradually converting into black/greenish dull solid after approximately 24 h.

CH$_3$NH$_3$PbI$_3$ (3):

A 100 ml 2-necked round bottom flask was charged with a mixture of aqueous HI (6.8 ml, 7.58M) and aqueous H$_3$PO$_2$ (1.7 ml, 9.14M). The liquid was degassed by passing a stream of nitrogen through it for 1 min and keeping it under a nitrogen atmosphere throughout the experiment. PbI$_2$ (462 mg, 1 mmol) was dissolved in the mixture upon heating the flask to 120° C. using an oil bath, under constant magnetic stirring, forming a bright yellow solution. To the hot yellow solution was added solid CH$_3$NH$_3$I (159 mg, 1 mmol), which dissolved immediately. The solution was evaporated to approximately half its original volume by heating at 120° C. The stirring was discontinued and the solution was left to cool back to room temperature. Upon cooling, black, rhombic dodecahedral crystals (12 faces) of the title compound precipitated. The crystals were left to grow inside the mother liquor for a further 24 h under a nitrogen atmosphere before being filtered and washed copiously with anhydrous EtOH. Yield 70-90%. DRIFT, KBr: 3529br, 3180br, 2956w, 2925w, 2711w, 1599s, 1471m, 1250m, 1056m, 960m, 910m, 492m. The crystals were insensitive on exposure to the atmosphere but spontaneously hydrolyzed to yellow PbI$_2$ upon wetting in H$_2$O. They retained their luster for several weeks, after which time their surface becomes dull, without, however, affecting the integrity of the solid.

HC(NH$_2$)$_2$PbI$_3$ (4a):

A 100 ml 2-necked round bottom flask was charged with a mixture of aqueous HI (6.8 ml, 7.58M) and aqueous H$_3$PO$_2$ (1.7 ml, 9.14M). The liquid was degassed by passing a stream of nitrogen through it for 1 min and keeping it under a nitrogen atmosphere throughout the experiment. $PbI_2$ (462 mg, 1 mmol) was dissolved in the mixture upon heating the flask to 120° C. using an oil bath, under constant magnetic stirring, forming a bright yellow solution. To the hot solution was added solid $HC(NH_2)_2I$ (172 mg, 1 mmol), which dissolved immediately. The solution was evaporated to approximately half its original volume by heating at 120° C. The stirring was discontinued and the solution was left at 100° C. to evaporate slowly. Black hexagonal (8 faces) or trigonal (5 faces) crystals of the title compound were precipitated and grown at this temperature. After standing for 2-3 h at 100° C., under a nitrogen atmosphere, the temperature was set to 80° C. for a further 2-3 h. The step was repeated two more times to reach 60° C. and 40° C. at which point the solution was left to come to room temperature by powering off the hotplate. The crystals were collected by filtration and washed copiously with anhydrous EtOH. Yield 50-60%. DRIFT, KBr: 3345br, 2938s, 2858s, 1691s, 1656s, 1543m, 1139s, 1066s, 608m, 430w. Upon exposure to the atmosphere, at ambient temperature, the compound totally converts to 4b within 1 h. Hydrolyses in water to $PbI_2$.

$HC(NH_2)_2PbI_3$ (4b):

A 100 ml 2-necked round bottom flask was charged with a mixture of aqueous HI (6.8 ml, 7.58M) and aqueous $H_3PO_2$ (1.7 ml, 9.14M). The liquid was degassed by passing a stream of nitrogen through it for 1 min and keeping it under a nitrogen atmosphere throughout the experiment. $PbI_2$ (462 mg, 1 mmol) was dissolved in the mixture upon heating the flask to 120° C. using an oil bath, under constant magnetic stirring, forming a bright yellow solution. To the hot yellow solution was added solid $HC(NH_2)_2I$ (172 mg, 1 mmol), which dissolved immediately. The solution was evaporated to approximately half its original volume by heating at 120° C. The stirring was discontinued and the solution was left at 100° C. to evaporate slowly. Black hexagonal (8 faces) or trigonal (5 faces) crystals were precipitated. At that point, heating was discontinued and the mixture was cooled to room temperature. After 4-5 h the black crystals fully converted to yellow ones of essentially the same shape. The yellow crystals were collected by filtration and washed copiously with anhydrous EtOH. Yield 50-60%. The crystals were insensitive on exposure to the atmosphere but spontaneously hydrolyzed to yellow $PbI_2$ upon wetting in $H_2O$.

$CH_3NH_3Sn_{1-x}Pb_xI_3$ solid solutions (5):

A 100 ml 2-necked round bottom flask was charged with a mixture of aqueous HI (6.8 ml, 7.58M) and aqueous $H_3PO_2$ (1.7 ml, 9.14M). Mixtures of $SnI_2$ (279 mg, 0.75 mmol, 5a; 186 mg, 0.50 mmol, 5b; and 93 mg, 0.25 mmol, 5c), and $PbI_2$ (116 mg, 0.25 mmol, 5a; 231 mg, 0.50 mmol, 5b; and 347 mg, 0.75 mmol, 5c) were dissolved, forming a bright yellow solution which was heated to 120° C. using an oil bath. To the hot solution was added solid $CH_3NH_3I$ (159 mg, 1 mmol), which dissolved immediately. The solution was evaporated to approximately half its original volume by heating at 120° C. The stirring was discontinued and the solution was left to cool back to room temperature. Upon cooling, black, rhombic dodecahedral crystals (12 faces) or truncated octahedral (14 faces), depending on the crystallization temperature or/and the composition, precipitated. The crystals were left to grow inside the mother liquor for a further 24 h under a nitrogen atmosphere before being filtered and washed copiously with degassed EtOH. The solid solutions reflected the properties of their parent compounds. Sn-containg solids were air sensitive and Pb-containing ones were readily hydrolyzable.

$CsSnI_3$ (6a):

A 100 ml 2-necked round bottom flask was charged with a mixture of aqueous HI (6.8 ml, 7.58M) and aqueous $H_3PO_2$ (1.7 ml, 9.14M). The liquid was degassed by passing a stream of nitrogen through it for 1 min and keeping it under a nitrogen atmosphere throughout the experiment. $PbI_2$ (462 mg, 1 mmol) was dissolved in the mixture upon heating the flask to 120° C. using an oil bath, under constant magnetic stirring, forming a bright yellow solution. To the hot yellow solution was added solid CsI (260 mg, 1 mmol), which dissolved immediately. 2 min after the addition of the yellow needle-shaped crystals started to precipitate. The stirring was discontinued and the solution was left to cool to room temperature. The crystals were left to grow inside the mother liquor for a further 24 h under a nitrogen atmosphere before being filtered and washed copiously with degassed EtOH. With this sample there was almost always a $Cs_2SnI_6$ (9b) impurity which formed spontaneously upon addition of solid CsI into the solution. Pure yellow needles can be obtained by adding a solution of CsI in 1 mL of concentrated HI over the course of 2 min. Yield 80-90%. The compound was air sensitive as demonstrated by the full conversion of the yellow crystals into a black solid within 24 h. The black solid is 6b.

$Cs_2SnI_6$ (6b):

A 100 ml 2-necked round bottom flask was charged with a mixture of aqueous HI (6.8 ml, 7.58M) and aqueous $H_3PO_2$ (1.7 ml, 9.14M). The liquid was degassed by passing a stream of nitrogen through it for 1 min and keeping it under a nitrogen atmosphere throughout the experiment. $SnI_2$ (372 mg, 1 mmol) was dissolved in the mixture upon heating the flask to 120° C. using an oil bath, under constant magnetic stirring, forming a bright yellow solution. To the hot yellow solution was added solid CsI (260 mg, 1 mmol), which dissolved immediately. 2 min after the addition of the yellow needle-shaped crystals started to precipitate. The precipitate was dissolved by adding 10 mL of acetone, producing a dark red solution. After 5 min the stirring was discontinued and the solution was left to cool to room temperature. Black truncated octahedral (14 faces) crystals were formed upon standing. The crystals were left to grow inside the mother liquor for a further 24 h under a nitrogen atmosphere before being filtered and washed with degassed EtOH. Yield 80-90%. The compound is air- and water-stable. It formed black aqueous solutions which decomposed only slowly to deposit white $SnO_2$ and deep red $I_3^-$ solutions.

$CsPbI_3$ (7):

A 100 ml 2-necked round bottom flask was charged with a mixture of aqueous HI (6.8 ml, 7.58M) and aqueous $H_3PO_2$ (1.7 ml, 9.14M). The liquid was degassed by passing a stream of nitrogen through it for 1 min and keeping it under a nitrogen atmosphere throughout the experiment. $PbI_2$ (462 mg, 1 mmol) was dissolved in the mixture upon heating the flask to 120° C. using an oil bath, under constant magnetic stirring, forming a bright yellow solution. To the hot yellow solution was added solid CsI (260 mg, 1 mmol), which dissolved immediately, producing a yellow precipitate. The precipitate was redissolved by adding the minimum required amount of acetone ~5 mL. Stirring was discontinued and the solution was left to cool to room temperature. Yellow needle-shaped crystals were formed upon standing. The crystals were left to grow inside the mother liquor for a further 24 h under a nitrogen atmosphere before being filtered and washed copiously with anhydrous EtOH. Yield 80-90%. The compound was insensitive to air but it hydrolyzed spontaneously.

B) Solid State Reactions

1) Sealed Tube Preparations:

Equimolar amounts of $MI_2$ and AI were loaded in a 9 mm pyrex tube. Typically, the scale is 1 mmol based on the Sn or Pb halide. The materials were shaken mechanically to ensure a homogenous mixture. The tube was placed on a sealing line, evacuated to $10^{-4}$ mbar, and flame sealed. The tube was immersed on a sand bath standing a 200° C., in such a way that the mixture of solids was heated homogeneously. About 4/5 of the tube was maintained outside the bath at room temperature. The solids were left in the bath for 2 h forming a homogeneous black solid. The Sn-containing solids were air sensitive whereas the Pb-containing ones were air stable. No obvious color changes were observed.

2) Open Tube Preparations:

Equimolar amounts of $MI_2$ and AI were loaded in a 15 mm pyrex test tubes. The materials were shaken mechanically to ensure a homogenous mixture. The tube was immersed in a sand bath standing at 350° C. under a gentle flow of nitrogen. The reaction proceeded within 0.5-1 min. The formation of a homogeneous black melt signaled the end of the reaction. Upon melting the tube was removed from the bath and left to cool in air, usually producing a shiny black ingot. The melt was formed for the Sn-containing compounds only. Pb-containing solids decomposed on prolonged heating (>3 min) or by raising the temperature above 400° C., through evolution of $I_2$ gas, crystallizing on the cooler walls of the tube. The shiny black ingots of the Sn-containing compounds were gradually converted into dull black/greenish solids within 24 h.

3) Room Temperature Solid State Preparations:

Equimolar amounts of $MI_2$ and AI were placed in an agate mortar and ground carefully with a pestle until a visually homogeneous, black powder was obtained. The Sn-containing solids were air sensitive whereas the Pb-containg ones were air stable. No obvious color changes were observed.

Characterization.

Thermal Analysis:

The Thermogravimetric Analysis (TGA) measurements were performed on a Shimadzu TGA-50 thermogravimetric analyzer in aluminum boats under a $N_2$ flow. Differential Thermal Analysis (DTA) was performed on a Shimadzu DTA-50 thermal analyzer in aluminum boats using $\alpha$-$Al_2O_3$ in identical aluminum boats as a reference, under a $N_2$ flow. Differential Scanning calorimetry (DSC) measurements were performed on a DSC-60 calorimeter in aluminum boats using identical aluminum boats as a reference. The temperature range studied was 20-500° C.

Scanning Electron Microscopy (SEM):

Semiquantitative microprobe analyses and energy-dispersive spectroscopy (EDS) were performed with a Hitachi S-3400 scanning electron microscope equipped with a PGT energy-dispersive X-ray analyzer. Data were acquired with an accelerating voltage of 20 kV.

Optical Spectroscopy:

Optical diffuse-reflectance measurements were performed at room temperature using a Shimadzu UV-3101 PC double-beam, double-monochromator spectrophotometer operating from 200 to 2500 nm. $BaSO_4$ was used as a non-absorbing reflectance reference. A Nicolet 6700 IR spectrometer equipped with a diffuse-reflectance kit was used for the 4000-400 $cm^{-1}$ spectral region. The spectrum was referenced towards a metallic mirror used as the non-absorbing reflectance standard. The generated reflectance-versus-wavelength data were used to estimate the band gap of the material by converting reflectance to absorbance data according to the Kubelka-Munk equation: $\alpha/S=(1-R)^2/2R$, where R is the reflectance and R and S are the absorption and scattering coefficients, respectively.

Photoluminescence Measurements:

The samples were measured using an OmniPV Photoluminescence system, equipped with a DPSS frequency-doubling Nd:YAG laser (500 mW power output, class 4) emitting at 532 nm coupled with a bundle of 8 400 $\mu$m-core optical fibers as an excitation source. The emission was measured in the 200-1700 nm range with two StellarNet spectrometers, covering the 200-850 nm (CCD) and 900-1700 nm (InGaAs) areas, coupled with 400 $\mu$m-core optical fibers and integrated within the bundle (10 optical fibers total). The backscattered light was collected at ~180° angle at 3 mm from the sample. For estimating the intensity of the signal and also to account for the excitation beam fluctuations, a disk of single-crystalline InP (930 nm emission peak) was measured before and after the sample measurements. The excitation time used was 100 ms and the data were averaged for 5 independent scans. The data were analyzed using the SpectraWiz or the OmniPV PL software.

Vibrational Spectroscopy:

Fourier-transformed infrared spectra (FT-IR) were recorded on a Nicolet 6700 IR spectrometer in the 400-4000 $cm^{-1}$ spectral region using a diffuse-reflectance kit. The measurement was conducted under a constant flow of nitrogen. The spectrum is referenced towards a metal mirror used as the 100% reflectance standard.

Charge Transport Properties:

a) Low Temperature Resistivity measurements

Four-probe low temperature measurements were performed on a Quantum Design PPMS device in 5-330K temperature range using the four-probe technique on well-defined rhombic dodecahedral single-crystals grown from the solution method. Current was applied on a rhombic face of the crystal and the voltage was measured on two of the apices of the polyhedron (c-axis). The resistance was recorded as an average of both negative and positive current polarities.

b) High Temperature Resistivity and Seebeck Coefficient and Hall-Effect Measurements Four-probe room and high temperature measurements were performed in the 300-550K range. Measurements were made for arbitrary current directions in the ab-plane using standard point contact geometry. A home-made resistivity apparatus equipped with a Keithley 2182A nanovoltmeter, Keithley 617 electrometer, Keithley 6220 Precision direct current (DC) source, and a high temperature vacuum chamber controlled by a K-20 MMR system was used. Data acquisition was controlled by custom written software.

Seebeck measurements were performed in the 300-400K temperature range on the same home-made apparatus using Cr/Cr:Ni thermocouples as electric leads that were attached to the sample surface by means of colloidal graphite isopropanol suspension. The temperature gradient along the crystal was generated by a resistor on the 'hot' side of the crystal. The data were corrected for the thermocouple contribution using a copper wire. Data acquisition was controlled by custom written software.

Powder X-Ray Diffraction Studies:

Powder X-ray diffraction measurements were performed using a silicon-calibrated CPS 120 INEL powder X-ray diffractometer (Cu K$\alpha$, 1.54056 A°) graphite monochromatized radiation) operating at 40 kV and 20 mA, equipped with a position-sensitive detector with a flat sample geometry.

Single Crystal X-Ray Diffraction Studies:

Single-crystal X-ray diffraction experiments were performed using either a STOE IPDS II or IPDS 2T diffractometer using Mo Kα radiation (λ=0.71073 A°) and operating at 50 kV and 40 mA. Integration and numerical absorption corrections were performed using the X-AREA, X-RED, and X-SHAPE programs. All structures were solved by direct methods and refined by full-matrix least squares on $F^2$ using the SHELXTL program package. The TwinRotMat, Rotax and other PLATON functions of the WinGX platform were used to identify the twinning domains and the correct space group, respectively, for the low temperature crystal structures. The JANA2006 software was employed for the refinement of the multiple twinning domains present at low temperature structures. The ISOTROPY software was used to calculate the group-subgroup relationships of the perovskite structures and to find the correct space group.

Results and Discussion.

Synthetic Aspects:

The synthesis of the materials can be accomplished using a variety of approaches. This includes "crude" methods such as direct mortar and pestle grinding of starting materials at room temperature in air, high temperature fusion of the precursors in silica tubes and solution growth of single crystals. All methods produce the title compounds, though the purity and properties of the resulting materials vary significantly with the method of synthesis. The $CsMI_3$ analogues were also prepared and used as reference materials for comparison with the $AMI_3$ systems.

The materials obtained from the grinding method usually were a mixture of products, the main phase (visually homogeneous black solid) being the desired perovskite, with significant amounts of unreacted precursors as evidenced by the X-ray powder patterns of the solids. This method was fast and efficient and is the method of choice to observe the unusual optical properties of each compound. The solids obtained through this method consistently produced the most intense room temperature photoluminescence signal, presumably due to the large degree of defects present or due to interface effects (vide infra).

Another method that gives the perovskite phases quickly was by heating the starting materials together at ~350° C. in air or under a gentle flow of nitrogen. A pure black melt was obtained in all cases after 0.5-1 min and on solidification produced a shiny black material. It is imperative to keep the reaction time short to prevent the volatilization $CH_3NH_3I$ and $SnI_4$. The latter can be seen on the cooler parts of the tube as an orange liquid. $HC(NH_2)_2I$ also decomposes at that temperature to the volatile sym-triazine and $NH_4I$. The materials prepared in this fashion were obtained in higher yield compared to the ones prepared at room temperature by grinding but the presence of oxidation products (i.e., $SnI_4$) and the loss of some of the organic cation rendered these materials defective, not following the exact stoichiometry. The presence of oxidized impurities was evident by thermogravimetric analysis (to be discussed in detail later) by following the mass loss anomalies in the 150-200° C., where $SnI_4$ was expected to melt and volatilize. For comparison, the Pb compounds did not show any mass loss in this region ($PbI_4$ was not known). Instead, the oxidation mechanism on prolonged heating for the Pb solids (in air) produced purple vapor of $I_2$ with subsequent formation of PbO in the solid.

Using solid state techniques we were able to isolate the materials in pure form by grinding the precursors together, followed by subsequent annealing at 200° C. inside vacuum-sealed pyrex tubes for ~2 h. Again, some condensation was seen on the cooler parts of the tube (mainly formation of the white organic iodide salt and/or orange $SnI_4$ crystals in Sn-containing compounds at the sand bath-air interface) therefore the materials prepared by this method were expected to be stoichiometrically defective as well, but contain no oxidation byproducts compared to those from the open tube methods.

The method of choice to obtain pure materials with more exact stoichiometries was the solution method. Through this route we were able to obtain high quality single crystals that allowed X-ray crystal structure characterization. The crystals of the obtained materials were well defined a could be modified depending on the temperature profile of the precipitation. Namely, the products vary from polycrystalline aggregates when precipitation started at elevated temperatures (ca. 130° C.) under vigorous stirring to discrete polyhedral crystals when crystallization occurred by cooling slowly to room temperature. The crystals had a strong tendency towards a rhombic dodecahedral geometry, in general, though each phase adopted a unique habit; thus, 1 and 3 adopted the elongated rhombic dodecahedron (rhombo-hexagonal dodecahedron) shape, 2 adopted a more regular rhombic dodecahedron, while 4a adopted the hexagonal prism shape.

The materials obtained from the aqueous $HI/H_3PO_2$ solution mixture were exceptionally pure as judged by XRD. This was mainly attributed to the reducing nature of phosphinic acid which was sufficient to suppress any oxidation occurring by reducing $I_3^-$ (formed by aerial oxidation of the solution) back to $I^-$. This was evident from the disappearance of the dark red color of the triiodide ion from solution (when oxidation occurred) which turned bright yellow when treated with phosphinic acid. The purging effects of phosphinic acid ensured that no stray oxidation products were present during precipitation, while no traceable byproducts were found as a result of the presence of $H_3PO_2/H_3PO_3$ species in the reaction mixture. In most cases the sole product of the reaction was a pure black crystalline phase. Interestingly, in the case of $HC(NH_2)_2PbI_3$ we were able to isolate two isomers; a black perovskite phase (4a) and a yellow hexagonal phase (4b) having a different crystal structure. It appears that the black phase 4a is stable at high temperatures (>60° C.) while at lower temperatures the black phase fully converts to yellow phases inside the mother liquor. When the products are separated from the solvent and dried they interconvert only slowly.

A complication that occurred when trying to isolate pure 4a, was the partial decomposition of formamidine to ammonia and sym-triazine in the strongly acidic reaction media using a prolonged reaction time. Whereas the sym-triazine did not interfere in the reaction, the ammonium cation slightly complicates the reaction. $NH_4PbI_3^-2H_2O$, occurring as pale yellow needles, or, as yellow needles, could be detected in 4 as an impurity. The effect can be minimized by keeping the reaction time as short as possible and by avoiding temperatures >150° C.

It is important to point out that in the case of the Cs analogs $CsSnI_3$ and $CsPbI_3$ the solution method cannot be employed for the preparation of the black forms of these phases and the yellow phases are isolated instead. The yellow modifications of $CsSnI_3$ (6a) and $CsPbI_3$ (7), are isostructural and crystallized in long, thin, needle-shaped crystals, in accordance with the 1-D structure of these materials. The solution method was also capable of producing the black $Cs_2Sn^{IV}I_6$ phase (6b) an oxidized byproduct in the synthesis of $CsSnI_3$ with a molecular salt structure.

The stability of the materials in air varied. The Pb-containing phases were stable in air for months, though they were affected by humidity and lost their crystalline luster after a couple of weeks. However, this was only a surface effect since the bulk properties of the materials were retained. The Sn-containing materials were air and moisture sensitive and partially decomposed within 2 h before total decomposition after 1 d; this behavior was detected in the powder diffraction pattern evolution over time, from the patterns showing the appearance of extra Bragg diffraction peaks that belonged to the oxidized $Sn^{IV}$ species, $(CH_3NH_3)_2SnI_6$, as judged by comparing the diffraction pattern of the unindexed peaks with those of $Cs_2SnI_6$. A general trend observed was that methylammonium-containing materials were considerably more stable than formamidinium-containing ones. This reflects the respective stability of the cations themselves and particularly the tendency of $HC(NH_2)_2^+$ to dissociate to ammonia and sym-triazine.

Structure Description.

Single crystals of the materials obtained from the solution method were analyzed by single crystal X-ray diffraction studies. The diffraction measurements were performed at room temperature, and in the range 100-400 K to determine the structural changes that occur during the several phase transitions. The presence of phase transitions is consistent with the perovskite nature of the materials. The common trend for 1-4 was that there were two phase transitions that took place, leading to three distinct structural modifications. These were classified as, the high temperature α-phase, the intermediate temperature β-phase and the low temperature γ-phase, while the non-perovskite yellow phase is termed the δ-phase for consistency with the nomenclature used in the studies of $CsSnI_3$. The δ-phase denotes an 1D array of octahedra and it occurs in δ-$HC(NH_2)_2PbI_3$(4b).

α-Phase Structures:

The α-phase for 1 and 2 was found at room temperature and consisted of pseudo-cubic unit cell with lattice parameter being a=6.2307 Å and a=6.3290 Å, respectively. The α-phase for 3 was also pseudo-cubic and formed after a phase transition that occurred at temperature >50° C. with lattice parameter a=6.3130 Å. Compound 4a was unique in adopting a trigonal phase with a=8.9817 Å and c=11.0060 Å at room temperature. We are as yet uncertain if this is the α-phase for 4a or if there is yet another higher symmetry phase at higher temperatures. For simplicity, here we refer to 4a as the α-phase.

Because phase transitions affect the photoluminescence properties of $CsSnI_3$ (which adopts the orthorhombic γ-phase at room temperature), we decided to investigate the phase transitions that occur in the present hybrid perovskites at different temperatures. The main difference between $CsMI_3$ inorganic perovskites and the organic hybrid perovskites is the possibility of obtaining the ideal cubic Pm-3m structure. Whereas in the case of $Cs^+$ a single atom occupies the 1b Wyckoff position in the center of the cube of the perovskite structure in a primitive unit cell, in the cases of $CH_3NH_3^+$ and $HC(NH_2)_2^+$ this is not possible in this space group. As a consequence, these cations tend to be disordered in the cage. In a cubic unit cell this requires one atom to be placed exactly on the special position and the other(s) to be disordered around the 12 possible orientations inside the cube. Such a situation is not particularly appealing on chemical grounds, especially if one considers the hydrogen bonding capabilities of both $CH_3NH_3^+$ and $HC(NH_2)_2^+$. Moreover, when a polar organic cation is confined inside the cage its dipole moment cannot be cancelled out, thus inducing non-centrosymmetric domains in the crystal.

With this in mind, in our consideration of the crystal structure determinations when an ambiguity occurs we prefer the non-centrosymmetric space group as the correct choice. Of course, when supercells arise from the phase transition an inversion center might emerge which will cancel the dipole moments. At room temperature, the crystal structures of 1-4 are non-centrosymmetric. The space groups that we have found, except for β-$CH_3NH_3PbI_3$ which already has a supercell at this temperature, are classified into the 'ferroelectric distortion' category, which means that they are subgroups of the ideal Pm-3m cubic structure by abolishing certain symmetry elements including the center of symmetry. In this case the symmetry elements are lost as a result of the displacement of the B cation from the center of the octahedron, though the ferroelectric displacement is only marginal. In P4 mm, which is adopted by the higher temperature phase of $CH_3NH_3SnI_3$ and $CH_3NH_3PbI_3$ the displacement occurs along the c-axis (the tetragonal axis), while in Amm2, the space group adopted by $HC(NH_2)_2SnI_3$ at high temperature, the M atom displacement occurs along the a and b axes.

α-$HC(NH_2)_2PbI_3$ is a special case because its space group (centrosymmetric P-3m1) seems to be the parent phase for the family of perovskites termed '1:2 B cation ordering'. The peculiarity arises from the fact that there is only one type of B-cation-Pb. Following this distortion, there are three crystallographically inequivalent Pb cations inside the unit cell.

$CH_3NH_3PbI_3$ adopts the β-phase at room temperature which is distorted (see below) and for this reason we sought to solve the structure of the α-phase using the same specimen by raising the temperature above the reported transition at ~330K. We solved the crystal structure of α-$CH_3NH_3PbI_3$ by measuring a crystal at 400K and found it to be isostructural to α-$CH_3NH_3SnI_3$. For the collection of good datasets we found it essential for the crystal to be maintained at the collection temperature for at least 2 h (to complete the phase transition) before starting the data collection.

β-Phase Structures:

Attempts to determine the crystal structures of the hybrid materials, revealed multiple twinning on lowering of crystallographic symmetry. This happens when moving from high to low symmetry distorting the unit cell. In order for the crystal to comply with such a distortion it "splits" into several domains, a fact that certainly complicates the structure determination. All typical pseudomerohedral twin domains characteristic of the perovskite structure were observed during structure refinement, along the [010], [101) and [121] lattice directions. In all cases the effect was fully reversible and when the temperature was raised the crystal was completely reassembled. Another interesting point here is that when we move from the low to the higher symmetry phase during a phase transition, this effect is not so severe, as it was shown, for example, in the case of $CH_3NH_3PbI_3$. Effectively, this behavior suggests that the transition is smoother on lowering the symmetry and more abrupt when increasing it, a trend that is confirmed by the transport measurements.

The temperature range where the α-phase converts to the β-phase lies between 300-150K for the hybrid perovskites, with the exception of $CH_3NH_3PbI_3$ where the transition takes place at 333K. Lowering of the symmetry is achieved by means of tilting of the octahedra. Pure octahedral tilting starting from an ideal cubic Pm-3m structure follows a specific sequence of descending symmetry leading to a certain set of possible space groups. Such a situation is described using the Glazer notation. This notation describes the distortion about a, b, c axes using the axis symbol accompanied by a '+' or '−' symbol to denote if the tilting between two adjacent polyhedral is in-phase or out-of-phase, respectively. Following the space group sequence for $CsSnI_3$, starting with the ideal Pm-3m structure, it follows a phase transition at ~425K to the tetragonal structure, P4/mbm (double cell volume), before obtaining an orthorhombic structure, Pnma (quadruple volume) below 351K. Such a sequence can be described by considering a pure perovskite tilting model, ignoring ferroelectric-type displacements, with an in-phase distortion along c-axis initially and distortions along the a- and b-axes in the orthorhombic phase. The situation for the hybrid perovskites appears to be different because both ferroelectric and tilting distortions should be taken into consideration. Crystallographic data for the α- and β-phases of 1-4 are given in the three following tables summarizes the crystallographic data for the related compounds 4b, 5b, 6b and 7.

Crystallographic Data of the α-phases for 1-4

| | Compound | | | |
|---|---|---|---|---|
| | α-CH$_3$NH$_3$SnI$_3$ (1) | α-HC(NH$_2$)$_2$SnI$_3$ (2) | α-CH$_3$NH$_3$PbI$_3$ (3) | α-HC(NH$_2$)$_2$PbI$_3$ (4a) |
| Temperature | 293(2) K | 340(2) K | 400(2) K | 293(2) K |
| Crystal system | Tetragonal | Orthorhombic | Tetragonal | Trigonal |
| Space group | P4mm | Amm2 | P4mm | P3m1 |
| Unit cell dimensions | a = 6.2302(10) Å, α = 90.00° b = 6.2302(10) Å, β = 90.00° c = 6.2316(11) Å, γ = 90.00° | a = 6.3286(10) Å, α = 90.00° b = 8.9554(11) Å, β = 90.00° c = 8.9463(11) Å, γ = 90.00° | a = 6.3115(2) Å, α = 90.00° b = 6.3115(2) Å, β = 90.00° c = 6.3161(2) Å, γ = 90.00° | a = 8.9817(13) Å, α = 90.00° b = 8.9817(13) Å, β = 90.00° c = 11.006(2) Å, γ = 120.00° |
| Volume | 241.88(7) Å$^3$ | 507.03(12) Å$^3$ | 251.60(2) Å$^3$ | 768.9(2) Å$^3$ |
| Z | 1 | 2 | 1 | 3 |
| Density (calculated) | 3.649 g/cm$^3$ | 3.566 g/cm$^3$ | 4.092 g/cm$^3$ | 4.101 g/cm$^3$ |
| Absorption coefficient | 12.128 mm$^{-1}$ | 11.579 mm$^{-1}$ | 25.884 mm$^{-1}$ | 25.417 mm$^{-1}$ |
| F(000) | 228 | 468 | 260 | 798 |
| Crystal size (mm$^{-3}$) | 0.053 × 0.032 × 0.021 | 0.176 × 0.163 × 0.136 | 0.035 × 0.022 × 0.017 | 0.041 × 0.026 × 0.021 |
| θ range | 3.27 to 28.94° | 3.22 to 29.11° | 3.23 to 24.92° | 1.85 to 29.19° |
| Index ranges | −8 <= h <= 8, −8 <= k <= 8, −8 <= l <= 8 | −8 <= h <= 8, −10 <= k <= 12, −12 <= l <= 10 | −7 <= h <= 7, −6 <= k <= 6, −7 <= l <= 7 | −12 <= h <= 12, −12 <= k <= 11, −15 <= l <= 15 |
| Reflections collected | 2164 | 2490 | 1628 | 7475 |
| Independent reflections | 411 [R$_{int}$ = 0.0458] | 686 [R$_{int}$ = 0.0517] | 300 [R$_{int}$ = 0.0700] | 1645 [R$_{int}$ = 0.0459] |
| Completeness to θ | θ = 28.94°, 98.2% | θ = 29.11°, 100% | θ = 24.92°, 98.2% | θ = 29.19°, 99.6% |
| Data/restr./param. | 411/2/16 | 686/3/24 | 300/2/19 | 1645/7/44 |
| Goodness-of-fit | 1.262 | 0.861 | 1.176 | 0.908 |
| Final R indices [>2σ(I)] | R$_{obs}$ = 0.0327, wR$_{obs}$ = 0.0576 | R$_{obs}$ = 0.0323, wR$_{obs}$ = 0.0577 | R$_{obs}$ = 0.0417, wR$_{obs}$ = 0.0981 | R$_{obs}$ = 0.0398, wR$_{obs}$ = 0.0666 |
| R indices [all data] | R$_{all}$ = 0.0451, wR$_{all}$ = 0.0613 | R$_{all}$ = 0.0615, wR$_{all}$ = 0.0632 | R$_{all}$ = 0.0417, wR$_{all}$ = 0.0981 | R$_{all}$ = 0.0892, wR$_{all}$ = 0.0807 |
| 2$^{nd}$ twin domain | [−1 0 0 0 0 1 0 1 0] 49(69)% | [0 −½ −½ −1 −½ −½ −1 ½ −½] 43(3)% | [−1 0 0 0 1 0 1 0] 36(3)% | [−1 0 0 0 −1 0 0 0 1] 6.36(2)% |
| Flack parameter | [−1 0 0 0 −1 0 0 0 −1] −4(45)% | [−1 0 0 0 −1 0 0 0 −1] −50(32)% | [−1 0 0 0 −1 0 0 0 −1] 12(3)% | [−1 0 0 0 −1 0 0 0 −1] 20(15)% |
| 2$^{nd}$ domain Flack parameter | [1 0 0 0 1 0 1 0] 3(68)% | [0 −½ −½ −½ −1 ½ ½ −1 ½] 13(3)% | [1 0 0 0 1 0 1 0] 37(4)% | not refined |
| Extinction coefficient | — | 0.0200(4) | 0.016(2) | — |
| Largest diff. peak/hole | 0.895/−0.861 e.Å$^{-3}$ | 0.394/−0.952 e.Å$^{-3}$ | 1.871/−2.008 e.Å$^{-3}$ | 1.104/−1.727 e.Å$^{-3}$ |
| Wavelength | 0.71073 Å | | | |
| Refinement method | Full-matrix least-squares on F$^2$ | | | |

R = Σ||F$_o$| − |F$_c$||/Σ|F$_o$|, wR = {Σ[w(|F$_o$|$^2$ − |F$_c$|$^2$)$^2$]/Σ[w(|F$_o$|$^4$)]}$^{1/2}$ and calc
w = 1/[σ$^2$(Fo$^2$) + (0.0262P)$^2$ + 0.0000P] where P = (Fo$^2$ + 2Fc$^2$)/3

Crystallographic Data of the β-phases for 1-4

| | Compound | | | |
|---|---|---|---|---|
| | β-CH$_3$NH$_3$SnI$_3$ (1) | β-HC(NH$_2$)$_2$SnI$_3$ (2) | β-CH$_3$NH$_3$PbI$_3$ (3) | β-HC(NH$_2$)$_2$PbI$_3$ (4a) |
| Temperature | 200(2) K | 180(2) K | 293(2) K | 150(2) K |
| Crystal system | Tetragonal | Orthorhombic | Tetragonal | Trigonal |
| Space group | I4cm | Imm2 | I4cm | P3 |
| Unit cell dimensions | a = 8.7577(15) Å, α = 90.00° b = 8.7577(15) Å, β = 90.00° c = 12.429(3) Å, γ = 90.00° | a = 12.5121(9) Å, α = 90.00° b = 12.5171(8) Å, β = 90.00° c = 12.5099(9) Å, γ = 90.00° | a = 8.849(2) Å, α = 90.00° b = 8.849(2) Å, β = 90.00° c = 12.642(2) Å, γ = 90.00° | a = 17.7914(8) Å, α = 90.00° b = 17.7914(8) Å, β = 90.00° c = 10.9016(6) Å, γ = 120.00° |

-continued

| | Compound | | | |
|---|---|---|---|---|
| | β-$CH_3NH_3SnI_3$ (1) | β-$HC(NH_2)_2SnI_3$ (2) | β-$CH_3NH_3PbI_3$ (3) | β-$HC(NH_2)_2PbI_3$ (4a) |
| Volume | 953.2(3) Å$^3$ | 1959.2(2) Å$^3$ | 990.0(4) Å$^3$ | 2988.4(3) Å$^3$ |
| Z | 4 | 8 | 4 | 12 |
| Density (calculated) | 3.703 g/cm$^3$ | 3.692 g/cm$^3$ | 4.159 g/cm$^3$ | 4.221 g/cm$^3$ |
| Absorption coefficient | 12.309 mm$^{-1}$ | 11.986 mm$^{-1}$ | 26.312 mm$^{-1}$ | 26.159 mm$^{-1}$ |
| F(000) | 912 | 1872 | 1040 | 3192 |
| Crystal size (mm$^{-3}$) | 0.158 × 0.111 × 0.089 | 0.018 × 0.014 × 0.009 | 0.005 × 0.003 × 0.002 | 0.038 × 0.030 × 0.023 |
| θ range | 4.65 to 24.94° | 2.30 to 29.15° | 3.26 to 29.03° | 1.87 to 25.00° |
| Index ranges | −9 <= h <= 10, −10 <= k <= 9, −14 <= l <= 14 | −17 <= h <= 17, −17 <= k <= 17, −17 <= l <= 17 | −12 <= h <= 12, −12 <= k <= 10, −16 <= l <= 15 | −21 <= h <= 20, −21 <= k <= 21, −12 <= l <= 12 |
| Reflections collected | 3058 | 9462 | 4483 | 19512 |
| Independent reflections | 521 [$R_{int}$ = 0.1007] | 2876 [$R_{int}$ = 0.0464] | 678 [$R_{int}$ = 0.0664] | 7026 [$R_{int}$ = 0.0596] |
| Completeness to θ | θ = 24.94°, 99.2% | θ = 29.15°, 99.7% | θ = 29.03°, 97.1% | θ = 25.00°, 100% |
| Data/restr./param. | 521/2/21 | 2876/1/47 | 678/2/18 | 7026/18/192 |
| Goodness-of-fit | 1.142 | 0.963 | 1.268 | 0.839 |
| Final R indices [>2σ(I)] | $R_{obs}$ = 0.0637, $wR_{obs}$ = 0.1442 | $R_{obs}$ = 0.0486, $wR_{obs}$ = 0.1276 | $R_{obs}$ = 0.0378, $wR_{obs}$ = 0.0865 | $R_{obs}$ = 0.0656, $wR_{obs}$ = 0.1584 |
| R indices [all data] | $R_{all}$ = 0.0639, $wR_{all}$ = 0.1443 | $R_{all}$ = 0.0780, $wR_{all}$ = 0.1432 | $R_{all}$ = 0.0418, $wR_{all}$ = 0.0879 | $R_{all}$ = 0.1780, $wR_{all}$ = 0.2133 |
| 2$^{nd}$ twin domain | [−½ ½ ½ ½ −½ ½ 1 1 0] 7.9(2)% | [0 0 −1 0 −1 0 −1 0 0] 19.74(6)% | [−1 0 0 0 1 0 0 0 −1] 50(4)% | [−1 0 0 0 −1 0 0 0 1] 94.19(2)% |
| Flack parameter | [−1 0 0 0 −1 0 0 0 −1] −34(23)% | [−1 0 0 0 −1 0 0 0 −1] 9(5)% | [−1 0 0 0 −1 0 0 0 −1] 0(10)% | [−1 0 0 0 −1 0 0 0 −1] 51(5)% |
| 2$^{nd}$ domain Flack parameter | [½ ½ ½ ½ ½ ½ 1 1 0] 16.7(2)% | [0 0 −1 0 1 0 −1 0 0] 23.78(6)% | not refined | not refined |
| Extinction coefficient | 0.00247(6) | 0.000808(18) | — | 0.000498(8) |
| Largest diff. peak/hole | 2.002/−1.194 e.Å$^{-3}$ | 2.606/−1.191 e.Å$^{-3}$ | 0.927/−1.676 e.Å$^{-3}$ | 3.391/−4.496 e.Å$^{-3}$ |
| Wavelength | 0.71073 Å | | | |
| Refinement method | Full-matrix least-squares on F$^2$ | | | |

$R = \Sigma||F_o| - |F_c||/\Sigma|F_o|$, $wR = \{\Sigma[w(|F_o|^2 - |F_c|^2)^2]/\Sigma[w(|F_o|^4)]\}^{1/2}$ and calc
$w = 1/[\sigma^2(Fo^2) + (0.0262P)^2 + 0.0000P]$ where $P = (Fo^2 + 2Fc^2)/3$

40

Crystallographic Data of the β-phases for 4b, 5b, 6b and 7

| | Compound | | | |
|---|---|---|---|---|
| | δ-$HC(NH_2)_2PbI_3$ (4b) | δ-$CH_3NH_3Sn_{0.46}Pb_{0.54}I_3$ (5b) | α-$Cs_2SnI_6$ (6b) | δ-$CsPbI_3$ (7) |
| Temperature | 293(2) K | 293(2) K | 293(2) K | 293(2) K |
| Crystal system | Hexagonal | Tetragonal | Cubic | Orthorhombic |
| Space group | P6$_3$mc | I4cm | Fm-3m | Pnma |
| Unit cell dimensions | a = 8.6603(14) Å, α = 90.00° b = 8.6603(14) Å, β = 90.00° c = 7.9022(6) Å, γ = 120.00° | a = 8.8552(6) Å, α = 90.00° b = 8.8552(6) Å, β = 90.00° c = 12.5353(12) Å, γ = 90.00° | a = 11.6276(9) Å, α = 90.00° b = 11.6276(9) Å, β = 90.00° c = 11.6276(9) Å, γ = 90.00° | a = 10.4342(7) Å, α = 90.00° b = 4.7905(3) Å, β = 90.00° c = 17.7610(10) Å, γ = 90.00° |
| Volume | 513.27(12) Å$^3$ | 982.95(13) Å$^3$ | 1572.1(2) Å$^3$ | 887.78(10) Å$^3$ |
| Z | 2 | 4 | 4 | 4 |
| Density (calculated) | 4.096 g/cm$^3$ | 3.870 g/cm$^3$ | 4.842 g/cm$^3$ | 5.393 g/cm$^3$ |
| Absorption coefficient | 25.384 mm$^{-1}$ | 19.219 mm$^{-1}$ | 17.925 mm$^{-1}$ | 33.373 mm$^{-1}$ |
| F(000) | 532 | 964 | 1912 | 1184 |
| Crystal size (mm$^{-3}$) | 0.062 × 0.046 × 0.031 | 0.191 × 0.160 × 0.109 | 0.071 × 0.053 × 0.044 | 0.265 × 0.022 × 0.013 |
| θ range | 2.72 to 24.99° | 2.82 to 29.01° | 3.03 to 28.96° | 2.26 to 29.16° |
| Index ranges | −10 <= h <= 7, −9 <= k <= 10, −8 <= l <= 9 | −10 <= h <= 12, −11 <= k <= 11, −17 <= l <= 17 | −15 <= h <= 15, −14 <= k <= 15, −15 <= l <= 15 | −14 <= h <= 14, −5 <= k <= 6, −22 <= l <= 24 |

-continued

| | Compound | | | |
|---|---|---|---|---|
| | δ-HC(NH$_2$)$_2$PbI$_3$ (4b) | δ-CH$_3$NH$_3$Sn$_{0.46}$Pb$_{0.54}$I$_3$ (5b) | α-Cs$_2$SnI$_6$ (6b) | δ-CsPbI$_3$ (7) |
| Reflections collected | 1687 | 4728 | 3871 | 7985 |
| Independent reflections | 354 [R$_{int}$ = 0.0759] | 788 [R$_{int}$ = 0.0738] | 143 [R$_{int}$ = 0.0595] | 1330 [R$_{int}$ = 0.0733] |
| Completeness to θ | θ = 24.99°, 100% | θ = 29.01°, 100% | θ = 28.96°, 100% | θ = 29.16°, 99% |
| Data/restr./param. | 354/3/17 | 788/2/22 | 143/0/7 | 1330/0/32 |
| Goodness-of-fit | 1.055 | 1.162 | 1.483 | 1.069 |
| Final R indices [>2σ(I)] | R$_{obs}$ = 0.0437, wR$_{obs}$ = 0.1066 | R$_{obs}$ = 0.0678, wR$_{obs}$ = 0.1732 | R$_{obs}$ = 0.0317, wR$_{obs}$ = 0.0697 | R$_{obs}$ = 0.0266, wR$_{obs}$ = 0.0457 |
| R indices [all data] | R$_{all}$ = 0.0516, wR$_{all}$ = 0.1102 | R$_{all}$ = 0.0809, wR$_{all}$ = 0.1809 | R$_{all}$ = 0.0322, wR$_{all}$ = 0.0698 | R$_{all}$ = 0.0364, wR$_{all}$ = 0.0477 |
| 2$^{nd}$ twin domain | [−1 −1 0 0 1 0 0 0 −1] 39(7)% | [−½ ½ −½ ½ −½ −½ −1 −1 0] 25(1)% | — | — |
| Flack parameter | [−1 0 0 0 −1 0 0 0 −1] 0(3)% | [−1 0 0 0 −1 0 0 0 −1] 28(5) % | — | — |
| 2$^{nd}$ domain Flack parameter | not refined | [½ ½ −½ ½ ½ −½ −1 −1 0] 22(1)% | — | — |
| Extinction coefficient | 0.0081(15) | 0.00084(10) | 0.00247(12) | 0.0127(3) |
| Largest diff. peak/hole | 1.975/−0.721 e.Å$^{-3}$ | 2.980/−2.175 e.Å$^{-3}$ | 1.005/−1.241 e.Å$^{-3}$ | 0.887/−1.986 e.Å$^{-3}$ |
| Wavelength | 0.71073 Å | | | |
| Refinement method | Full-matrix least-squares on F$^2$ | | | |

R = Σ||F$_o$| − |F$_c$||/Σ|F$_o$|, wR = {Σ[w(|F$_o$|$^2$ − |F$_c$|$^2$)$^2$]/Σ[w(|F$_o$|$^4$)]}$^{1/2}$ and calc
w = 1/[σ$^2$(Fo$^2$) + (0.0262P)$^2$ + 0.0000P] where P = (Fo$^2$ + 2Fc$^2$)/3

Both CH$_3$NH$_3$SnI$_3$ and CH$_3$NH$_3$PbI$_3$ distort in a similar manner in their β-phase, showing out-of-phase tilting of the polyhedra combined with ferroelectric type of off-centering along the c-axis adopting the tetragonal I4 cm space group. The ferroelectric displacement component is once again microscopic effecting a slight polarization of the octahedra along the c-axis. The tilting angle is 17.4° and 16.4° for CH$_3$NH$_3$SnI$_3$ and CH$_3$NH$_3$PbI$_3$ as measured at 150K and 293K, respectively. At 180K the framework of HC(NH$_2$)$_2$SnI$_3$ is found to be orthorhombic Imm2. The onset of the transition is at approximately 250K. It displays two major distortions at 9.7° and 11.2° and a minor one at 2.2°. HC(NH$_2$)$_2$PbI$_3$ at 150K adopts the P3 trigonal space group following a quadrupling of the room temperature cell volume. There is a broad array of distortions, due to significant off-centering of Pb, roughly averaged between the values of 9.0° and 11.5°. For good measure, the 373K distortion of β-CsSnI$_3$ is 18.

It was apparent that the methylammonium compounds have a tendency to distort the octahedra in the out-of-phase mode, whereas formamidinium phases seem to distort in-phase, the latter being similar to β-CsSnI$_3$. Contrary to the purely inorganic phase, however, the distortions lead to lower symmetry of the lattice whence the tilting of the octahedra is less severe.

γ-Phase Structures:

As the temperature continues to decrease further symmetry lowering occurs leading to the γ-phases. The γ-phase is encountered close to 100K, but for γ-CH$_3$NH$_3$PbI$_3$ this temperature was found to be at −150K. The γ-phases were easily recognizable from diffraction studies because of an intense broadening and splitting of the Bragg peaks in addition to the extra spots that appear. This can be clearly seen in the precession images generated from diffraction data collected at 100K, as compared to those created from room temperature data. We were unable to solve the structure of the γ-phases mostly because about 50% of the observed peaks remain unindexed during the unit cell determination. The unindexed peaks result from the formation of multiple twin domains which are created by the "freezing" of the cations (and subsequently the perovskite lattice) in different orientations. From our attempts to solve the crystal structures, we estimate that the γ-phases adopt a monoclinic crystal system. The methylammonium phases of Sn and Pb seem to acquire a C-centered cell whereas the formamidinium perovskites seem to adopt a primitive cell. It is however necessary to highlight a distinction between the methylammonium and formamidinium behavior; whereas the γ-phase of the former contains many split peaks, for the latter the splitting is much less intense and instead superlattice ordering was observed leading to multiplication of the parent unit cell. This may be attributed to the lower point group symmetry of CH$_3$NH$_3$$^+$ (C$_{3v}$) as opposed to that of HC(NH$_2$)$_2$$^+$ (C$_{2v}$, with the latter being more "flexible" to comply with the lattice distortions.

δ-Phase Structures:

Interestingly, the δ-phase of HC(NH$_2$)$_2$PbI$_3$ is markedly different from the δ-phase occurring in CsSnI$_3$ and CsPbI$_3$; in the latter case the structure comprises a double chain of MI$_6$$^{4-}$ octahedra. The intra-chain linking of the polyhedra in the individual chains is affected by edge-sharing of square bipyramidal units. The octahedral coordination occurs by inter-chain bonding by a relatively longer M-I bond with an iodide occupying a basal position of the square pyramid, overall adopting the NH$_4$CdCl$_3$-structure type. δ-HC(NH$_2$)$_2$PbI$_3$ on the other hand, consists of face-sharing octahedra propagating along the 001 direction forming single chains, with the cations occupying the space between the chains, thus adopting a nearly hcp-lattice (P6$_3$mc). The deviation from the ideal symmetry can be attributed to the HC(NH$_2$)$_2$$^+$ cations which lack a center of inversion despite the fact that the nitrogen atoms where treated as disordered during the structure determination process. At this point we should stress that the black-to-yellow transformation is a reversible effect. For example, when a single crystal of δ-HC(NH$_2$)$_2$PbI$_3$ was heated at 400K for ~2 h a polycrystalline black solid was formed instead, though not in a single-crystal-to single-crystal manner. Interestingly, while the α- to δ-phase transformation can be repeated indefinitely in the mother liquor by running heating and cooling cycles in the absence of a liquid medium the transformation was irreversible; i.e. the polycrystalline black material of the α-phase obtained from heating a crystal of the δ-phase did not convert back to the yellow phase on cooling or it does so only very slowly. This was likely due to the partial loss of formamidinium forming a defective compound.

Thermal Analysis.

The thermal analysis results of the hybrid perovskites presented here show similar trends for Sn and Pb. The experiments were conducted under a nitrogen flow to avoid oxidation. Thermogravimetric analysis of the materials showed that they decomposed before melting. Decomposition started at temperatures >300° C. and proceeded in one step. The mass loss corresponds to loss of the organic cation and all the iodide content leaving a metallic residue.

The decomposition profiles seemed to be dependent on the synthetic conditions used to prepare the compounds. When the materials were prepared in air the decomposition followed a different pathway that included two distinct weight loss steps. In that case, the decomposition proceeded initially with a mass loss corresponding to "CH$_3$NH$_3$I" or "HC(NH$_2$)$_2$I", possibly in the form of the free amine and HI, followed by a second step in mass loss corresponding to loss of HI molecules. An example of this is CH$_3$NH$_3$SnI$_3$, where the mass loss depended on the preparative method employed. In that sense it seems unlikely that the first decomposition step is associated with loss of the organic cation alone. It is clearly seen that the mass loss is associated with the purity of the material. For example, when the material was prepared by grinding, the first step of decomposition displayed a much greater mass loss as compared to the material prepared by high temperature solid state or solution methods. A plausible explanation for this behavior is the presence of Sn$^{IV}$ species in the compounds. In that case, the mass loss could be associated with the liberation of volatile SnI$_4$. Contributing to the weight loss is the liberation of CH$_3$NH$_3$I (in the form of CH$_3$NH$_2$ and HI) which is driven away due to the formation of Sn$^{IV}$ species. It is worth pointing out that the decomposition temperature for pure CH$_3$NH$_3$I is roughly 280° C., while the decomposition of partly oxidized CH$_3$NH$_3$SnI$_3$ (with weight loss) starts at ~150° C. Further support for the presence of Sn$^{IV}$ species, is provided by the absence of a corresponding "two step" decomposition profile in CH$_3$NH$_3$PbI$_3$. In the former case this could be explained by the inability of Pb$^{II}$ to oxidize to Pb$^{IV}$ in an all iodide environment.

In the case of compounds 3 and 4 a similar behavior was observed with the addition of a small mass loss associated with the evaporation of formamidine or one of its decomposition products. The case of HC(NH$_2$)$_2$PbI$_3$ (4a) was significantly more complicated as there was some contamination from phase (4b) which was probably responsible for the small exothermic mass loss observed at 270° C. A fully decolorized (pale brown) residue remained, indicating the complete loss of iodine from the solid after the analysis.

Differential thermal analysis and differential scanning calorimetry studies were performed on the materials, aiming to detect any possible phase transitions that occur above room temperature. The only thermal event that could be detected between room temperature and the decomposition temperature was the evaporation of formamidine or a formamidine-related compound (endothermic) at 70° C. and an exothermic event for 4a at 270° C. both of which were related to mass losses and were therefore irreversible. The unexpected result came from CH$_3$NH$_3$PbI$_3$ (3) where no reversible phase transition could be detected with DTA or DSC measurements. As stated above, CH$_3$NH$_3$PbI$_3$ did undergo a structural phase transition going from tetragonal to pseudo-cubic symmetry between 300 and 400K as determined by single-crystal diffraction studies. The reason for the absence of any thermal signal for this transition may suggest that the transition is of second order. The transition itself does not involve chemical bond cleavage/formation; the only real change is associated with lowering of symmetry. Subsequently, the change in the heat capacity of the material, $C=Q/\Delta T$, is expected to be small and explains the lack of signal in DTA- and DSC.

Figure 22A:
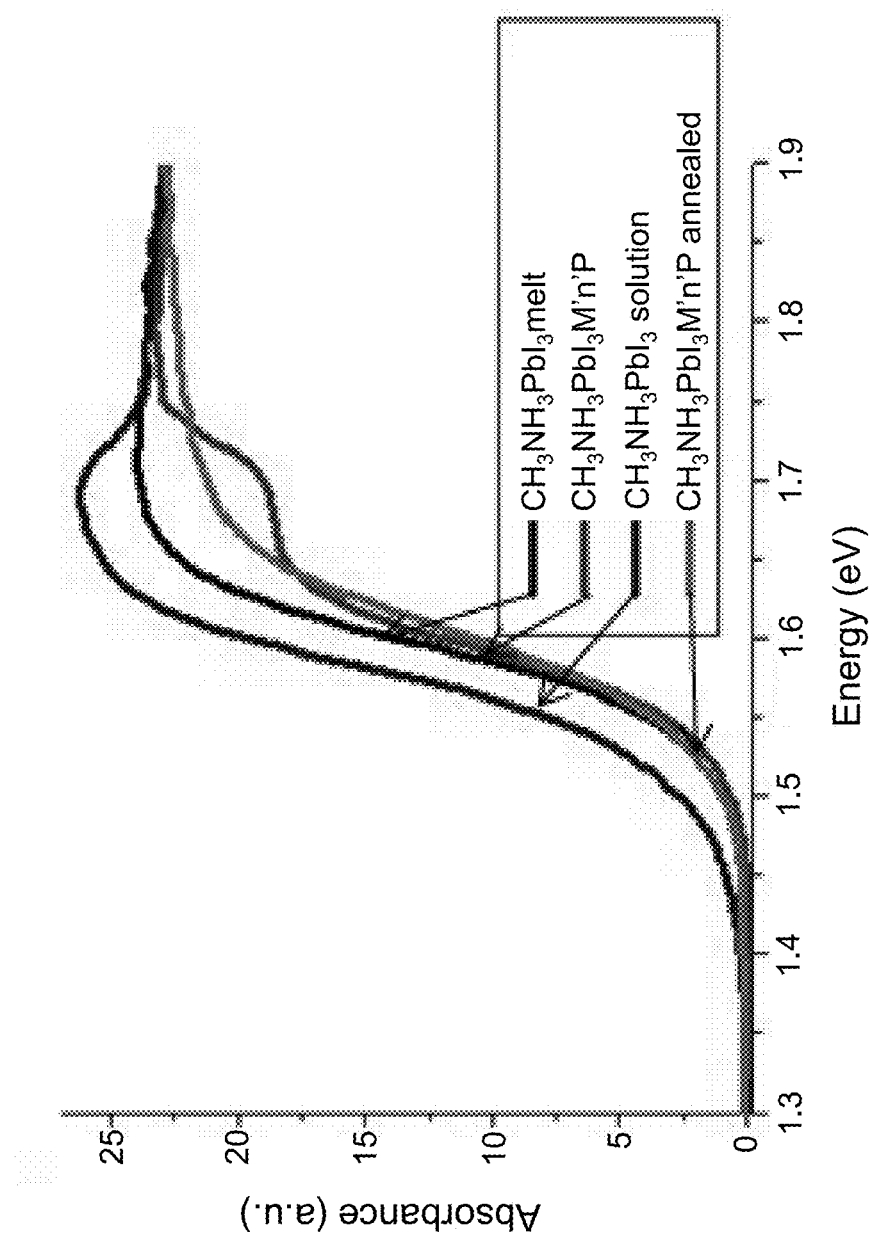
FIG. 22. Electronic absorption spectra of specimens 1-4 of Example 2. (A) and (B) highlight the band gap variability on the basis of the synthetic approach that was employed to prepare the sample.
Figure 22B:
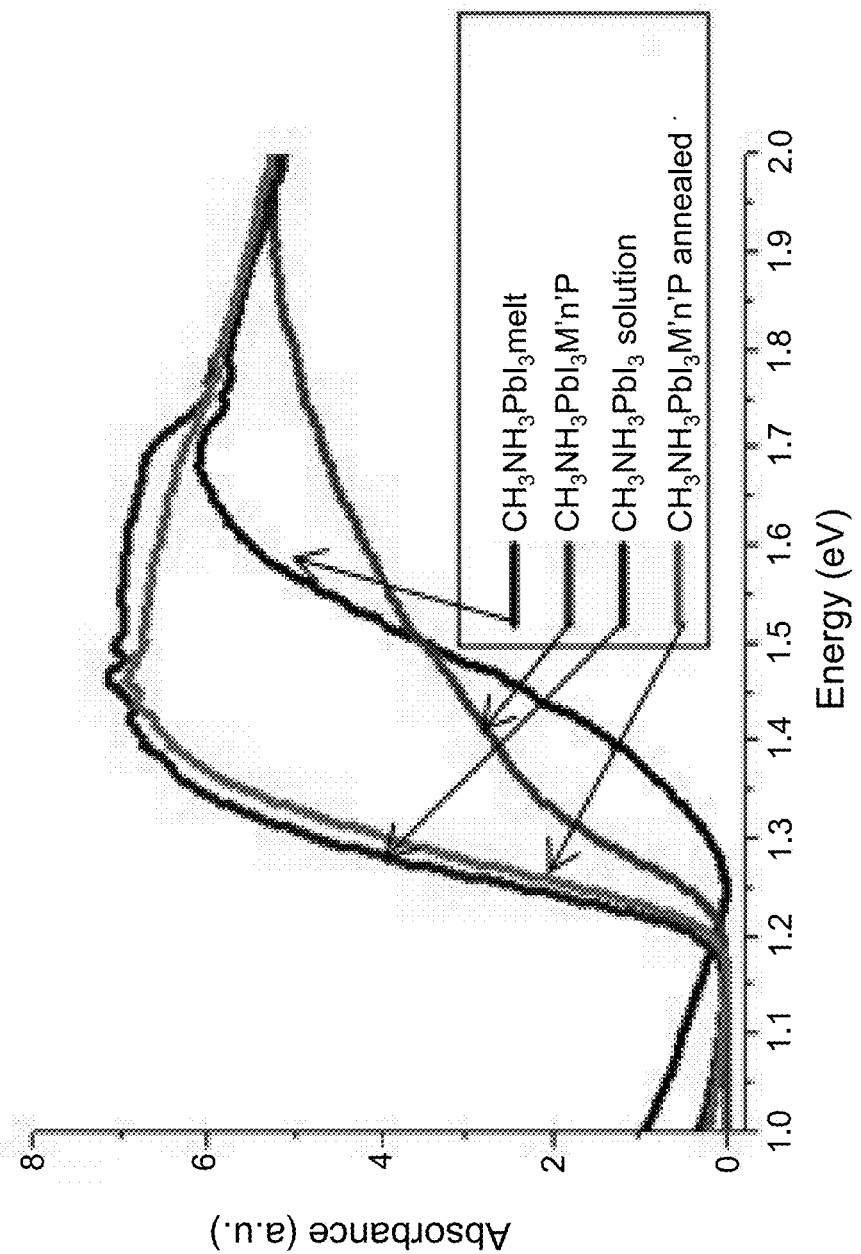
Figure 22C:
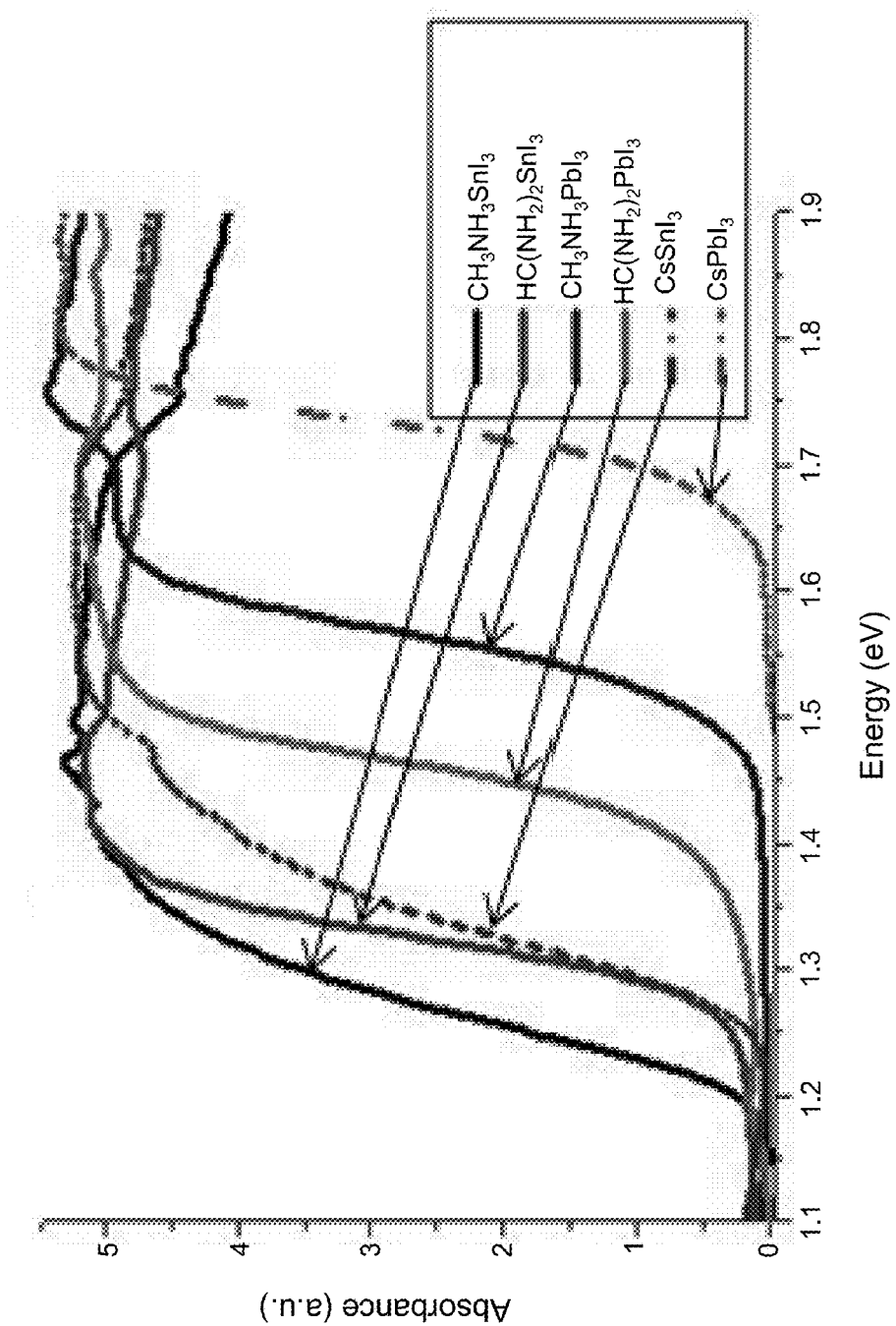

Optical Properties.

a) Electronic Spectroscopy:

The optical absorption of the materials was measured using a diffuse reflectance UV-vis-NIR spectrometer. All materials display a strong, abrupt absorption in the visible spectral region (FIG. 22). The absorption has been attributed to the energy gap between the conduction and the valence bands, thus classifying the materials as medium-bandgap semiconductors. The Sn and Pb based materials display an optical bandgap between 1.2 and 1.6 eV, in good agreement with the black color of the solids.

The band gaps of the Sn-based perovskites have mean values between 1.2-1.35, with CH$_3$NH$_3$SnI$_3$ (1) having a consistently smaller band gap with respect to HC(NH$_2$)$_2$SnI$_3$ (2) for every preparative method employed. We use the term "mean value" because as can be seen in the electronic absorption spectra of FIGS. 22 (A) and (B) there is a variation of the band gap as a function of the preparative method. There is no obvious trend on this variation besides the interesting fact that CH$_3$NH$_3$SnI$_3$ as prepared in an open tube (1.35 eV) and as prepared from solution or in the sealed tube reaction (1.21 eV) show a very striking difference. This is despite the fact that their thermal behavior is very similar as is their diffraction pattern. When compared with CsSnI$_3$, both 1 and 2 show a slight narrowing on the gap which is consistent with the lowering in the symmetry of the [SnI$_3$]$^-$ framework.

Figure 23B:
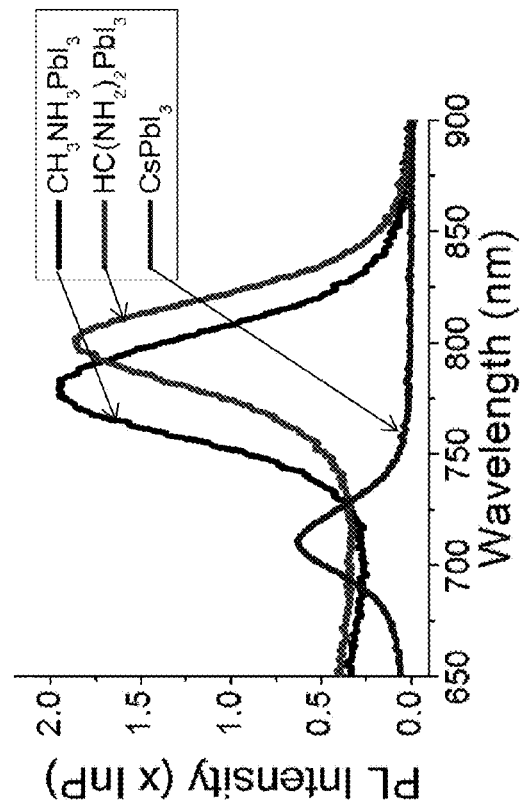
FIG. 23. Photoluminescence spectra of (A) $ASnI_3$ and (B) $APbI_3$ as obtained from the open tube reaction. The data are normalized towards a single crystalline sample of InP which is used as a benchmark. The Cs analogues, prepared in the same manner are given for comparison purposes.

The Pb-based phases, however, have band gaps which were independent of the preparation method at 1.41 and 1.52 eV for HC(NH$_2$)$_2$PbI$_3$ (4a) and CH$_3$NH$_3$PbI$_3$ (3), respectively. As in the case of the Sn-phases, a narrowing of the band gap was observed for the Pb compounds upon symmetry lowering, when compared to the room temperature absorption of the black perovskite form of CsPbI$_3$ obtained by a solid state reaction, before the material transitions to the yellow non-perovskitic phase (FIG. 22(C)). The absorption edge for both the Sn- and Pb-based phases is sharp, suggesting a direct band separation.

b) Photoluminescence (PL) Properties:

The photoluminescence properties of specimens obtained from all four synthetic approaches (solution, grinding, open tube melting, sealed tube annealing) were measured using a green light source at 532 nm and a specialized photoluminescence spectrometer. The solution samples showed no PL at all with the exception of HC(NH$_2$)$_2$PbI$_3$. FIGS. 23 (A) and (B) show typical emission spectra of the hybrid perovskites prepared by grinding the precursors and heating the samples at 350° C. for 20 sec.

Generally, the grinding method produced consistently high photoluminescence Annealing of the ground material also produced solids with respectable luminescence, slightly weaker than the ground ones, but the materials were highly homogeneous. However, it should be stated that exhaustive annealing, i.e. >24 h quenched the PL emission (see below). When working under vacuum the materials obtained were pure and homogeneous, though the PL-properties were noticeably weakened compared to the materials prepared at ambient pressure. When these materials were exposed to the atmosphere, they decomposed within a few minutes, displaying an extreme sensitivity. The solution-processed solids of both Sn and Pb perovskites were PL-inactive. This suggests that the presence of defects such as $Sn^{4+}$ species in the structure which are more likely to be present in the samples made by solid state methods is probably associated with the photoluminescence.

As stated above, there is a significant variation of optical absorption properties of these materials that depends strongly on the preparation method. Therefore, it is not surprising that the emission properties differ to some extent. If PL comes from defects it should increase as the symmetry is lowered via twinning, artificially creating defects, or due to change of the band structure to generate PL-favorable conditions. The temperature dependence of the PL intensity/wavelength has been confirmed in $CsSnI_3$. When one of the other three methods (grinding, open tube melting, sealed tube annealing) was employed, the resulting polycrystalline materials should have had many more defects. We suppose that this might be the source of photoluminescence enhancement. A further supporting indication of the defect-induced PL model is that the only solution prepared material that showed some PL-activity was $HC(NH_2)_2PbI_3$ which underwent a phase transformation from a perovskite structure to a non-perovskite structure, incidentally forming a highly defective perovskite phase during the transformation. Therefore, the defects seem to play a crucial role in the expression of the PL, either when these are created during the synthesis or by means of temperature-controlled structural changes. This is supported by the observed trend which is: the cruder the synthesis the higher the PL intensity.

In FIGS. 23 (A) and (B), the PL properties of Sn and Pb hybrid materials are presented along with the corresponding Cs phases. The magnitude of the emission is rather comparable with one another, except for $CsPbI_3$ in which the perovskite black phase, which is stable above ~300° C., very rapidly converts to the PL-non active yellow phase. The samples were prepared from the melt in order for the data to be comparable. There is a small but real shift in the emission wavelength and each emission wavelength matches quite well with the corresponding absorption energy edge.

Charge Transport Properties.

In order to further understand this behavior resistivity measurements were performed on 1-3. Freshly prepared samples using the solution method were employed using an isopropanol graphite suspension to generate the electrical contacts. This was found to be a necessary precaution to avoid possible redox effects resulting from direct contact of the material with a metal surface. Single-crystals prepared from the solution method (0.1-1 mm length) and cold-pressed pellets from the annealing method ($1.67 \times 1.67 \times 5.00$ mm$^3$) were investigated. The samples were measured using both a PPMS 4-probe setup for low temperature data and a conventional 4-probe method for room and high temperature measurements.

Low-Temperature Resistivity:

Low temperature data were collected in the 5-330K range for single-crystals of 1-3 using the PPMS instrumentation where a similar behavior for the three compounds was observed. The initial high resistivity values obtained at 5K gradually decreased as the temperature increased and at ~330K was 4 Ωcm for $CH_3NH_3SnI_3$, 34 Ωcm for $HC(NH_2)_2SnI_3$ and 596 Ωcm for $CH_3NH_3PbI_3$). This trend in the resistivity vs. temperature was characteristic of semiconductors, unlike metals which show the exact opposite trend. On cooling, resistivity increased again down to 5K, slightly decreased in the case of 1 and slightly increased in the case of 2 and 3, showing a hysteretic behavior. This hysteresis comes as a consequence of the structural phase transitions. In fact, the structural phase transitions were reflected as anomalies in the resistivity close to the transition temperature. Thus, compound 1 changed to the β-phase in the 200-220K region followed by one more transition to the γ-phase around 130K. A resistivity increase around 70K suggested more phase transitions were possible on lowering the temperature. Similarly, for compounds 2 and 3 the β-phase was reached at 260K and 320K, respectively, while the γ-phase was observed at 110K and 180K, respectively. The transition temperatures were in good agreement with the transition observed in X-ray diffraction studies discussed above. In the case of 3 where the α/β phase transition occurs above room temperature, resistivity data were also collected in the 300-400K region using the setup described in the Experimental Section, revealing a sharp transition with an onset at 310K.

Arrhenius plots of the resistivity data showed that the phase transitions have activation energies of two types related to both electronic and vibrational energy barriers. The high-energy electronic barriers correspond to the jumping of electrons from the valence band to the conduction band and indeed are in good (in 1) or fair (in 3) agreement with the energy gap obtained from the optical measurements. In 2, however, no sharp electronic barrier showed up and instead the increase in the resistivity progressed through broad, low activation energy transitions which can be attributed to molecular motions of the organic cation. Such low energy transitions can be seen in 1 as well.

Room Temperature and High-Temperature Resistivity:

Cold-pressed rectangular pellets ($1.67 \times 1.67 \times 5.00$ mm$^3$) of (1-4) and/or elongated rhombic dodecahedral single-crystal ($0.5 \times 0.5 \times 0.5$ mm$^3$) of (1-3) were also measured using the conventional 4-probe method. A remarkable behavior could be easily spotted differentiating $CH_3NH_3PbI_3$ from its other perovskite counterparts. The difference lies in the strongly non-ohmic characteristics of 3 evident in the I-V curves of the measured materials. On the other hand, $CH_3NH_3SnI_3$, $HC(NH_2)SnI_3$ and $HC(NH_2)PbI_3$ display a nearly perfect ohmic behavior with a resistivity values of 0.49, 11.8 and $3.4 \times 10^3$ Ωcm at 300K following a declining trend with increasing temperature.

$CH_3NH_3PbI_3$ was singled-out since it reproducibly displays a non-ohmic behavior with a parabolic I-V dependence. The calculated resistivity value for a single-crystal of $CH_3NH_3PbI_3$, ignoring the non-linear parts of the plot, was 51 MΩ·cm at room temperature. Interestingly, the resistivity value varies slightly with the polarity of the applied electric field with a higher slope being obtained for negative polarity. The equilibrium value of the voltage for zero applied current (remnant polarization) was roughly −10 mV, but in general displays a strong dependence on the history of the crystal. These characteristics strongly imply a ferroelectric response (the point group 4 mm allows for such a behavior), however, as it will be explained below there is no sufficient evidence for this arising from charge transport measurements. The resistivity graphs of compounds 1, 2 and 4 on the contrary, display a normal ohmic behavior In terms of absolute resistivity there is a discrepancy between the low- and the high-temperature values. We rationalize this based on the I-V characteristics of 1-3. At room temperature, 1, 2 and 4a, which adopt the α-phase, displayed a nearly perfect ohmic behavior which resulted in resistivities in the $10^0$-$10^1$ Ωcm range for the Sn compounds and $10^3$ Ωcm for the Pb compound. On the other hand, the β-phase of 3 displayed a remarkable non-ohmic behavior which was responsible for a hysteresis loop obtained in its I-V plot. The hysteretic behavior can probably be attributed to the reorientation of the permanent dipoles of $CH_3NH_3^+$ on application of external electric field, in addition to the resistance of the inorganic $\{PbI_3\}^-$ lattice. Thus, a capacitance/inductance factor was introduced to the charge transport which reflects the ability of the permanent dipoles to align with the applied field while confined within the perovskite "cube".

Thermopower:

In order to assign the carrier type in the perovskite compounds, we performed Seebeck thermopower measurements (Seebeck coefficient) on both solution derived single-crystals of 1-3 and cold-pressed pellets of 1-4 fabricated from powders of the annealed samples. The compound $HC(NH_2)PbI_3$ could only be measured in the latter form, since the pressure applied to form the pellets (~10 GPa) was sufficient to stabilize the perovskite (black) form for several hours. The thermopower of the single crystals for compounds 2 and 3 in the 300-400K range were negative and very large in magnitude indicating that the materials are n-type semiconductors with very low levels of electron carriers. The Seebeck coefficients were −2700 and −6500 µV/K at 380K for 2 and 3, respectively. These values are consistent with carrier concentration of $<10^{17}$ cm$^{-3}$. For compound 3, the Seebeck value was sensitive to the phase transition, consistent with the overall change of the other transport properties.

In order to have a more complete picture of the transport characteristics, a complete collection of 1-4 and 5b (see below) was prepared as cold-pressed from annealed powders obtained from the grinding method. All samples prepared this way had nearly identical geometric dimensions which allowed for a direct comparison of their electron transport properties. Interestingly, with the exception of 4a which is p-type, all samples displayed a n-type behavior. The Pb-containing samples invariably showed an extremely high Seebeck coefficient in the order of few (for 5b) to several (for 3 and 4b) mV/K indicative of very low carrier concentration. The Sn-based compounds (including a sample of similarly prepared $CsSnI_3$), on the other hand, showed significantly lower Seebeck coefficients, on the order of few hundreds of µV/K, indicating a higher carrier concentration (still low as an absolute value) with respect to the Pb analogues. The samples still behaved as semiconductors, as evidenced by resistivity measurements. It is important to point out that the thus measured resistivity is not very precise since in that type of samples the grain boundaries are expected to significantly increase the resistivity. However, when the pressed pellets were made from not annealed samples, a special behavior was observed for the Sn compounds, which displayed a remarkable change in the sign of the thermopower behaving as p-type semiconductors.

Hall-Effect Measurements:

Hall effect measurements were also performed in the cold-pressed samples of annealed polycrystalline 1-3 and 5b in order to estimate the carrier concentration of the compounds. The specimens were measured under a variable magnetic field of 0.5-1.25 T under a constant excitation of 10 µA for the less resistive samples (1, 2, 5b) and 100 nA for compound 3. The results confirm the negative sign of the carriers (n-type) for all the thus prepared compounds. The carrier concentrations were on the order of $10^{14}$ cm$^{-3}$ for 1, 2 and 5b, while the respective carrier concentration for compound 3 was found to be on the order of $10^9$ cm$^{-3}$. For the former, data were in excellent agreement with the Seebeck measurement which suggest a very low carrier concentration corresponding to nearly intrinsic semiconducting behavior. This argument is further corroborated by the fact that the specimens, except the p-type compound 4a, did not display any PL signal after the measurements indicating depletion of the charge carriers. The depletion was probably caused by the "exhaustive" thermal treatment during sample preparation and several heating/cooling cycles during the measurements. Combining resistivity and Hall effect data (measured for the same specimens), the electron mobility was calculated to be 2320 cm$^2$/V·s for $CH_3NH_3SnI_3$, 103 cm$^2$/V·s for $HC(NH_2)_2SnI_3$, 270 cm$^2$/V·s for $CH_3NH_3Sn_{0.5}Pb_{0.5}I_3$ and 66 cm$^2$/V·s for $CH_3NH_3PbI_3$.

Comparing our present experimental results with the established literature data, we find that the evaluation on the charge transport properties has been quite different than that previously anticipated. The resistivity for $CH_3NH_3SnI_3$ for example is higher by at least one or two orders of magnitude from previously reported samples, and this is due to the differences in the synthetic approach, as discussed below. More importantly, we find that the overall evaluation of the Sn compounds asp-type "metals" needs to be revised since our results clearly indicate that $CH_3NH_3SnI_3$ and $HC(NH_2)_2SnI_3$ can also behave as n-type semiconductors. The reason for the ability of these compounds to be p-type conductors (e.g. as in the case of $CsSnI_3$) is the unique property of the materials to spontaneously oxidize (through the $Sn^{2+}/Sn^{4+}$ path) and thus to transition to a doped state with charge carriers being holes through self-doping. The reason we were able to isolate the pure, very low charge carrier n-type semiconductors may be found in the use of a powerful reducing agent (i.e. $H_3PO_2$) which was able to inhibit/reverse the self-doping process (i.e. suppress formation of $Sn^{4+}$) and allows the isolation of the pure stoichiometric compounds. P-type conducting behavior was observed when the preparation of the Sn compounds was carried out through solid-state methods. The absence of the reducing agent rendered the $Sn^{2+}/Sn^{4+}$ conversion irreversible and therefore the obtained solids were inherently doped. The fact that Sn oxidation was responsible for the "metal-like" behavior in the solid state is evident by direct comparison with the Pb-analogues (which cannot undergo analogous $Pb^{2+}/Pb^{4+}$ doping) where the charge transport properties are practically unaffected by the preparative route, although some slight differences are still observed.

The most pronounced indication of this difference between the Sn and Pb compounds comes from studying their mid-IR spectra. At this region, one should expect to observe only absorptions arising from the vibrational motion of the organic cations, which was, in fact, the case for compounds 3 and 4a. However, in the case of Sn-based materials, these absorptions were masked by a broad absorption centered at 1000 cm$^{-1}$ (100 meV). This was possibly an intra-band transition close the top of the valence band between full $5s^2$ orbitals ($Sn^{2+}$) and (partially) vacant $5s^0$ orbitals ($Sn^{4+}$). However, such a plasmon frequency requires a carrier concentration ~$10^{18}$-$10^{19}$ cm$^{-3}$ for a carrier effective mass of $m_e=1$ which is not supported by charge transport measurements. For $CH_3NH_3SnI_3$, where the largest and most intense plasmon frequency was observed, a huge electron mobility was also observed, which suggests that the effective mass of the $CH_3NH_3SnI_3$ compound should be very small. A similar behavior also occurred for compound 2, though it was much less intense in magnitude, further supporting the mobility argument since $HC(NH_2)_2SnI_3$ has a significantly lower mobility than $CH_3NH_3SnI_3$.

However, it is still possible to "un-dope" the semiconductors to a nearly carrier-depleted n-type state. This can be achieved with extensive thermal treatment at ~200° C., at which temperature $Sn^{+4}$ dopants are eliminated in the form of volatile $SnI_4$. Excess of the organic cations can also be partially removed at the annealing temperature in the form of the free amine and HI gas. Therefore, it is feasible to tune the doping levels within the Sn-based materials, and consequently the overall charge transport characteristics, simply by choosing the appropriate synthetic method to generate p- or n-type semiconductors in the $ASnI_3$ family of compounds.

In addition, the above results illustrate that the phase transitions determine the transport characteristics of the semiconducting perovskite compounds. In their highest symmetry (α-phase), the perovskites display the maximum conductivity, which is a consequence of the maximum orbital overlap between the metal and the iodine (linear Sn—I—Sn bond). As the phase transitions progress at lower temperatures (β- and γ-phases) the change in the M-I-M angles result in reduced orbital overlap, thus hindering the charge transport through the inorganic framework. The transport properties of β-$CH_3NH_3PbI_3$, in particular, where a capacitor-like behavior was observed, may be rationalized by the reorientation of the $CH_3NH_3^+$ dipoles on application of current through the material, which mask the properties of the inorganic $[PbI_3]^-$ framework.

$CH_3NH_3Sn_{1-x}Pb_xI_3$ Solid Solution Studies:

In the context of the above results, we decided to study the properties of $CH_3NH_3Sn_{1-x}Pb_xI_3$ solid solutions in order to explore the structure and property trends as a function of x. As shown above, these two phases follow the same phase transition path, albeit the transitions occur at different temperatures. The materials were studied as a function of the preparation route as described above.

The "quality" of the materials was clearly demonstrated here. It was obvious that the ground samples contained impurities when compared with the diffraction pattern of the simulated data from single-crystal diffraction. The other three preparative methods (open tube melting, sealed tube annealing, solution) provided sufficiently pure materials. The weak Bragg reflections observed near the triplet of major peaks at 24.7°, 28.6° and 32.1° 2θ angles was discussed earlier as an oxidation impurity. For materials prepared from the melt, the peak appeared already at the onset of the data collection. For samples obtained from solution synthesis and the annealed samples the minor reflections appear in the powder diffraction patterns only after prolonged exposure in air during data collection. The cleanest pattern was obtained from the annealed samples, because of strong diffraction requiring a considerably shorter collection time, so that substantial oxidation did not occur. Therefore, it was clear that these reflections were due to oxidation of Sn in the compounds since they did not appear in the diffraction patterns of pure Pb and Pb-rich phases.

The evolution of the structure in this solid solution system was consistent, irrespective of the method used. The Sn-rich regions adopted the pseudocubic tetragonal P4 mm structure of the parent α-$CH_3NH_3SnI_3$ compound up to x=0.5. For x>0.5 the structure changed to that of the tetragonal β-$CH_3NH_3PbI_3$, I4 cm.

Figure 23A:
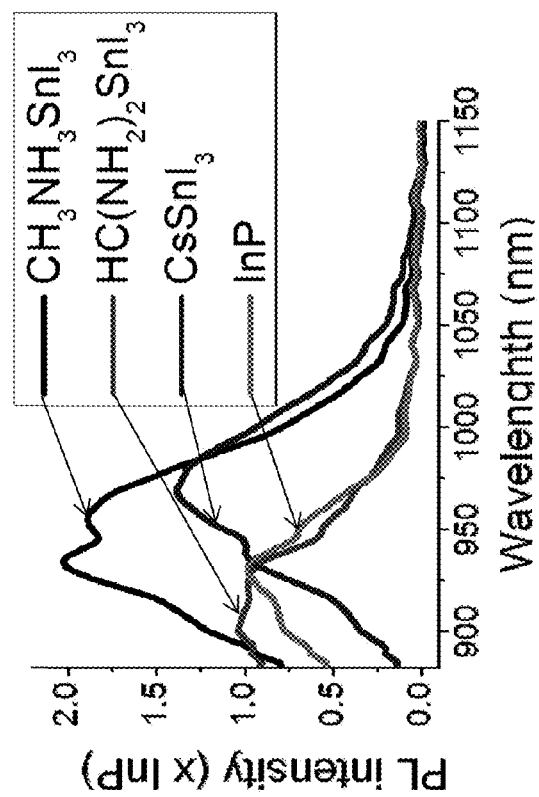
Figure 24B:
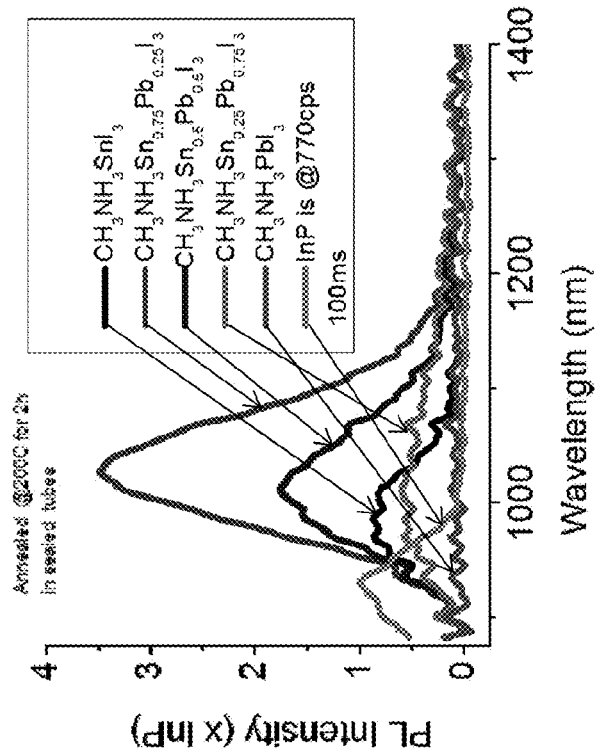
FIG. 24. Photoluminescence properties of $CH_3NH_3Sn_{1-x}Pb_xI_3$ solid solution as obtained from the mildly grinding the precursors (interface reaction) (A) and by annealing the same specimen at 200° C. for 2 h in a sealed tube (B). The data are normalized towards single crystalline InP.
Figure 24A:
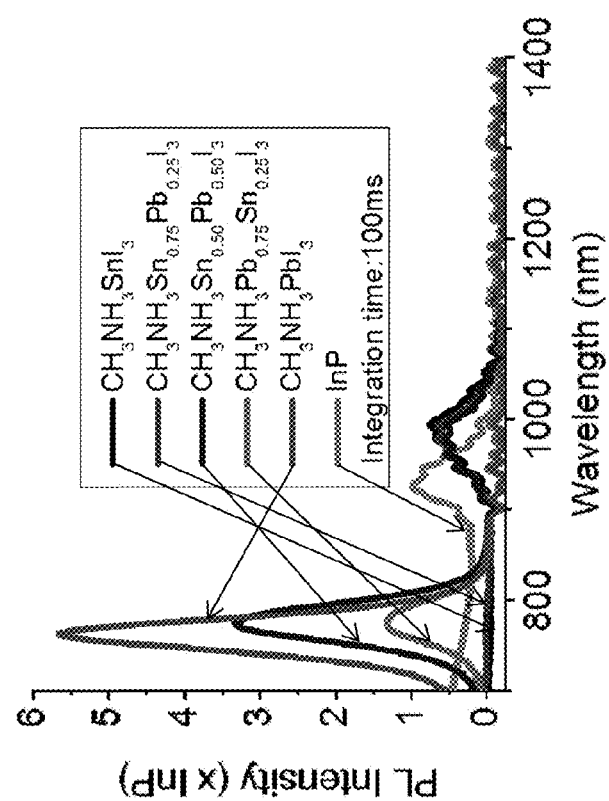
Figure 25A:
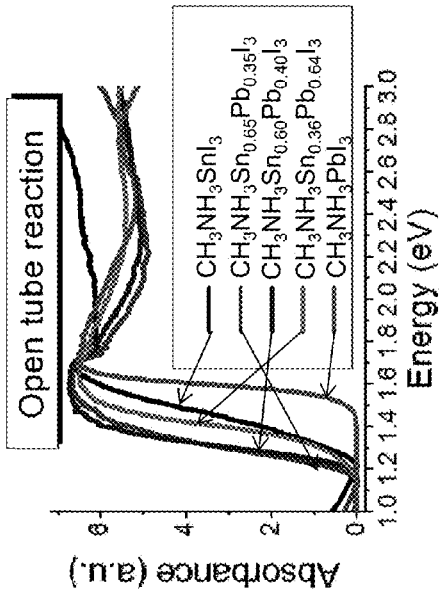
FIG. 25. Optical absorption properties of $CH_3NH_3Sn_{1-x}Pb_xI_3$ solid solution as obtained from: (A) grinding, (B), open tube melt, (C) sealed tube annealing and (D) solution reactions. In the cases where there is ambiguity on the Sn:Pb ratio the values were obtained from EDS analysis.
Figure 25B:
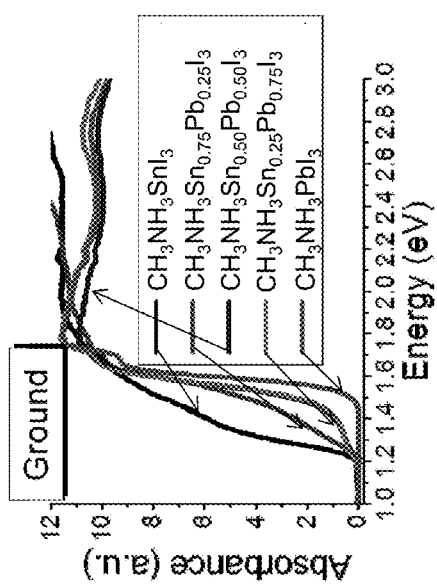
Figure 25C:
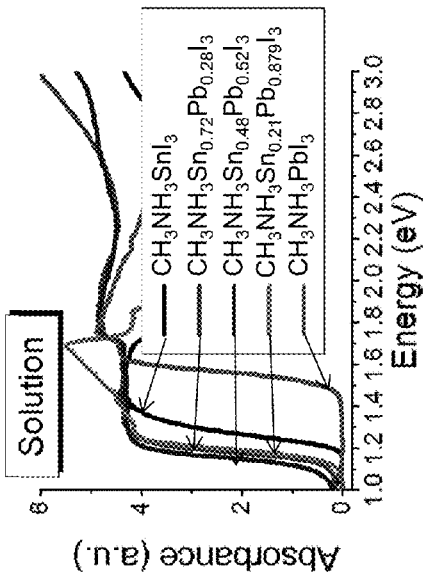
Figure 25D:
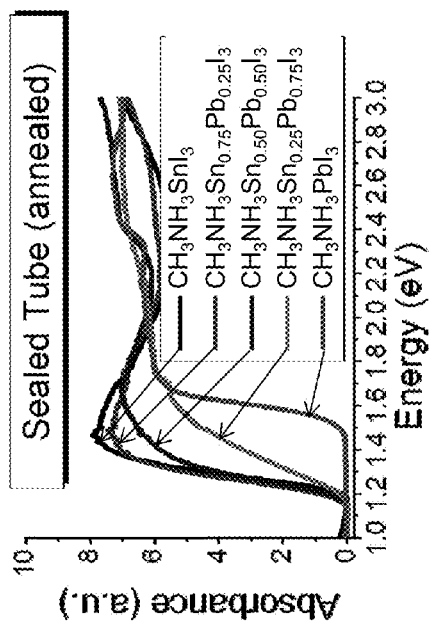

The photoluminescence properties of the materials are strongly affected by mixing the Sn and Pb sites (FIG. 24). Again, materials prepared from solution were not luminescent. The mixed-metal perovskites prepared from the melt were also inactive, in contrast to the pure phases prepared by the same method for x=0 and x=1. Intense photoluminescence was produced when the materials were prepared by mild grinding so that some unreacted solid remains (interface reaction). The photoluminescence intensity decreased as the mixture was thoroughly ground to a visually homogeneous black powder and the reaction was almost complete. The emission observed from this process corresponded to the individual Sn and Pb centers showing two peaks at the respective emission wavelengths (FIG. 23A). However, when the material was placed in a sealed tube and annealed at 200° C., the formation of the solid solution was complete and the Sn and Pb active centers were fully mixed. As a result, the initial emission peaks disappeared and a new emission peak occurred. This peak was red shifted and seemed to peak for x=0.25 which emits at 1030 nm. This is an overall red shift of 70 nm with respect to the end member $CH_3NH_3SnI_3$ (FIG. 24(B)). For x>0.25 the shift is smaller as is the intensity of the peak. As a rule of thumb, the intensity seemed to be slightly decreased by annealing.

The red shift in the emission wavelength was reflected in the absorption spectra which universally showed a shift to lower energies of absorption (FIG. 25). The largest band gap shift occurred in the materials obtained from solution, in the Pb-rich side of the solid solution reaching values of 1.1 eV. However, no emission could be detected in these specimens. The annealed materials showed an excellent agreement between absorption energy and emission wavelength.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

The invention claimed is:

1. A two-phase material comprising; a first phase of a compound having a formula selected from $AMX_3$, $A_2MX_4$, $AM_2X_5$ or $A_2MX_6$, where the A is selected from elements from Group 1 of the periodic table, the M is C, Ge, Sn or Pb, and X is selected from elements from Group 17 of the periodic table; and a second phase comprising a metal oxide of the formula $(M'O_{y'})$, where y'=1, 1.5 or 2, where M' is selected from elements of Groups 2-4 or elements of Groups 12-15 of the periodic table, and further wherein M and M' are different elements.

2. The material of claim 1, wherein the two-phase material is selected from the group consisting of $(CsSnI_3)_{1-x}(M'O)_x$, where M'=Si, Ge, or Pb; $(CsSnI_3)_{1-x}(M'O_{1.5})_x$, where M'=B, Al, Ga, In, Sc, or Y; $(CsSnI_3)_{1-x}(M'O_2)_x$, where M'=Si, Ge, or Pb; $(Cs_2SnI_4)_{1-x}(M'O)_x$, where M'=Si, Ge, or Pb; $(Cs_2SnI_4)_{1-x}(M'O_{1.5})_x$, where M'=B, Al, Ga, In, Sc, or Y; and $(Cs_2SnI_4)_{1-x}(M'O_2)_x$, M'=Si, Ge, or Pb, where 0.01<x<0.99.

3. The material of claim 1, wherein the two-phase material emits photoluminescence in the wavelength range from about 700 nm to about 2000 nm when it is irradiated with incident radiation having wavelengths in near-infrared or infrared regions of the electromagnetic spectrum.

4. The material of claim 1, where M' is selected from elements of Group 3, Group 13 or Group 15 of the periodic table and y'=1.5.

5. The material of claim 1, where M' is selected from elements of Group 14 of the periodic table and y'=1 or 2.

6. The material of claim 1, wherein M is Sn.

7. A two-phase material comprising: a first phase pound having the formula $AMX_3$, where the A is selected from elements from Group 1 of the periodic table, the M is selected from elements from Group 14 of the periodic table, and X is selected from elements from Group 17 of the periodic table; and a second phase comprising a metal oxide of the formula $(M'O_{y'})$, where y'=1, 1.5 or 2, where M' is selected from elements of Groups 2-4 or elements of Groups 12-15 of the periodic table, and further wherein M and M' are different elements, such that the two-phase material has the formula $(AMX_3)_{(1-x)}(M'O_{y'})_x$, where 0.01<x<0.99.

8. The material of claim 7, wherein the compound is $CsSnI_3$.

9. A two-phase material comprising: a first phase of a compound having the formula $A_2MX_4$, where the A is selected from elements from Group 1 of the periodic table, the M is selected from elements from Group 14 of the periodic table, and X is selected from elements from Group 17 of the periodic table; and a second phase comprising a metal oxide of the formula $(M'O_{y'})$, where y'=1, 1.5 or 2, where M' is selected from elements of Groups 2-4 or elements of Groups 12-15 of the periodic table, and further wherein M and M' are different elements, such that the two-phase material has the formula $(A_2MX_4)_{(1-x)}(M'O_{y'})_x$, where 0.01<x<0.99.

10. The material of claim 9, wherein the compound is $Cs_2SnI_4$.

11. A two-phase material comprising; a first phase of a compound having a formula selected from $AMX_3$, $A_2MX_4$, $AM_2X_5$ or $A_2MX_6$, where the A is selected from elements from Group 1 of the periodic table, the M is selected from elements from Group 14 of the periodic table, and X is selected from elements from Group 17 of the periodic table; and a second phase comprising a metal halide of the formula $A_2M'X_6$ where M' is Si, Ge, Ti, Zr or Hf, or $A_3M'X_6$, where M' is Al, Ga, In, Sc or Y.

12. The material of claim 11, wherein the compound is $CsSnI_3$ or $Cs_2SnI_4$.

13. The material of claim 11, wherein the two-phase material is selected from the group consisting of $(CsSnI_3)_{1-x}(Cs_{1.5}M'_{0.5}F_3)_x$, M'=Al, Ga, In, Sc, or Y; $(CsSnI_3)_{1-x}(CsM'_{0.5}F_3)_x$, M'=Ge, Ti, Zr, or Hf; $(Cs_2SnI_4)_{1-x}(Cs_{1.5}M'_{0.5}F_3)_x$, M'=Al, Ga, In, Sc, or Y; and $(Cs_2SnI_4)_{1-x}(CsM'_{0.5}F_3)_x$, M'=Si, Ge, Ti, Zr, or Hf, where 0.01<x<0.99.

14. The material of claim 11, wherein the metal halide has the formula $A_3M'X_6$ and M' is Al.

15. The material of claim 11, wherein the compound has the formula $AMX_3$ and the $AMX_3$ compound comprises two X elements, such that the compound has the formula $AMX_{(3-x)}X'_x$, where X and X' are different halogen atoms and 0.01<x<0.99.

16. The material of claim 15, wherein X is I and X' is F.

17. The material of claim 11, where M' is Ga or In and the metal halide has the formula $A_3M'X_6$.

18. The material of claim 11, where M' is Ge and the metal halide has the formula $A_2M'X_6$.

19. A two-phase material comprising: a first phase of a compound having a formula selected from $AMX_3$, $A_2MX_4$, $AM_2X_5$ or $A_2MX_6$, where the A is selected from elements from Group 1 of the periodic table, the M is C, Ge, Sn or Pb, and X is selected from elements from Group 17 of the periodic table; and a second phase comprising a metal oxide of the formula $(M'O_{y'})$, to provide the two-phase material with the formula $(AMX_3)_{(1-x)}(M'O_{y'})_x$, $(A_2MX_4)_{(1-x)}(M'O_{y'})_x$, $(AM_2X_5)_{(1-x)}(M'O_{y'})_x$, or $(A_2MX_6)_{(1-x)}(M'O_{y'})_x$, where 0.3≤x<0.99 and y'=1, 1.5 or 2, where M' is selected from elements of Groups 2-4 or elements of Groups 12-15 of the periodic table.

20. The material of claim 19, wherein M' is Sn, Al, Pb, Si or B.

21. The material of claim 19, where 0.5<x.

22. The material of claim 19, wherein the compound is $CsSnI_3$ and the metal oxide is SnO.

23. The material of claim 19, wherein M is Sn.

\* \* \* \* \*